(12) United States Patent
Gillies et al.

(10) Patent No.: US 7,148,321 B2
(45) Date of Patent: Dec. 12, 2006

(54) EXPRESSION TECHNOLOGY FOR PROTEINS CONTAINING A HYBRID ISOTYPE ANTIBODY MOIETY

(75) Inventors: Stephen D. Gillies, Carlisle, MA (US); Kin-Ming Lo, Lexington, MA (US)

(73) Assignee: EMD Lexigen Research Center Corp., Billerica, MA (US)

( * ) Notice: Subject to any disclaimer, the term of this patent is extended or adjusted under 35 U.S.C. 154(b) by 82 days.

(21) Appl. No.: 10/093,958

(22) Filed: Mar. 7, 2002

(65) Prior Publication Data

US 2003/0044423 A1    Mar. 6, 2003

Related U.S. Application Data

(60) Provisional application No. 60/274,096, filed on Mar. 7, 2001.

(51) Int. Cl.
    C07K 5/00    (2006.01)
(52) U.S. Cl. .................. 530/300; 530/350; 530/387.3; 424/130.1; 424/133.1; 424/134.1
(58) Field of Classification Search ............... 530/300, 530/350, 387.3; 424/130.1, 133.1, 134.1
    See application file for complete search history.

(56) References Cited

U.S. PATENT DOCUMENTS

| | | |
|---|---|---|
| 4,196,265 A | 4/1980 | Koprowski et al. |
| 4,469,797 A | 9/1984 | Albarella |
| 4,676,980 A | 6/1987 | Segal et al. |
| 4,703,008 A | 10/1987 | Lin |
| 4,816,567 A | 3/1989 | Cabilly et al. |
| 4,946,778 A | 8/1990 | Ladner et al. |
| 5,019,368 A | 5/1991 | Epstein et al. |
| 5,073,627 A | 12/1991 | Curtis et al. |
| 5,114,711 A | 5/1992 | Bell et al. |
| 5,116,964 A | 5/1992 | Capon et al. |
| 5,199,942 A | 4/1993 | Gillis |
| 5,225,538 A | 7/1993 | Capon et al. |
| 5,225,539 A | 7/1993 | Winter |
| 5,258,498 A | 11/1993 | Huston et al. |
| 5,314,995 A | 5/1994 | Fell, Jr. et al. |
| 5,349,053 A | 9/1994 | Landolfi |
| 5,359,035 A | 10/1994 | Habermann |
| 5,428,130 A | 6/1995 | Capon et al. |
| 5,441,868 A | 8/1995 | Lin |
| 5,457,038 A | 10/1995 | Trinchieri et al. |
| 5,514,582 A | 5/1996 | Capon et al. |
| 5,538,866 A | 7/1996 | Israeli et al. |
| 5,541,087 A | 7/1996 | Lo et al. |
| 5,543,297 A | 8/1996 | Cromlish et al. |
| 5,547,933 A | 8/1996 | Lin |
| 5,552,524 A | 9/1996 | Basinski et al. |
| 5,585,089 A | 12/1996 | Queen et al. |
| 5,601,819 A * | 2/1997 | Wong et al. |
| 5,609,846 A | 3/1997 | Goldenberg |
| 5,618,698 A | 4/1997 | Lin |
| 5,624,821 A | 4/1997 | Winter et al. |
| 5,639,725 A | 6/1997 | O'Reilly et al. |
| 5,645,835 A | 7/1997 | Fell, Jr. et al. |
| 5,650,150 A | 7/1997 | Gillies |
| 5,650,492 A | 7/1997 | Gately et al. |
| 5,667,776 A | 9/1997 | Zimmerman et al. |
| 5,677,425 A * | 10/1997 | Bodmer et al. .......... 530/387.1 |
| 5,679,543 A | 10/1997 | Lawlis |
| 5,688,679 A | 11/1997 | Powell |
| 5,691,309 A | 11/1997 | Basinski et al. |
| 5,709,859 A | 1/1998 | Aruffo et al. |
| 5,719,266 A | 2/1998 | DiMarchi et al. |
| 5,723,125 A | 3/1998 | Chang et al. |
| 5,726,044 A | 3/1998 | Lo et al. |
| 5,728,552 A | 3/1998 | Fujisawa et al. |
| 5,733,876 A | 3/1998 | O'Reilly et al. |
| 5,756,349 A | 5/1998 | Lin |
| 5,756,461 A | 5/1998 | Stephens |
| 5,759,551 A | 6/1998 | Ladd et al. |
| 5,770,195 A | 6/1998 | Hudziak et al. |
| 5,800,810 A | 9/1998 | Doyle et al. |
| 5,807,715 A | 9/1998 | Morrison et al. |
| 5,827,516 A | 10/1998 | Urban et al. |
| 5,837,682 A | 11/1998 | Folkman et al. |
| 5,843,423 A | 12/1998 | Lyman et al. |
| 5,854,205 A | 12/1998 | O'Reilly et al. |
| 5,856,298 A | 1/1999 | Strickland |
| 5,858,347 A | 1/1999 | Bauer et al. |
| 5,885,795 A | 3/1999 | O'Reilly et al. |

(Continued)

FOREIGN PATENT DOCUMENTS

AU    21725/88    3/1989

(Continued)

OTHER PUBLICATIONS

Cruse et al., Illustrated Dictionary of Immunology, CRC Press, NY, pp. 156-157, 1995.*

(Continued)

*Primary Examiner*—Larry R. Helms
*Assistant Examiner*—Parithosh K. Tungaturthi
(74) *Attorney, Agent, or Firm*—Kirkpatrick & Lockhart Nicholson Graham LLP

(57) ABSTRACT

Disclosed are methods and compositions for efficiently expressing antibody fusion proteins. Antibody fusion proteins of the invention include a hybrid antibody moiety containing sequences from more than one type of antibody and/or mutant antibody sequences. Hybrid antibody fusion proteins of the invention may be produced at high levels and may combine functional properties characteristic of different antibody types in addition to functional properties of a non-antibody moiety.

10 Claims, 4 Drawing Sheets

U.S. PATENT DOCUMENTS

| | | | |
|---|---|---|---|
| 5,886,178 A | 3/1999 | Allen et al. | |
| 5,888,772 A | 3/1999 | Okasinski et al. | |
| 5,891,680 A | 4/1999 | Lieschke et al. | |
| 5,908,626 A | 6/1999 | Chang et al. | |
| 5,922,685 A | 7/1999 | Rakhmilevich et al. | |
| 5,955,422 A | 9/1999 | Lin | |
| 5,994,104 A | 11/1999 | Anderson et al. | |
| 5,994,126 A | 11/1999 | Steinman et al. | |
| 6,080,409 A | 6/2000 | Laus et al. | |
| 6,086,875 A | 7/2000 | Blumberg et al. | |
| 6,100,387 A | 8/2000 | Herrmann et al. | |
| 6,169,070 B1 | 1/2001 | Chen et al. | |
| 6,171,588 B1 | 1/2001 | Carron et al. | |
| 6,231,536 B1 | 5/2001 | Lentz | |
| 6,277,375 B1 | 8/2001 | Ward | |
| 6,284,536 B1 * | 9/2001 | Morrison et al. | |
| 6,335,176 B1 * | 1/2002 | Inglese et al. | 435/7.72 |
| 6,340,742 B1 | 1/2002 | Burg et al. | |
| 6,348,192 B1 | 2/2002 | Chan et al. | |
| 6,406,689 B1 | 6/2002 | Falkenberg et al. | |
| 6,429,199 B1 | 8/2002 | Krieg et al. | |
| 6,444,792 B1 * | 9/2002 | Gray et al. | |
| 6,475,717 B1 | 11/2002 | Enssle et al. | |
| 6,485,726 B1 | 11/2002 | Blumberg et al. | |
| 6,500,641 B1 | 12/2002 | Chen et al. | |
| 6,506,405 B1 | 1/2003 | Desai et al. | |
| 6,551,592 B1 * | 4/2003 | Thierfelder et al. | |
| 6,583,272 B1 | 6/2003 | Bailon | |
| 6,586,398 B1 | 7/2003 | Kinstler et al. | |
| 6,617,135 B1 * | 9/2003 | Gillies et al. | 435/69.7 |
| 6,620,413 B1 * | 9/2003 | DeSauvage et al. | 424/178.1 |
| 6,646,113 B1 | 11/2003 | Dreyfuss et al. | |
| 2001/0053539 A1 | 12/2001 | Lauffer et al. | |
| 2002/0037558 A1 | 3/2002 | Lo et al. | |
| 2002/0081664 A1 | 6/2002 | Lo et al. | |
| 2002/0142374 A1 * | 10/2002 | Gallo et al | |
| 2002/0146388 A1 | 10/2002 | Gillies | |
| 2002/0147311 A1 | 10/2002 | Gillies et al. | |
| 2002/0192222 A1 | 12/2002 | Blumberg et al. | |
| 2002/0193570 A1 | 12/2002 | Gillies et al. | |
| 2003/0003529 A1 | 1/2003 | Bayer | |
| 2003/0012789 A1 | 1/2003 | Blumberg et al. | |
| 2003/0044423 A1 | 3/2003 | Gillies et al. | |
| 2003/0049227 A1 | 3/2003 | Gillies et al. | |
| 2003/0105294 A1 | 6/2003 | Gillies et al. | |
| 2003/0133939 A1 | 7/2003 | Ledbetter et al. | |
| 2003/0139365 A1 | 7/2003 | Lo et al. | |
| 2003/0139575 A1 | 7/2003 | Gillies | |
| 2003/0157054 A1 | 8/2003 | Gillies et al. | |
| 2003/0166163 A1 | 9/2003 | Gillies | |
| 2003/0166877 A1 | 9/2003 | Gillies et al. | |
| 2004/0013640 A1 | 1/2004 | Zardi et al. | |
| 2004/0033210 A1 | 2/2004 | Gillies | |
| 2004/0043457 A1 | 3/2004 | Schumacher et al. | |
| 2004/0053366 A1 | 3/2004 | Lo et al. | |
| 2004/0072299 A1 | 4/2004 | Gillies et al. | |
| 2004/0082039 A1 | 4/2004 | Gillies et al. | |

FOREIGN PATENT DOCUMENTS

| | | |
|---|---|---|
| CN | 93100115.3 | 7/1993 |
| DE | 37 12985 A1 | 11/1988 |
| DE | 37 45985 | 11/1988 |
| EP | 0 158 198 A1 | 10/1985 |
| EP | 0 211 769 A2 | 2/1987 |
| EP | 0 237 019 A2 | 9/1987 |
| EP | 0 256 714 A2 | 2/1988 |
| EP | 0 294 703 A2 | 12/1988 |
| EP | 0 308 936 B1 | 3/1989 |
| EP | 0 314 317 B1 | 5/1989 |
| EP | 0 318 554 B1 | 6/1989 |
| EP | 0 319 012 A2 | 6/1989 |
| EP | 0 326 120 B1 | 8/1989 |
| EP | 0 350 230 A2 | 1/1990 |
| EP | 0 375 562 B1 | 6/1990 |
| EP | 0 396 387 A2 | 11/1990 |
| EP | 0 439 095 A2 | 7/1991 |
| EP | 0 511 747 A1 | 11/1992 |
| EP | 0 519 596 A1 | 12/1992 |
| EP | 0 334 134 B1 | 1/1994 |
| EP | 0 344 134 B1 | 1/1994 |
| EP | 0 601 043 B1 | 6/1994 |
| EP | 0 640 619 A1 | 3/1995 |
| EP | 0 668 353 A1 | 8/1995 |
| EP | 0 428 596 B1 | 4/1996 |
| EP | 0 706 799 A2 | 4/1996 |
| EP | 0 428 267 B1 | 12/1996 |
| EP | 0 790 309 A1 | 8/1997 |
| EP | 0 433 827 B1 | 3/1998 |
| EP | 0 668 351 B1 | 9/1999 |
| EP | 1 088 888 A1 | 4/2001 |
| EP | 0 669 755 B1 | 4/2004 |
| GB | 2 188 638 A | 10/1987 |
| GB | 2 292 382 A | 2/1996 |
| JP | 63-267278 | 11/1988 |
| JP | 63-267296 | 11/1988 |
| WO | WO 86/01533 | 3/1986 |
| WO | WO 88/00052 | 1/1988 |
| WO | WO 88/09344 | 12/1988 |
| WO | WO 89/02922 | 4/1989 |
| WO | WO 89/09620 | 10/1989 |
| WO | WO 90/03801 | 4/1990 |
| WO | OW 91/00360 | 1/1991 |
| WO | WO 91/04329 A1 | 4/1991 |
| WO | WO 91/08298 | 6/1991 |
| WO | WO 91/13166 A1 | 9/1991 |
| WO | WO 91/14438 | 10/1991 |
| WO | WO 92/02240 | 2/1992 |
| WO | WO 92/08495 | 5/1992 |
| WO | WO 92/08801 | 5/1992 |
| WO | WO 92/10755 | 6/1992 |
| WO | WO 92/16562 | 10/1992 |
| WO | WO 93/03157 | 2/1993 |
| WO | WO 93/10229 | 5/1993 |
| WO | WO 93/20185 | 10/1993 |
| WO | WO 94/24160 | 10/1994 |
| WO | WO 94/25055 | 11/1994 |
| WO | WO 94/25609 | 11/1994 |
| WO | WO 95/05468 | 2/1995 |
| WO | WO 95/21258 | 8/1995 |
| WO | WO 95/28427 | 10/1995 |
| WO | WO 95/31483 | 11/1995 |
| WO | WO 96/04388 | 2/1996 |
| WO | WO 96/05309 | 2/1996 |
| WO | WO 96/08570 | 3/1996 |
| WO | WO 96/18412 | 6/1996 |
| WO | WO 96/31526 | 10/1996 |
| WO | WO 96/40792 | 12/1996 |
| WO | WO 97/00317 | 1/1997 |
| WO | WO 97/00319 | 1/1997 |
| WO | WO 97/15666 | 5/1997 |
| WO | WO 97/20062 | 6/1997 |
| WO | WO 97/24137 | 7/1997 |
| WO | WO 97/24440 | 7/1997 |
| WO | WO 97/26335 | 7/1997 |
| WO | WO 97/30089 | 8/1997 |
| WO | WO 97/33617 | 9/1997 |
| WO | WO 97/33619 | 9/1997 |
| WO | WO 97/34631 | 9/1997 |
| WO | WO 97/43316 | 11/1997 |
| WO | WO 98/00127 | 1/1998 |
| WO | WO 98/06752 | 2/1998 |
| WO | WO 98/28427 | 7/1998 |
| WO | WO 98/30706 | 7/1998 |

| | | |
|---|---|---|
| WO | WO 98/46257 | 10/1998 |
| WO | WO 98/52976 | 11/1998 |
| WO | WO 98/59244 | 12/1998 |
| WO | WO 99/02709 * | 1/1999 |
| WO | WO 99/03887 | 1/1999 |
| WO | WO 99/29732 | 6/1999 |
| WO | WO 99/43713 | 9/1999 |
| WO | WO 99/43713 A1 | 9/1999 |
| WO | WO 99/52562 | 10/1999 |
| WO | WO 99/53958 | 10/1999 |
| WO | WO 99/60128 | 11/1999 |
| WO | WO 99/62944 | 12/1999 |
| WO | WO 99/66054 | 12/1999 |
| WO | WO 00/01822 | 1/2000 |
| WO | WO 00/66913 | 1/2000 |
| WO | WO 00/11033 | 3/2000 |
| WO | WO 00/24893 | 5/2000 |
| WO | WO 00/34317 | 6/2000 |
| WO | WO 00/40615 | 7/2000 |
| WO | WO 00/68376 | 11/2000 |
| WO | WO 00/78334 | 12/2000 |
| WO | WO 01/07081 | 2/2001 |
| WO | WO 01/10912 | 2/2001 |
| WO | WO 01/36489 | 5/2001 |
| WO | WO 01/58957 | 8/2001 |
| WO | WO 02/02143 | 1/2002 |
| WO | WO02/056910 A1 | 7/2002 |
| WO | WO 02/066514 | 8/2002 |
| WO | WO 02/072605 | 9/2002 |
| WO | WO02/074783 | 9/2002 |
| WO | WO 02/079232 | 10/2002 |
| WO | WO 02/079415 | 10/2002 |
| WO | WO 00/69913 A1 | 11/2002 |
| WO | WO 02/090566 | 11/2002 |
| WO | WO 03/015697 | 2/2003 |
| WO | WO 03/048334 | 6/2003 |
| WO | WO 03/077834 | 9/2003 |

OTHER PUBLICATIONS

Mueller et al., Molecular Immunology 34:441-452, 1997.*
Cruse et al Illustrated Dictionary of Immunology CRC press, p. 158, 1995.*
Gillies et al. (1999) "Improving the Efficacy of Antibody-Interleukin 2 Fusion Proteins by Reducing Their Interaction with Fc Receptors," Cancer Research, vol. 59, pp. 2159-2166.
Stevenson et al. (1997) "Conjugation of Human Fcγ in Closed-Hinge or Open-Hinge Configuration to Fab'γ and Analogous Ligands," J. of Immunology, vol. 158, pp. 2242-2250.
International Search Report for International Patent Application Serial No. PCT/US02/07011, dated Sep. 18, 2002, 3 pages.
U.S. Appl. No. 07/348,237, filed May 5, 1989, Rosenblum et al.
Abaza et al., (1992), "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin," Journal of Protein Chemistry,11(5):433-444.
Abstract XP-002116766, Lupulescu, (1996), "Prostaglandins, Their Inhibitors and Cancer," Prostaglandins, Leukotrienes and Essential Fatty Acids, 54(2):83-94.
Afonso et al., (1994), "The Adjuvant Effect of Interleukin-12 in a Vaccine Against Leishmania Major," Science, 263:235-237.
Angal et al., (1993), "A Single Amino Acid Substitution Abolishes the Heterogeneity of Chimeric Mouse/Human (lgG4) Antibody," Molecular Immunology, 30(1):105-108.
Arenberg et al., (1996), "Interferon-γ-inducible Protein 10 (IP-10) is an Angiostatic Factor that Inhibits Human Non-small Cell Lung Cancer (NSCLC) Tumorigenesis and Spontaneous Metastases," J. Exp. Med., 184:981-992.
Bacha et al., (1988), "Interleukin 2 Receptor-Targeted Cytotoxicity: Interleukin 2 Receptor-mediated Action of a Diphtheria Toxin-related Interleukin 2 Fusion Protein," J. Exp. Med., 167:612-622.

Bachelot et al., (1998), "Retrovirus-Mediated Gene Transfer of an Angiostatin-Endostatin Fusion Protein with Enhanced Anti-Tumor Properties In Vivo," Proceedings of the Annual Meeting of the American Association for Cancer Research, 39:271, Abstract #1856 (XP-002089298).
Barnett et al., (1994), "Purification, Characterization and Selective Inhibition of Human Prostaglandin G/H Synthase 1 and 2 Expressed in the Baculovirus System," Biochimica et Biophysica Acta, 1209:130-139.
Baselga et al., (1998), "Recombinant Humanized Anti-HER2 Antibody (Herceptin™) Enhances the Antitumor Activity of Paclitaxel and Doxorubicin against HER3/neu Overexpressing Human Breast Cancer Xenografts," Cancer Research, 58:2825-2831.
Batova et al., (1999), "The Ch14.18-GM-CSF Fusion Protein Is Effective at Mediating Antibody-dependent Cellular Cytotoxicity and Complement-dependent Cytotoxicity in Vitro," Clinical Cancer Research, 5:4259-4263.
Batra et al., (1993), "Insertion of Constant Region Domains of Human IgG1 into CD4-PE40 Increases Its Plasma Half-Life," Molecular Immunology, 30(4):379-386.
Becker et al., (1996), "An Antibody-Interleukin 2 Fusion Protein Overcomes Tumor Heterogeneity by Induction of a Cellular Immune Response," Proc. Natl. Acad. Sci. USA, 93:7826-7831.
Becker et al., (1996), "Eradication of Human Hepatic and Pulmonary Melanoma Metastases in SCID Mice by Antibody-interleukin 2 Fusion Proteins," Proc. Natl. Acad. Sci. USA, 93:2702-2707.
Becker et al., (1996), "Long-lived and Transferable Tumor Immunity in Mice after Targeted Interleukin-2 Therapy," J. Clin. Invest., 98(12):2801-2804.
Becker et al., (1996), "T Cell-mediated Eradication of Murine Metastatic Melanoma Induced by Targeted Interleukin-2 Therapy," J. Exp. Med., 183(50):2361-2366.
Beutler et al., (1988), "Tumor Necrosis, Cachexia, Shock, and Inflammation: A Common Mediator," Annual Rev. Biochem., 57:505-518.
Bissery et al., (1997), "The Taxoids," in Cancer Therapeutics: Experimental and Clinical Agents, Teicher (ed.), pp. 175-193.
Bitonti et al., (2002), "Transepithelial Absorption of an Erythropoietin-Fe Fusion Protein After Delivery to the Central Airways," Respiratory Drug Delivery, 8:309-312.
Bjorn et al., (1985), "Evaluation of Monoclonal Antibodies for the Development of Breast Cancer Immunotoxins," Cancer Research, 45:1214-1221.
Boehm et al., (1997), "Antiangiogenic Therapy of Experimental Cancer Does Not Induce Acquired Drug Resistance," Nature, 390:404-407.
Boehm et al., (1998), "Zinc-Binding of Endostatin Is Essential for Its Antiangiogenic Activity," Biochemical and Biophysical Research Communications, 252:190-194.
Boissel et al., (1993), "Erythropoietin Structure-Function Relationships: Mutant Proteins that Test a Model of Tertiary Structure," The Journal of Biological Chemistry, 268(21):15983-15993.
Briggs et al., (1974), "Hepatic Clearance of Intact and Desialylated Erythropoietin," American Journal of Physiology, 227(6):1385-1388.
Brooks et al., (1994), "Integrin $\alpha_v\beta_3$ Antagonists Promote Tumor Regression by Inducing Apoptosis of Angiogenic Blood Vessels," Cell, 79:1157-1164.
Buchli et al., (1993), "Structural and Biologic Properties of a Human Aspartic Acid-126 Interleukin-2 Analog," Archives of Biochemistry and Biophysics, 307(2):411-415.
Burgess et al., (1990), "Possible Dissociation of the Heparin-binding and Mitogenic Activities of Heparin-Binding (Acidic Fibroblast) Growth Factor-1 from Its Receptor-binding Activities by Site-directed Mutagenesis of a Single Lysine Residue," Journal of Cell Biology, 111:2129-2138.
Canfield et al., (1991), "The Binding Affinity of Human IgG for its High Affinity Fc Receptor is Determined by Multiple Amino Acids in the CH2 Domain and Is Modulated by the Hinge Region," J. Exp. Med., 173(6):1483-1491.
Cao et al., (1996), "Kringle Domains of Human Angiostatin: Characterization of the Anti-Proliferative Activity of Endothelial Cells," The Journal of Biological Chemistry, 271(46):29461-29467.

Cao et al., (1997), "Kringle 5 of Plasminogen is a Novel Inhibitor of Endothelial Cell Growth," *The Journal of Biological Chemistry*, 272(36):22924-22928.

Capon et al., (1989), "Designing CD4 Immunoadhesins for AIDS Therapy," *Nature*, 337:525-531.

Caton et al., (1986), "Structural and Functional Implications of a Restricted Antibody Response to a Defined Antigenic Region on the Influenza Virus Hemagglutinin," *The EMBO Journal*, 5(7):1577-1587.

Chan et al., (1991), "Induction of Interferon γ Production by Natural Killer Cell Stimulatory Factor: Characterization of the Responder Cells and Synergy with Other Inducers," *J. Exp. Med.*, 173:869-879.

Chang et al., (1989), "Overview of Interleukin-2 as an Immunotherapeutic Agent," *Seminars in Surgical Oncology*, 5:385-390.

Chang et al., (1996), "A Point Mutation in Interleukin-2 that Alters Ligand Internalization, " *Journal of Biological Chemistry*, 27(23):13349-13355.

Chaudhary et al., (1988), "Selective Killing of HIV-infected Cells by Recombinant Human CD4-*Pseudomonas* Exotoxin Hybrid Protein," *Nature*, 335:370-372.

Chaudhary et al., (1989), "A Recombinant Immunotoxin Consisting of Two Antibody Variable Domains Fused to *Pseudomonas* Exotoxin," *Nature*, 339:394-397.

Chen et al., (1997), "Eradication of Murine Bladder Carcinoma by Intratumor Injection of a Bicistronic Adenoviral Vector Carrying cDNAs for the IL-12 Heterodimer and Its Inhibition by the IL-12 p40 Subunit Homodimer," *Journal of Immunology*, 159(1):351-358.

Cheon et al., (1994), "High-affinity Binding Sites for Related Fibroblast Growth Factor Ligands Reside Within Different Receptor Immunoglobulin-like Domains," *Proc. Natl. Acad. Sci. USA*, 91: 989-993.

Chuang et al., (1993), "Effect of New Investigational Drug Taxol on Oncolytic Activity and Stimulation of Human Lymphocytes," *Gynecologic Oncology*, 49:291-298.

Chuang et al., (1994), "Alteration of Lymphocyte Microtubule Assembly, Cytotoxicity, and Activation by the Anticancer Drug Taxol," *Cancer Research*, 54:1286-1291.

Cohen et al., (1996), "Human Leptin Characterization," *Nature*, 382:589.

Cole et al., (1997), "Human IgG2 Variants of Chimeric Anti-CD3 Are Nonmitogenic to T Cells," *Journal of Immunology*, 159:3613-3621.

Collins et al., (1988), "Identification of Specific Residues of Human Interleukin 2 That Affect Binding to the 70-kDa Subunit (p70) of the Interleukin 2 Receptor," *Proc. Natl. Acad. Sci. USA*, 85:7709-7713.

Colombo et al., (1996), "Amount of Interleukin 12 Available at the Tumor Site is Critical for Tumor Regression," *Cancer Research*, 56:2531-2534.

D'Amato et al., (1994), "Thalidomide is an Inhibitor of Angiogenesis," *Proc. Natl. Acad. Sci. USA*, 91:4082-4085.

D'Andrea et al., (1992), "Production of Natural Killer Cell Stimulatory Factor (Interleukin 12) by Peripheral Blood Mononuclear Cells," *J. Exp. Med.*, 176:1387-1398.

Darling et al., (2002), "Glycosylation of Erythropoietin Affects Receptor Binding Kinetics: Role of Electrostatic Interactions," *Biochemistry*, 41:14524-14531.

Davis et al., (2003), "Immunocytokines: Amplification of Anticancer Immunity," *Cancer Immunol. Immunother.*, 52:297-308.

Ding et al., (1988), "Zinc-Dependent Dimers Observed in Crystals of Human Endostatin," *Proc. Natl. Acad. Sci. USA*, 95:10443-10448.

Dolman et al., (1998), "Suppression of Human Prostate Carcinoma Metastases in Severe Combined Immunodeficient Mice by Interleukin 2 Immunocytokine Therapy," *Clin. Cancer Research.*, 4(10):2551-2557.

Duncan et al., (1988), "The Binding Site for C1q on IgG," *Nature*, 332:738-740.

Earnest et al., (1992), "Piroxicam and Other Cyclooxygenase Inhibitors: Potential for Cancer Chemoprevention," *J. Cell. Biochem., Supp.*, 161:156-166.

Egrie et al., (2001), "Development and Characterization of Novel Erythropoiesis Stimulating Protein (NESP)," *Nephrol. Dial. Transplant.*, 16(Supp 3):3-13.

Eisenthal, (1990), "Indomethacin Up-regulates the Generation of Lymphokine-Activated Killer-cell Activity and Antibody-dependent Cellular Cytotoxicity Mediated by Interleukin-2," *Cancer Immunol. Immunother.*, 31:342-348.

Elliott et al., (1997), "Mapping of the Active Site of Recombinant Human Erythropoietin," *Blood*, 89(2):493-502.

Fell et al., (1991), "Genetic Construction and Characterization of A Fusion Protein Consisting of a Chimeric F(ab') with Specificity for Carcinomas and Human IL-2," *J. Immunology*, 146(7):2446-2452.

Fell et al., (1992), "Chimeric L6 Anti-tumor Antibody: Genomic Construction, Expression, and Characterization of the Antigen Binding Site," *J. Biological Chemistry*, 267:15552-15558.

Fibi et al., (1995), "N- and O-Glycosylation Muteins of Recombinant Human Erythropoietin Secreted From BHK-21 Cells," *Blood*, 85(5):1229-1236.

Friedman et al., (1998), "Leptin and the Regulation of Body Weight in Mammals," *Nature*, 395:763-770.

Frost et al., (1997), "A Phase I/IB Trial of Murine Monoclonal Anti-GD2 Antibody 14.G2a Plus Interleukin-2 in Children with Refractory Neuroblastoma," *Cancer*, 80(2):317-333.

Gan et al., (1999), "Specific Enzyme-linked Immunosorbent Assays for Quantitation of Antibody-cytokine Fusion Proteins," *Clinical and Diagnostic Laboratory Immunology*, 6(2):236-42.

Gasson et al., (1984), "Purified Human Granulocyte Macrophage Colony-Stimulating Factor: Direct Action on Neutrophils," *Science*, 226:1339-1342.

Gately et al., (1998), "The Interleukin-12/Interleukin-12-Receptor System: Role in Normal and Pathologic Immune Responses," *Annu. Rev. Immunol.*, 16:495-521.

Gillessen et al., (1995), "Mouse Interleukin-12 (IL-12) p40 Homodimer: A Potent IL-12 Antagonist," *Eur. J. Immunol.*, 25:200-206.

Gillies et al., (1989), "Expression of Human Anti-Tentanus Toxoid Antibody in Transfected Murine Myeloma Cells," *Bio/Technology*, 7:799-804.

Gillies et al., (1989), "High-Level Expression of Chimeric Antibodies Using Adapted cDNA Variable Region Cassettes," *J. Immunol. Methods*, 125:191-202.

Gillies et al., (1990), "Antigen Binding and Biological Activities of Engineered Mutant Chimeric Antibodies with Human Tumor Specificities," *Hum. Antibod. Hybridomas*, 1(1):47-54.

Gillies et al., (1991), "Expression of Genetically Engineered Immunoconjugates of Lymphotoxin and a Chimeric Antiganglioside GD2 Antibody," *Hybridoma.*, 10(3):347-356.

Gillies et al., (1992), "Antibody-Targeted Interleukin 2 Stimulates T-Cell Killing of Autologous Tumor Cells," *Proc. Natl. Acad. Sci. USA*, 98:1428-1432.

Gillies et al., (1993), "Biological Activity and In Vivo Clearance of Antitumor Antibody/Cytokine Fusion Proteins," *Bioconjugate Chem.*, 4(3):230-235.

Gillies et al., (1998), "Antibody-IL-12 Fusion Proteins are Effective in SCID Mouse Models of Prostate and Colon Carcinoma Metastases," *J. Immunology*, 160:6195-6203.

Gillies et al., (2002), "Bi-functional Cytokine Fusion Proteins for Gene Therapy and Antibody-targeted Treatment of Cancer," *Cancer Immunol. Immunother.*, 51(8):449-60.

Gillies et al., (2002), "Improved Circulating Half-life and Efficacy of an Antibody-interleukin 2 Immunocytokine Based on Reduced Intracellular Proteolysis," *Clin. Cancer Research*, 8(1):210-216.

Gillis et al., (1978), "T Cell Growth Factor: Parameters of Production And A Quantitative Microassay for Activity," *J. Immunology*, 120(6):2027-2032.

Goeddel et al., (1986), "Tumor Necrosis Factors: Gene Structure and Biological Activities," *Cold Spring Harb. Symp. Quant. Biol.*, 51:597-609.

Greene et al., (1975), "Neuronal Properties of Hybrid Neuroblastoma X Sympathetic Ganglion Cells," *Proc. Natl. Sci. USA*, 72(12):4923-4927.

Gren et al., (1983), "A New Type of Leukocytic Interferon," English Translation of *Dokl. Akad. Nauk. SSSR.*, 269(4):986-990.

Griffon-Etienne et al., (1999), "Taxane-induced Apoptosis Decompresses Blood Vessels and Lowers Interstitial Fluid Pressure in Solid Tumors: Clinical Implications," *Cancer Research*, 59:3776-3782.

Grimaldi et al., (1989), "The t(5;14) Chromosomal Translocation in a Case of Acute Lymphocytic Leukemia Joins the Interleukin-3 Gene to the Immunoglobulin Heavy Chain Gene," *Blood*, 73(8):2081-2085.

Guyre et al., (1997), "Increased Potency of Fc-receptor-targeted Antigens," *Cancer Immunol. Immunother.*, 45:146-148.

Hammerling et al., (1996), "In Vitro Bioassay for Human Erythropoietin Based on Proliferative Stimulation of an Erythroid Cell Line and Analysis of Carbohydrate-dependent Microheterogeneity," *Journal of Pharmaceutical and Biomedical Analysis*, 14:1455-1469.

Hank et al., (1996), "Activation of Human Effector Cells by a Tumor Reactive Recombinant Anti-ganglioside GD2 Interleukin-2 Fusion Protein (ch.14.18-IL2)," *Clin Cancer Research*, 2(12):1951-1959.

Hank et al., (2003), "Determination of Peak Scrum Levels and Immune Response to the Humanized Anti-ganglioside Antibody-interleukin-2 Immunocytokine," in *Methods in Molecular Medicine, vol. 85: Novel Anticancer Drug Protocols*, Buolamwini et al., (eds.), pp. 123-131, Humana Press Inc., Totowana, NJ.

Haraguchi, (1994), "Isolation of GD3 Synthase Gene by Expression Cloning of GM3 α-2,9-sialyltransferase cDNA using anti-GD2 Monoclonal Antibody," *Proc. Natl. Acad. Sci. USA*, 91(22):10455-10459.

Harris et al., (1993), "Therapeutic Antibodies—the Coming of Age," *Trends in Biotechnology*, 11:42-44.

Harris, (1995), "Processing of C-terminal Lysine and Arginine Residues of Proteins Isolated from Mammalian Cell Culture," *J. Chromatography A*, 705:129-134.

Harvill et al., (1995), "An IgG3-IL2 Fusion Protein Activates Complement, Binds FcγRI, Generates LAK Activity and Shows Enhanced Binding to the High Affinity IL-2R," *Immunotechnology*, 1:95-105.

Harvill et al., (1996), "In Vivo Properties of an IgG3-IL-2 Fusion Protein: A General Strategy for Immune Potentiation," *J. Immunology*, 157(7):3165-3170.

Hazama et al., (1993), "Adjuvant-Independent Enhanced Immune Responses to Recombinant Herpes Simplex Virus Type 1 Glycoprotein D by Fusion with Biologically Active Interleukin-2," *Vaccine*, 11(6):629-636.

He et al., (1998), "Humanization and Pharmacokinetics of a Monoclonal Antibody with Specificity for Both E- and P-Selectin," *J. Immunology*, 160:1029-1035.

Heijnen et al., (1996), "Antigen Targeting to Myeloid-specific Human FcγRI/CD64 Triggers Enhanced Antibody Responses in Transgenic Mice," *J. Clin. Invest.*, 97(2):331-338.

Heinzel et al., (1997), "In Vivo Production and Function of IL-12 p40 Homodimers," *J. Immunology*, 158:4381-4388.

Hellstrom et al., (1986), "Antitumor Effects of L6, an IgG2a Antibody that Reacts with Most Human Carcinomas," *Proc. Natl. Acad. Sci. USA*, 83: 7059-7063.

Henkart, (1985), "Mechanism of Lymphocyte-Mediated Cytotoxicity," *Ann. Rev. Immunol.*, 3:31-58.

Herrmann et al., (1989), "Hematopoietic Responses With Advanced Malignancy Treated With Recombinant Human Granulocyte-Macrophage Colony-Stimulating Factor," *Journal of Clinical Oncology*, 7(2):159-167.

Hezarch et al., (2001), "Effector Function Activities of a Panel of Mutants of a Broadly Neutralizing Antibody against Human Immunodeficiency Virus Type 1," *J. Virology*, 75(24):12161-12168.

Hohenester et al., (1998), "Crystal Structure of the Angiogenesis Inhibitor Endostatin at 1.5 Å Resolution," *EMBO Journal*, 17(6):1656-1664.

Holden et al., (2001), "Augmentation of Anti-Tumor Activity of KS-IL2 Immunocytokine with Chemotherapeutic Agents,"*Proceedings of the American Association for Cancer Research*, 42:683, Abstract No. 3675 (XP-002195344).

Holden et al., (2001), "Augmentation of Antitumor Activity of an Antibody-Interleukin 2 Immunocytokine with Chemotherapeutic Agents," *Clinical Cancer Research*, 7:2862-2869.

Hoogenboom et al., (1991), "Construction and Expression of Antibody-tumor Necrosis Factor Fusion Proteins," *Molecular Immunology*, 28(9):1027-1037.

Hoogenboom et al., (1991), "Targeting of Tumor Necrosis Factor to Tumor Cells Secretion by Myeloma Cells of a Genetically Engineered Antibody-Tumor Necrosis Factor Hybrid Molecule," *Biochim. and Biophys. Acta*, 1096(4):345-354 (Abstract).

Hornick et al., (1999), "Pretreatment with a Monoclonal Antibody/Interleukin-2 Fusion Protein Directed Against DNA Enhances the Delivery of Therapeutic Molecules to Solid Tumors," *Clin. Cancer Research*, 5:51-60.

Hu et al., (1996), "A Chimeric Lym-1/Interleukin 2 Fusion Protein for Increasing Tumor Vascular Permeability And Enhancing Antibody Uptake," *Cancer Research*, 56:4998-5004.

Huck et al., (1986), "Sequence of a Human Immunoglobulin Gamma 3 Heavy Chain Constant Region Gene: Comparison With the Other Human Cγ genes," *Nucleic Acids Research*, 14(4):1779-1789.

Huse et al., (1989), "Generation of a Large Combinatorial Library of the Immunoglobulin Repertoire in Phage Lambda," *Science*, 246:1275-1281.

Idusogie et al., (2000), "Mapping of the C1q Binding Site on Rituxan, a Chimeric Antibody with a Human IgG1 Fc," *J. Immunology*, 164(8):4178-4184.

Imboden et al., (2001), "The Level of MHC Class I Expression on Murine Adenocarcinoma Can Change the Antitumor Effector Mechanism of Immunocytokine Therapy," *Cancer Research*, 61(4):1500-7.

Ingber et al., (1990), "Synthetic Analogues of Fumagillin that Inhibit Angiogenesis and Suppress Tumour Growth," *Nature*, 348:555-557.

Jones et al., (1986), "Replacing the Complementarity-determining Regions in a Human Antibody with Those from a Mouse," *Nature*, 321:522-525.

Ju et al., (1987), "Structure-Function Analysis of Human Interleukin-2: Indetification of Amino Acid Residues for Biological Activity," *Journal of Biological Chemistry*, 262(12):5723-5731.

Jung et al., (1986), "Activation of Human Peripheral Blood Mononuclear Cells by Anti-T3: Killing of Tumor Target Cells Coated with Anti-target-anti-T3 Conjugates," *Proc. Natl. Acad. Sci. USA*, 83:4479-4483.

Junghans et al., (1996), "The Protection Receptor of IgG Catabolism is the B2-microglobulin-containing Neonatal Intestinal Transport Receptor," *Proc. Natl. Acad. Sci. USA*, 93(11):5512-5516.

Kang et al., (1991), "Antibody Redesign by Chain Shuffling from Random Combinatorial Immunoglobulin Libraries," *Proc. Natl. Acad. Sci. USA*, 88:11120-11123.

Kappel et al., (1992), "Regulating Gene Expression in Transgenic Animals," *Current Opinion in Biotechnology*, 3:548-553.

Kato et al., (1997), "Mechanism for the Nonlinear Pharmacokinetics of Erythropoietin in Rats," *The Journal of Pharmacology and Experimental Therapeutics*,283:520-527.

Kato et al., (1998), "Pharmacokinetics of Erythopoietin in Genetically Anemic Mice," *Drug Metabolism and Disposition*, 26(2):126-131.

Karpovsky et al., (1984), "Production of Target-Specific Effector Cells using Hetero-Cross Linked Aggregate Containing Anti-Target Cell and AntiFcγ receptor Antibodies," *Journal of Experimental Medicine*, 1609(6):1686-1701.

Kendra et al., (1999), "Pharmacokinetics and Stability of the ch14.18-Interleukin-2 Fusion Protein in Mice," *Cancer Immunol. Immunother.*, 48:219-229.

Kim et al., (1997), "An Ovalbumin-IL-12 Fusion Protein is More Effective than Ovalbumin Plus Free Recombinant IL-12 in Inducing a T Helper Cell Type 1-dominated Immune Response and Inhibiting Antigen-Specific IgE Production," *J. Immunology*, 158(9):4137-4144.

Kim et al., (1999), "Cytokine Molecular Adjuvants Modulate Immune Responses Induced by DNA Vaccine Cosntructs for HIV-1 and SIV," *Journal of Interferon and Cytokine Research*, 19:77-84.

Kitamura et al., (1989), "Establishment and Characterization of a Unique Human Cell Line that Proliferates Dependently on GM-CSF, IL-3, or Erythropoietin," *Journal of Cellular Physiology*, 140:323-334.

Kranz et al.,( 1984), "Attachment of an Anti-receptor Antibody to Non-target Cells Renders Them Susceptible to Lysis by a Clone of Cytotoxic T Lymphocytes," *Proc. Natl. Acad. Sci. USA*, 81:7922-7926.

Kuo et al., (2001), "Oligomerization-dependent Regulation of Motility and Morphogenesis by the Collagen XVIII NCI/Endostatin Domain," *Journal of Cell Biology*, 152(6):1233-1246.

Kushner et al., (2001), "Phase II Trial of the Anti-GD2 Monoclonal Antibody 3F8 and Granulocyte-Macrophage Colony-Stimulating Factor for Neuroblastoma," *J. Clinical Oncology*, 19(22):4189-94.

LaVallie et al., (1993), "Cloning and Functional Expression of a cDNA Encoding the Catalytic Subunit of Bovine Enterokinase," *Journal of Biological Chemistry*, 268(31):23311-23317.

Lazar et al., (1988), "Transforming Growth Factor α Mutation of Aspartic Acid 47 and Leucine 48 Results in Different Biological Activities," *Molecular and Cellular Biology*, 8(3):1247-1252.

LeBerthon et al., (1991), "Enhanced Tumor Uptake of Macromolecules Induced by a Novel Vasoactive Interleukin 2 Immunoconjugate," *Cancer Research*, 51:2694-2698.

Lieschke, et al., (1997), "Bioactive Murine and Human Interleukin-12 Fusion Proteins which Retain Antitumor Activity In Vivo," *Nature Biotechnology*, 15(1):35-40.

Linsley et al., (1991), "CTLA-4 is a Second Receptor for B Cell Activation Antigen B7," *J. Exp. Med.*, 174(3):561-569.

Liu et al., (1985), "Heteroantibody Duplexes Target Cells for Lysis by Cytotoxic T Lymphocytes," *Proc. Natl. Acad. Sci. USA*, 82:8648-8652.

Liu et al., (1988), "Hormone Conjugated with Antibody to CD3 Mediates Cytotoxic T Cell Lysis of Human Melanoma Cells," *Science*, 239:395-398.

Liu et al., (1998), "Immunostimulatory CpG Oligodeoxynucleotides Enhance the Immune Response to Vaccine Strategies Involving Granulocyte-Macrophage Colony-Stimulating Factor," *Blood*,92(10):3730-3736.

Lo et al., (1998), "High Level Expression and Secretion of Fc-X Fusion Proteins in Mammalian Cells," *Protein Engineering*, 11(6):495-500.

Locatelli et al., (2001), "Darbepoetin alfa Amgen," *Current Opinion in Investigational Drugs*, 2:1097-1104.

Lode et al., (1997), "Targeted Interleukin-2 Therapy for Spontaneous Neuroblastoma Metastases to Bone Marrow," *J. Natl. Cancer Inst.*, 89(21):1586-94.

Lode et al., (1998), "Immunocytokines: A Promising Approach to Cancer Immunotherapy," *Pharmacol. Ther.*, 80(3):277-292.

Lode et al., (1998), "Natural Killer Cell-Mediated Eradication of Neuroblastoma Metastases to Bone Marrow by Targeted Interleukin-2 Therapy," *Blood*, 91(5):1706-1715.

Lode et al., (1999), "Synergy Between an Antiangiogenic Integrin $\gamma_v$ Antagonist and an Antibody-cytokine Fusion Protein Eradicates Spontaneous Tumor Metastases," *Proc. Natl. Acad. Sci. USA*, 96:1591-1596.

Lode et al., (1999), "Tumor-targeted IL-2 Amplifies T Cell-mediated Immune Response Induced by Gene Therapy with Single-chain IL-12," *Proc. Natl. Acad. Sci. USA*, 96:8591-8596.

Lode et al., (2000), "Amplification of T Cell Mediated Immune Responses by Antibody-Cytokine Fusion Proteins," *Immunological Investigations*, 29(2):117-120.

Lode et al., (2000), "What To Do With Targeted IL-2," *Drugs of Today*, 36(5):321-336.

Lode et al., (2000), "Melanoma Immunotherapy by Targeted IL-2 Depends on CD4(+) T-cell Help Mediated by CD40/CD40L Interaction," *J. Clin. Invest.*, 105(11):1623-30.

Macdougall, (2002), "Optimizing the Use of Erythropoietic Agents—Pharmacokinetic and Pharmacodynamic Considerations," *Nephrol. Dial. Transplant.*, 17(Supp 5):66-70.

Maloney et al., (1994), "Phase I Clinical Trial Using Escalating Single-Dose Infusion of Chimeric Anti-CD20 Monoclonal Antibody (IDEC-C2B8) in Patients with Recurrent B-Cell Lymphoma," *Blood*, 84(8):2457-2466.

Mark et al., (1992), "Expression and Characterization of Hepatocyte Growth Factor Receptor-IgG Fusion Proteins," *Journal of Biological Chemistry*, 267(36):26166-26171.

Martinotti et al., (1995), "CD4 T Cells Inhibit *In Vivo* the CD8-Mediated Immune Response Against Murine Colon Carcinoma Cells Transduced with Interleukin-12 Genes," *Eur. J. Immunol.* 25:137-146.

Medesan et al., (1997), "Delineation of the Amino Acid Residues Involved in Transcytosis and Catabolism of Mouse IgG1," *J. Immunology*, 158(5):2211-2217.

Metelitsa et al., (2002), "Antidisialoganglioside/granulocyte Macrophage-colony-stimulating Factor Fusion Protein Facilitates Neutrophil Antibody-dependent Cellular Cytotoxicity and Depends on FcγRII (CD32) and Mac-1 (CD11b/CD18) for Enhanced Effector Cell Adhesion and Azurophil Granule Exocytosis," *Blood*, 99(11):4166-73.

Mestre et al., (1997), "Retinoids Suppress Epidermal Growth Factor-induced Transcription of Cyclooxygenase-2 in Human Oral Squamous Carcinoma Cells," *Cancer Research*, 57:2890-2895.

Mosmann et al., (1989), "TH1 and TH2 Cells: Different Patterns of Lymphokine Secretion Lead to Different Functional Properties," *Ann. Rev. Immunol.*, 7:145-173.

Mott et al., (1995), "The Solution Structure of the F42A Mutant of Human Interleukin 2," *J. Mol. Biol.*, 247:979-994.

Mullins et al., (1997), "Taxol-mediated Changes in Fibrosarcoma-induced Immune Cell Function: Modulation of Antitumor Activities," *Cancer Immunol. Immunother* , 45:20-28.

Mullins et al., (1998), "Interleukin-12 Overcomes Paclitaxel-mediated Suppression of T-cell Proliferation," *Immunopharmacol. Immunotoxicol.*, 20(4):473-492.

Murphy et al., (1986), "Genetic Construction, Expression, and Melanoma-selective Cytotoxicity of a Diphtheria Toxin-related α-melanocyte-stimulating Hormone Fusion Protein," *Proc. Natl. Acad. Sci. USA*, 83:8258-8262.

Murphy, (1988), "Diphtheria-related Peptide Hormone Gene Fusions: A Molecular Gene Approach to Chimeric Toxin Development," in *Immunotoxins*, pp. 123-140, Frankel (ed.), Kluwer Acad. Pub.

Naramura et al., (1994), "Mechanisms of Cellular Cytotoxicity Mediated by a Recombinant Antibody-IL2 Fusion Protein Against Human Melanoma Cells," *Immunology Letters*, 39:91-99.

Neal et al., (2003), "NXS2 Murine Neuroblastomas Express Increased Levels of MHC Class I Antigens upon Recurrence Following NK-dependent Immunotherapy," *Cancer Immunol. Immunother.*, 53:41-52.

Nedwin et al., (1985), "Human Lymphotoxin and Tumor Necrosis Factor Genes: Structure, Homology and Chromosomal Localization," *Nucleic Acids Research*, 13(17):6361-6373.

Netti et al., (1995), "Time-dependent Behavior of Interstitial Fluid Pressure in Solid Tumors: Implications for Drug Delivery," *Cancer Research*, 55:5451-5458.

Netti et al., (1999), "Enhancement of Fluid Filtration Across Tumor Vessels: Implication for Delivery of Macromolecules," *Proc. Nat. Acad. Sci. USA* , 96:3137-3142.

Neuberger et al., (1984), "Recombinant Antibodies Possessing Novel Effector Functions," *Nature*, 312:604-608.

Ngo et al., (1994), "Computational Complexity, Protein Structure Prediction, and the Levinthal Paradox," in *The Protein Folding Problem and Tertiary Structure Prediction*, Merz et al. (eds.), pp. 433-440 and 492-495, Birkhauser, Boston, MA.

Niethammer et al., (2002) "An Oral DNA Vaccine Against Human Carcinoembryonic Antigen (CEA) Prevents Growth and Dissemination of Lewis Lung Carcinoma in CEA Transgenic Mice," *Vaccine*, 20:421-429.

Niethammer et al., (2001) "Targeted Interleukin 2 Therapy Enhances Protective Immunity Induced by an Autologous Oral DNA Vaccine against Murine Melanoma," *Cancer Research*, 61(16):6178-84.

Nimtz et al., (1993), "Structures of Sialylated Oligosaccharides of Human Erythropoietin Expressed in Recombinant BHK-21 Cells," *Eur. J. Biochem.*, 213:39-56.

O'Reilly et al., (1994), "Angiostatin: A Novel Angiogenesis Inhibitor That Mediates the Suppresion of Metastases by a Lewis Lung Carcinoma," *Cell*, 79:315-328.

O'Reilly et al., (1996), "Angiostatin Induces and Sustains Dormancy of Human Primary Tumors in Mice," *Nature Medicine*, 2(6):689-692.

O'Reilly et al., (1997), "Endostatin: An Edogenous Inhibitor of Angiogenesis and Tumor Growth," *Cell*, 88:277-285.

Pancook et al., (1996), "Eradication Established Hepatic Human Neuroblastoma Metastases in Mice with Severe Combined Immunodeficiency by Antibody-targeted Interleukin-2," *Cancer Immunol. Immunother.*, 42(2):88-92.

Park et al., (2000), "Efficiency of Promoter and Cell Line in High-level Expression of Erythropoietin," *Biotechnol. Appl. Biochem.*, 32:167-172.

Pastan et al., (1989), "*Pseudomonas* Exotoxin: Chimeric Toxins," *Journal of Biological Chemistry*, 264(26):15157-15160.

Paul et al., (1988), "Lymphotoxin," *Ann. Rev. Immunol.*, 6:407-438.

Perez et al., (1986), "Specific Targeting of Human Peripheral Blood T Cells by Heteroaggregates Containing Anti-T3 Crosslinked to Anti-Target Cell Antibodies," *J. Exp. Med.*, 163:166-178.

Perez et al., (1989), "Isolation and Characterization of a cDNA Encoding the KS1/4 Epithelial Carcinoma Marker," *J. Immunology*, 142(10):3662-3667.

Polizzi et al., (1999), "A Novel Taxane with Improved Tolerability and Therapeutic Activity in a Panel of Human Tumor Xenografts," *Cancer Research*, 59:1036-1040.

Putzer et al., (1997), "Interleukin 12 and B7-1 Costimulatory Molecule Expressed by an Adenovirus Vector Act Synergistically to Facilitate Tumor Regression," *Proc. Natl. Acad. Sci. USA*, 94(20):10889-10894.

Reisfeld et al., (1996), "Antibody-interleukin 2 Fusion Proteins: A New Approach to Cancer Therapy," *J. Clin. Lab. Anal.*, 10:160-166.

Reisfeld et al., (1996), "Involvement of B Lymphocytes in the Growth Inhibition of Human Pulmonary Melanoma Metastases in Athymic nu/nu Mice by an Antibody-lymphotoxin Fusion Protein," *Cancer Research*, 56(8):1707-1712.

Reisfeld et al., (1996), "Recombinant Antibody Fusion Proteins for Cancer Immunotherapy," *Current Topics in Microbiology and Immunology*, 213:27-53.

Reisfeld et al., (1997), "Immunocytokines: A New Approach to Immunotherapy of Melanoma," *Melanoma Research*, 7(Supp2):S99-S106.

Riethmuller et al., (1994), "Randomised Trial of Monoclonal Antibody for Adjuvant Therapy of Resected Dukes'C Colorectal Carcinoma," *The Lancet*, 343:1177-1183.

Roessler et al., (1994), "Cooperative Interactions Between the Interleukin 2 Receptor α and β Chains Alter the Interleukin 2-binding Affinity of the Receptor Subunits," *Proc. Natl. Acad. Sci. USA*, 91:3344-3347.

Roitt et al., (1993), "The Role of TH Cells in the Selection of Effector Mechanisms Directed Against Target Antigens," *Immunology*, 3rd Ed., pp. 8.3-8.4.

Rosenberg, (1988), "Immunotherapy of Cancer Using Interleukin 2: Current Status and Future Prospects," *Immunology Today*, 9(2):58-62.

Rozwarski et al., (1994), "Structural Comparisons Among the Short-chain Helical Cytokines," *Structure*, 2(3):159-173.

Ruehlmann et al., (2001), "MIG (CIXCL9) Chemokine Gene Therapy Combines with Antibody-cytokine Fusion Protein to Supress Growth and Dissemination of Murine Colon Carcinoma," *Cancer Research*, 61(23):8498-503.

Sabzevari et al., (1994), "A Recombinant Antibody-interleukin 2 Fusion Protein Suppresses Growth of Hepatic Human Severe Combined Immunodeficiency Mice," *Proc. Natl. Acad. Sci. USA*, 91(20):9626-30.

Santon et al., (1986), "Effects of Epidermal Growth Factor Receptor Concentration on Tumorigenicity of A431 Cells in Nude Mice," *Cancer Research*, 46:4701-4705.

Sasaki et al., (1998), "Structure, Function and Tissue Forms of the C-terminal Globular Domain of Collagen XVIII Containing the Angiogenesis Inhibitor Endostatin," *EMBO Journal*, 17(15):4249-4256.

Sauve et al., (1991), "Localization in Human Interleukin 2 of the Binding Site to the α-chain (p55) of the Interleukin 2 Receptor," *Proc. Natl. Acad. Sci. USA*, 88:4636-4640.

Schnee et al., (1987), "Construction and Expression of a Recombinant Antibody-targeted Plasminogen Activator," *Proc. Natl. Acad. Sci. USA*, 84:6904-6908.

Schoenhaut et al., (1992), "Cloning and Expression of Murine IL-12," *J. Immunology*, 148(11):3433-3340.

Seidenfeld et al., (2001), "Epoietin Treatment of Anemia Associated with Cancer Therapy: A Systematic Review and Meta-analysis of Controlled Clinical Trials," *Journal of National Cancer Institute*, 93(16):1204-1214.

Senter et al., (1988), "Anti-tumor Effects of Antibody-alkaline Phosphatase Conjugates in Combination with Etoposide Phosphate," *Proc. Natl. Acad. Sci. USA*, 85(13):4842-4846.

Shanafelt et al., (2000), "A T-cell-Selective Interleukin 2 Mutein Exhibits Potent Antitumor Activity and is Well Tolerated *In Vivo*," *Nature Biotechnology*, 18:1197-1202.

Sharma et al., (1999), "T cell-derived IL-10 Promotes Lung Cancer Growth by Suppressing Both T cell and APC Function," *Journal of Immunology*, 163:5020-5028.

Shen et al., (1986), "Heteroantibody-Mediated Cytotoxicity: Antibody to the High Affinity Fc Receptor for IgG Mediates Cytotoxicity by Human Monocytes That is Enhanced by Interferon-γ and is Not Blocked by Human IgG," *J. Immunology*, 137(11):3378-3382.

Shiff et al., (1995), "Sulindac Sulfide, an Asprin-like Compound, Inhibits Proliferation, Causes Cell Cycle Quiescence, and Induces Apoptosis in HT-29 Colon Adenocarcinoma Cells," *Journal of Clinical Investigation*, 96:491-503.

Shin et al., (1990), "Expression and Characterization of an Antibody Binding Specificity Joined to Insulin-like Growth Factor I: Potential Applications for Cellular Targeting," *Proc. Natl. Acad. Sci. USA*, 87:5322-5326.

Shinkawa et al., (2003), "The Absence of Fucose But Not the Presence of Galactose or Bisecting N-Acetylglucosamine of Human IgG1 Complex-type Oligosaccharides Shows the Critical Role of Enhancing Antibody-dependent Cellular Cytotoxicity," *J. Biol. Chem.*, 278:3466-3473.

Sim et al., (1997), "A Recombinant Human Angiostatin Protein Inhibits Experimental Primary and Metastatic Cancer," *Cancer Research*, 57:1329-1334.

Spiekermann et al., (2002), "Receptor-mediated Immunoglobulin G Transport Across Mucosal Barriers in Adult Life: Functional Expression of FcRn in the Mammalian Lung," *J. Exp. Med.*, 196:303-310.

Strom et al., (1996), "Therapeutic Approach to Organ Transplantation," Chapter 36, pp. 451-456, in *Therapeutic Immunology*, Austen et al., (eds.), Blackwell Science.

Sulitzeanu, (1993), "Immunosuppressive Factors in Human Cancer," pp. 247-266 in *Advances in Cancer Research*, vol. 60, Vande Woude et al. (eds.), Academic Press, Inc.

Syed et al., (1998), "Efficiency of Signaling Through Cytokine Receptors Depends Critically on Receptor Orientation," *Nature*, 395:511-516.

Taniguchi et al., (1983), "Structure and Expression of a Cloned cDNA for Human Interleukin-2," *Nature*, 302:305-309.

Tao et al., (1989), "Studies of Aglycosylated Chimeric Mouse IgG: Role of Carbohydrate in the Structure and Effector Functions Mediated by the Human IgG Constant Region," *J. Immunology*, 143(8):2595-2601.

Tao et al., (1993), "Structural Features of Human Immunoglobulin G that Determine Isotype-Differences in Complement Activation," *J. Exp. Med.*, 178(2):661-667.

Teicher et al., (1994), "Potentiation of Cytotoxic Cancer Therapies by TNP-470 Alone and With Other Anti-Angiogenic Agents," *Int. J. Cancer*, 57:920-925.

*The Merck Manual of Diagnosis and Therapy*, 17th Ed., (1999) pp. 990-993 and 1278-1283.

Thommesen et al., (2000), "Lysine 322 in the Human IgG3 CH2 Domain is Crucial for Antibody Dependent Complement Activation," *Mol. Immunol.*, 37(16):995-1004.

Till et al., (1988), "An Assay that Predicts the Ability of Monoclonal Antibodies to Form Potent Ricin A Chain-containing Immunotoxins," *Cancer Research*, 48(5):1119-1123.

Till et al., (1988), "HIV-Infected Cells are Killed by rCD4-Ricin A Chain," *Science*, 242:1166-1168.

Trinchieri, (1994), "Interleukin-12: A Cytokine Produced by Antigen-Presenting Cells With Immunoregulatory Functions in the Generation of T-Helper Cells Type 1 and Cytotoxic Lymphocytes," *Blood*, 84:4008-4027.

Vagliani et al., (1996), "Interleukin 12 Potentiates the Curative Effect of a Vaccine Based on Interleukin 2-transduced Tumor Cells," *Cancer Research*, 56:467-470.

Varki et al., (1984), "Antigens Associated with a Human Lung Adenocarcinoma Defined by Monoclonal Antibodies," *Cancer Research*, 44:681-687.

Verhoeyen et al., (1988), "Reshaping Human Antibodies: Grafting an Antilysozyme Activity," *Science*, 239:1534-1536.

Villunger et al., (1997), "Constitutive Expression of Fas (Apo-1/CD95) Ligand on Multiple Myeloma Cells: A Potential Mechanism of Tumor-induced Suppression of Immune Surveillance," *Blood*, 90(1):12-20.

Watanabe et al., (1997), "Long-term Depletion of Naive T cells in Patients Treated for Hodgkin's Disease," *Blood*, 90(9):3662-3672.

Wells, (1990), "Additivity of Mutational Effect in Proteins," *Biochemistry*, 29(37):8509-8517.

Wen et al., (1993), "Erythropoietin Structure-Function Relationships: High Degree of Sequence Homology Among Mammals," *Blood*, 82(5):1507-1516.

Williams et al., (1986), "Production of Antibody-tagged Enzymes by Myeloma Cells: Application to DNA Polymerase I Klenow Fragment," *Gene*, 43:319-324.

Williams et al., (1987), "Diphtheria Toxin Receptor Binding Domain Substitution with Interleukin-2: Genetic Construction and Properties of a Diphtheria Toxin-related Interleukin-2 Fusion Protein," *Protein Engineering*, 1(6):493-498.

Wooley et al., (1993), "Influence of a Recombinant Human Soluble Tumor Necrosis Factor Receptor Fc Fusion Protein on Type II Collagen-Induced Arthritis in Mice," *J. Immunology*, 151:6602-6607.

Wu et al., (1997), "Suppression of Tumor Growth with Recombinant Murine Angiostatin," *Biochemical and Biophysical Research Communications*, 236:651-654.

Xiang et al., (1997), "Elimination of Established Murine Colon Carcinoma Metastases by Antibody-Interleukin 2 Fusion Protein Therapy," *Cancer Research*, 57:4948-4955.

Xiang et al., (1998), "Induction of Persistent Tumor-protective Immunity in Mice Cured of Established Colon Carcinoma Metastases," *Cancer Research*, 58(17):3918-3925.

Xiang et al., (1999) "T Cell Memory against Colon Carcinoma is Long-lived in the Absence of Antigen," *J. Immunology*, 163(7):3676-83.

Xiang et al., (2001), "A Dual Function DNA Vaccine Encoding Carcinoembryonic Antigen and CD40 Ligand Trimer Induces T Cell-mediated Protective Immunity Against Colon Cancer in Carcinoebryonic Antigen-Transgenic Mice," *J. Immunology*, 167(8):4560-5.

Xiang et al., (2001), "Protective Immunity Against Human Carcinoembryonic Antigen (CEA) Induced by an Oral DNA Vaccine in CEA-transgenic Mice," *Clinical Cancer Research*, 7(3 Supp):S856-S864.

Xu et al., (1994), "Residue at Position 331 in the IgG1 and IgG4 CH2 Domains Contributes to Their Differential Ability to Bind and Activate Complement," *J. Biol. Chem.*, 269(5):3469-3474.

Yu et al., (1998), "Phase I Trial of a Human-Mouse Chimeric Anti-Disaloganglioside Monoclonal Antibody ch14.18 in Patients with Refractory Neuroblastoma and Osteosarcoma," *J. Clinical Oncology*, 16(6):2169-80.

Zagozdzon et al., (1999), "Potentiation of Antitumor Effects of IL-12 in Combination with Paclitaxel in Murine Melanoma Model In Vivo," *International Journal of Molecular Medicine*, 4:645-648.

Zheng et al., (1995), "Administration of Noncytolytic IL-10/Fc in Murine Models of Lipopolysaccharide-induced Septic Shock and Allogenic Islet Transplantation," *J. Immunology*, 154:5590-5600.

Baici et al., (1980), "Kinetics of the Different Susceptibilities of the Four Human Immunoglobulin G Subclasses to Proteolysis by Human Lysosomal Elastase," *Scand. J. Immunol.* 12(1):41-50.

Boshart et al., (1985), "A Very Strong Enhancer is Located Upstream of an Immediate Early Gene of Human Cytomegalovirus," *Cell*, 41:521-530.

Brekke et al., (1994), "Human IgG Isotype-Specific Amino Acid Residues Affecting Complement-Mediated Cell Lysis and Phagocytosis," *Eur. J. Immunol.*, 24:2542-2547.

Bubenik et al., (1995), "Interleukin-2 Gene Therapy of Residual EL-4 Leukaemia Potentiates the Effect of Cyclophosphamide Pretreatment," *J. Cancer Res. Clin. Oncol.*, 121:39-43.

Carnemolla et al., (1989), "A Tumor-Associated Fibronectin Isoform Generated by Alternative Splicing of Messenger RNA Precursors," *J. Cell Biol.*, 108:1139-1148.

Carnemolla et al., (1992), "The Inclusion of the Type III Repeat ED-B in the Fibronectin Molecule Generates Conformational Modifications That Unmask a Cryptic Sequence," *J. Biol. Chem.*, 267(34):24689-24692.

Chappel et al., (1991), "Identification of the Fcγ Receptor Class I Binding Site In Human IgG Through Use of Recombinant IgG1/IgG2 Hybrid and Point-Mutated Antibodies," *Proc. Natl. Acad. Sci. USA*, 88(20):9036-40.

Connor et al., (2004), "Ex vivo Evaluation of Anti-EpCAM Immunocytokine huKS-IL2 in Ovarian Cancer," *J. Immunotherapy*, 27:211-219.

Daugherty et al., (1991), "Polymerase Chain Reaction Facilitates the Cloning, CDR-grafting, and Rapid Expression of a Murine Monoclonal Antibody Directed Against the CD18 Componet of Leukocyte Integrins," *Nucleic Acid Res.*, 19:2471-2476.

de la Salle et al., (1996), "Fcγon Human Dendritic Cells," in *Human IgG Receptors*, pp. 39-55, van de Winkel et al. (eds.), R.G. Landes Co.

Dorai et al., (1991), "Aglycosylated Chimeric Mouse/Human IgG1 Antibody Retains Some Effector Function," *Hybridoma*, 10(2):211-217.

Dorai et al., (1992), "Role of Inter-Heavy and Light Chain Disulfide Bonds in the Effector Functions of Human IgG1," *Molecular Immunology*, 29(12):1487-1491.

Elliott et al., (1996), "Fine-Structure Epitope Mapping of Antierythropoietin Monoclonal Antibodies Reveals a Model of Recombinant Human Erythropoietin Structure," *Blood*, 87:2702-2713.

Gainsford et al., (1996), "Leptin Can Induce Proliferation, Differentiation, and Functional Activation of Hemopoietic Cells," *Proc. Natl. Acad. Sci. USA*, 93:14564-14568.

Gillies et al., (1991), "Targeting Human Cytotoxic T Lymphocytes to Kill Heterologous Epidermal Growth Factor Receptor-Bearing Tumor Cells: Tumor-Infiltrating Lymphocyte/Hormone Receptor/Recombinant Antibody," *J. Immunology*, 146(3):1067-1071.

Gurewich et al., (1998), "Characterization of the Intrinsic Fibrinolytic Properties of Pro-Urokinase Through a Study of Plasmin-Resistant Mutant Forms Produced by Site-Specific Mutagenesis of Lysine," *J. Clin. Invest.*, 82:1956-1962.

Halin et al., (2002), "Enhancement of the Antitumor Activity of Interleukin-12 by Targeted Delivery to Neovasculature," *Nature Biotechnology*, 20:264-269.

Handgretinger et al., (1995), "A Phase I Study of Human/Mouse Chimeric Anti-ganglioside GD2 Antibody ch14.18 in Patients with Neuroblastoma," *European J. Cancer*, 31 A(2):261-267.

Henikoff et al., (1992), "Amino Acid Substitution Matrices from Protein Blocks," *Proc. Natl. Acad. Sci. USA* ,89:10915-10919.

Hulett et al., (1994), "Molecular Basis of Fc Receptor Function," *Adv. Immunol.*, 57:1-127.

Hurn et al., (1980), "Production of Reagent Antibodies," *Methods in Enzymology*, 70: 104-142.

Isenman et al., (1975), "The Structure and Function of Immunoglobulin Domains: II. The Importance of Interchain Disulfide Bonds and the Possible Role of Molecular Flexibility in the Interaction between Immunoglobulin G and Complement," *J. Immunology*, 114(6):1726-1729.

Jefferis et al., (1990), "Molecular Definition of Interaction Sites on Human IgG for Fc Receptors (huFcγR)," *Mol. Immunol.*, 27(12):1237-1240.

Karpusas et al., (1997), "The Crystal Structure of Human Interferon β at 2.2-Å Resolution," *Proc. Natl. Acad. Sci. USA*, 94:11813-11818.

Ko et al., (2004), "Safety, Pharmacokinetics, and Biological Pharmacodynamics of the Immunocytokine EMD 273066 (huKS-IL2)," *J. Immunotherapy*, 27:232-239.

Lo et al., (1992), "Expression and Secretion of an Assembled Tetrameric CH2-deleted Antibody in *E. coli.*," *Hum. Antibod. Hybridomas*, 3:123-128.

MacLean et al., (1996), "Enhancing the Effect of Theratope STn-KLH Cancer Vaccine in Patients with Metastatic Breast Cancer by Pretreatment with Low-Dose Intravenous Cyclophosphamide," *J. Immunother.*, 19(4):309-316.

Maecker et al., (1997), "DNA Vaccination with Cytokine Fusion Constructs Biases the Immune Response to Ovalbumin," *Vaccine*, 15(15):1687-1696.

Martin et al., (2001), "Crystal Structure at 2.8 Å of an FcRn/Heterodimeric Fc Complex: Mechanism of pH-Dependent Binding," *Mol. Cell.*, 7(4):867-77.

Miyake et al., (1988), "Synthesis of Recombinant Human Single-Chain Urokinase-Type Plasminogen Activator Variants Resistant to Plasmin and Thrombin," *J. Biochem.*, 104:643-647.

Mueller et al., (1990), "Enhancement of Antibody-Dependent Cytotoxicity With a Chimeric Anti-GD2 Antibody," *J. Immunology*, 144(4):1382-1386.

Mueller et al., (1990), "Serum Half-Life and Tumor Localization of a Chimeric Antibody Deleted of the CH2 Domain and Directed Against the Disialoganglioside GD2," *Proc. Natl. Acad. Sci. USA.*, 87:5702-5705.

Mullins et al., (1997), "Taxol-mediated Changes in Fibrosarcoma-Induced Immune Cell Function: Modulation of Antitumor Activities," *Cancer Immunol. Immunother*, 45:20-28.

Naramura et al., (1993), "Therapeutic Potential of Chimeric and Murine Anti-(Epidermal Growth Factor Receptor) Antibodies in a Metastasis Model for Human Melanoma," *Cancer Immuno. Immunother.*, 37:343-349.

Neal et al., (2004), "Enhanced Activity of Hu14.18-IL2 Immunocytokine against Murine NXS2 Neuroblastoma when Combined with Interleukin Therapy," *Clin. Cancer. Res.*, 10:4839-4847.

Nelles et al., (1987), "Characterization of Recombinant Human Single Chain Urokinase-type Plaminogen Activtor Mutants Produced by Site-Specific Mutagenesis of Lysine 158," *J. Biol. Chem.*, 262(12):5682-5689.

Poon et al., (1995), "Structure and Function of Several Anti-Dansyl Chimeric Antibodies Formed by Domain Interchanges Between Human IgM and Mouse IgG2b," *J. Biol. Chem.*, 270:8571-7.

Reisfeld et al., (1994), "Potential of Genetically Engineered Anti-Ganglioside GD2 Antibodies for Cancer Immunotherapy," *Prog. Brain Res.*, 101:201-212.

Runkel et al., (1998), "Structural and Functional Differences Between Glycosylated and Non-glycosylated Forms of Huamn Interferon-β (IFN-β)," *Pharmaceutical Res.*, 15:641-649.

Sakano et al., (1980), "Two Types of Somatic Recombination are Necessary for the Generation of Complete Immunoglobulin Heavy-Chain Genes," *Nature*, 286:676-683.

Saleh et al., (1992), "Phase I Trial of the Chimeric Anti-GD2 Monoclonal Antibody ch14.18 in Patients With Malignant Melanoma," *Hum. Antiob. Hybridomas*, 3:19-24.

Sallusto et al., (1994), "Efficient Presentation of Soluble Antigen by Cultured Human Dendritic Cells Is Maintained by Granulocyte/Macrophage Colony-stimulating Factor Plus Interleukin 4 and Downregulated by Tumor Necrosis Factor α," *J. Exp. Med.*, 179:1109-1118.

Schlom (1991), "Monoclonal Anitbodies: They're More and Less Than You Think," in *Molecular Foundations of Oncology*, pp. 95-134.

Senior et al., (2000), "Cleavage of a Recombinant Human Immunoglobulin A2 (IgA2)-IgA1 Hybrid Antibody by Certain Bacterial IgA1 Proteases," *Infect. Immun.*, 68(2):463-469.

Simonsen et al., (1983), "Isolation and Expression of an Altered Mouse Dihydrofolate Reductase cDNA," *Proc. Natl. Acad. Sci. USA*, 80:2495-2499.

Smith et al., (1981), "Identification of Common Molecular Subsequences," *J. Mol. Biol.*, 147:195-197.

Taniguchi et al., (1980), "Expression of the Human Fibroblast Interferon Gene in *Escherichia Coli*," *Proc. Natl. Acad. Sci. USA*, 77:5230-5233.

Von Heijne et al., (1986), "A New Method for Predicting Signal Sequence Cleavage Sites," *Nucleic Acid Res.*, 14:4683-4690.

Ward et al., (1995), "The Effector Functions of Immunoglobulins: Implications for Therapy," *Therapeutic. Immunology*, 2:77-94.

Watson et al., (1984), "Compilation of Published Signal Sequences," *Nucleic Acid Res.*, 12:145-5164.

Weber et al., (2001), "Phase I Trial of huKS-IL2 Immunocytokine in Patients with Prostate Carcinoma: Clinical, PK, and Biological PD Results (Abstract)," *American Society of Clinical Oncology Program/Proceedings*, 20(Part 1):259a.

Wen et al., (1994), "Erythropoietin Structure-Function Relationships: Identification of Functionally Important Domains," *J. Biological Chemistry*, 269(36):22839-22846.

Zuckier et al., (1998), "Chimeric Human-Mouse IgG Antibodies with Shuffled Constant Region Exons Demonstrate That Multiple Domains Contribute to In Vivo Half-Life," *Cancer Res.*, 58(17):3905-8.

Written Opinion for International Application No. PCT/US02/07011 mailed Mar. 10, 2003. (4 pages).

International Preliminary Examination Report for International Application No. PCT/US02/07011 mailed Dec. 9, 2003. (4 pages).

Chapman et al., (1994), "Mapping Effector Functions of a Monoclonal Antibody to GD3 by Characterization of a Mouse-Human Chimeric Antibody," *Cancer Immuno. Immunother.*, 39:198-204.

Tao et al., "The Differential Ability of Human IgG1 and IgG4 to Activate Complement Is Determined by the COOH-terminal Sequence of the $C_H2$ Domain," *J. Exp. Med.*, Apr. 1991, vol. 173, pp. 1025-1028.

Aichele et al., (1994), "Peptide-Induced T-Cell Tolerance to Prevent Autoimmune Diabetes in a Transgenic Mouse Model," *Proc. Natl. Acad. Sci. USA*, 91:444-448.

Altschul et al., (1990), "Basic Local Alignment Search Tool," *J. Mol. Biol.*, 215:403-10.

Altschul et al., (1997), "Gapped BLAST and PSI-BLAST: A New Generation of Protein Database Search Programs," *Nucleic Acids Res.*, 25(17):3389-402.

Anderson et al., (1980), "Characterization of the Fc Receptor for IgG on a Human Macrophage Cell Line U937," *J. Immunol.*, 125:2735-41.

Anderson et al., (1994), "Effects of Route and Formulation on Clinical Pharmacokinetics of Interleukin-2," *Clin. Pharmacokinet.*, 27(1):19-31.

Barbulescu et al., (1998), "IL-12 and IL-18 Differentially Regulate the Transcriptional Activity of the Human IFN-γ Promoter in Primary CD4+ T Lymphocytes," *J. Immunol.*, 160:3642-7.

Bednarek et al., (1991), "Soluble HLA-A2.1 Restricted Peptides that are Recognized by Influenza Virus Specific Cytotoxic T Lymphocytes," *J. Immunol. Methods*, 139:41-47.

Benacerraf et al., (1959), "The Clearance of Antigen Antibody Complexes from the Blood by the Reticuloendothelial System," *J. Immunol.*, 82:131-7.

Böhm, (1994), "On the Use of LUDI to Search the Fine Chemicals Directory for Ligands of Proteins of Known Three-Dimensional Structure," *J. Comput. Aided Mol. Des.*, 8:623-32.

Böhm, (1994), "The Development of a Simple Empirical Scoring Function to Estimate the Binding Constant for a Protein-Ligand Complex of Known Three-Dimensional Structure," *J. Comput. Aided Mol. Des.*, 8:243-56.

Böhm, (1998), "Prediction of Binding Constants of Protein Ligands: A Fast Method for the Prioritization of Hits Obtained from De Novo Design or 3D Database Search Programs," *J. Comput. Aided Mol. Des.*, 12(4):309-23.

Boulianne et al., (1984), "Production of Functional Chimaeric Mouse/Human Antibody," *Nature*, 312:643-6.

Bourgois et al., (1974), "Determination of the Primary Structure of a Mouse IgG2a Immunoglobulin Amino Acid Sequence of the Fc Fragment: Implications for the Evolution of Immunoglobulin Structure and Function," *Eur. J. Biochem.*, 43:423-35.

Brambell et al., (1964), "A Theoretical Model of Gamma-Globulin Catabolism," *Nature*, 203:1352-54.

Brazolot Millan et al., (1998), "Cpg DNA Can Induce Strong TH1 Humoral and Cell-Mediated Immune Responses against Hepatitis B Surface Antigen in Young Mice," *Proc. Natl. Acad. Sci. USA*, 95:15553-8.

Brem et al., (1993), "The Combination of Antiangiogenic Agents to Inhibit Primary Tumor Growth and Metastasis," *J. Pediatr. Surg.*, 28:1253-7.

Brocklebank et al., (2001), "Enumeration of CD34+ Cells in Cord Blood: A Variation on a Single-Platform Flow Cytometric Method Based on the ISHAGE Gating Strategy," *Cytometry*, 46(4):254-61.

Brooks et al., (1983), "CHARMM: A Program for Macromolecular Energy Minimization and Dynamics Calculations," *J. Comput. Chemistry*, 4:187-217.

Broudy et al., (1988), "Recombinant Human Erythropoietin: Purification and Analysis of Carbohydrate Linkage," *Arch. Biochem. Biophys.*, 265:329-36.

Bumol et al., (1982), "Unique Glycoprotein-Proteoglycan Complex Defined by Monoclonal Antibody on Human Melanoma Cells," *Proc. Natl. Acad. Sci. USA*, 79:1245-9.

Casadevall et al., (2002), "Pure Red-Cell Aplasia and Antierythropoietin Antibodies in Patients Treated with Recombinant Erythropoietin," *N. Engl. J. Med.*, 346(7):469-75.

Cazzola et al., (1998), "Red Blood Cell Precursor Mass as an Independent Determinant of Serum Erythropoietin Level," *Blood*, 91:2139-45.

Chan et al., (1992), "Mechanisms of IFN-Gamma Induction by Natural Killer Cell Stimulatory Factor (NKSF/IL-12). Role of Transcription and mRNA Stability in the Synergistic Interaction Between NKSF and IL-2," *J. Immunol.*, 148:92-98.

Cheetham, (1998), "NMR Structure of Human Erythropoietin and a Comparison with its Receptor Bound Conformation," *Natl. Struct. Biol.*, 5:861-6.

Ciardiello et al., (1996), "Antitumor Activity of Combined Blockade of Epidermal Growth Factor Receptor and Protein Kinase A," *J. Natl. Cancer Inst.*, 88:1770-6.

Cirulli et al., (1998), "KSA Antigen Ep-CAM Mediates Cell-Cell Adhesion of Pancreatic Epithelial Cells: Morphoregulatory Roles in Pancreatic Islet Development," *J. Cell Biol.*, 140:1519-34.

Cohen et al., (1998), "An Artificial Cell-Cycle Inhibitor Isolated from a Combinatorial Library," *Proc. Natl. Acad. Sci. USA*, 95:14272-7.

Congote et al., (1984), Abstract 364 in "Proceedings 7th Intl. Congress of Endocrinology," Quebec City, Quebec.

Congote, (1983), "Isolation of Two Biologically Active Peptides, Erythrotropin I and Erythrotropin II from Fetal Calf Intestine," *Biochem. Biophys. Res. Commun.*, 115(2):477-83.

Congote, (1984), "Extraction form Fetal Bovine Serum of Erythrotropin, and Erythroid Cell-Stimulating Factor," *Anal. Biochem.*, 140:428-33.

Cosenza et al., (1997), "Disulfide Bond Assignment in Human Interleukin-7 by Matrix-Assisted Laser Desorption/Ionization Mass Spectroscopy and Site-Directed Cysteine to Serine Mutational Analysis," *J. Biol. Chem.*, 272:32995-3000.

Cunningham et al., (1989), "High-Resolution Epitope Mapping of Hgh-Receptor Interactions by Alanine-Scanning Mutagenesis," *Science*, 244:1081-85.

Curiel et al., (1991), "Adenovirus Enhancement of Transferrin-Polylysine-Mediated Gene Delivery," *Proc. Natl. Acad. Sci. USA*, 88:8850-4.

Dauber-Osguthorpe et al., (1988), "Structure and Energetics of Ligand Binding to Proteins: *Escherichia coli* Dihydrofolate Reductase-Trimethoprim, A Drug-Receptor System," *Proteins*, 4(1):31-47.

De Bruijn et al., (1995), "Phagocyte-Induced Antigen-Specific Activation of Unprimed CD8+ T Cells in Vitro," *Eur. J. Immunol.*, 25:1274-85.

Delorme et al., (1992), "Role of Glycosylation on the Secretion and Biological Activity of Erythropoietin," *Biochemistry*, 31:9871-6.

Desai et al., (1992), "IL-12 Receptor. II. Distribution and Regulation of Receptor Expression," *J. Immunol.*, 148:3125-32.

Donnelly et al., (1993), "Targeted Delivery of Peptide Epitopes to Class 1 Major Histocompatibility Molecules by a Modified Pseudomonas Exotoxin," *Proc. Natl. Acad. Sci. USA*, 90:3530-4.

Donnelly et al., (1997), "DNA Vaccines," *Annu. Rev. Immunol.*, 15:617-48.

Dube et al., (1988), "Glycosylation at Specific Sites of Erythropoietin is Essential for Biosynthesis, Secretion, and Biological Function," *J. Biol. Chem.*, 263:17516-21.

Ellison et al., (1982), "The Nucleotide Sequence of a Human Immunoglobulin C Gammal Gene," *Nucleic Acids Res.*, 10:4071-9.

Faas et al., (1993), "Phenotypically Diverse Mouse Thymic Stromal Cell Lines which Induce Proliferation and Differentiation Of Hematopoietic Cells," *Eur. J. Immunol.*, 23:1201-14.

Farner et al., (1995), "Distinction Between Gamma C Detection and Function in YT Lymphoid Cells and in the Granulocyte-Macrophage Colony-Stimulating Factor-Responsive Human Myeloid Cell Line, Tf-I," *Blood*, 86:4568-78.

Fawell et al., (1994), "Tat-Mediated Delivery of Heterologous Proteins into Cells," *Proc. Natl. Acad. Sci. USA*, 91:664-8.

Fu et al., (1993), "The Sheep Erythropoietin Gene: Molecular Cloning and Effect of Hemorrhage on Plasma Erythropoietin and Renal/Liver Messenger RNA in Adult Sheep," *Mol. Cell. Endocrinol.*, 93:107-16.

Gammon et al., (1992), "Endogenous Loading of HLA-A2 Molecules with an Analog of the Influenza Virus Matrix Protein-Derived Peptide and Its Inhibition By An Exogenous Peptide Antagonist," *J. Immunol.*, 148:7-12.

Ghetie et al., (1990), "Disseminated or Localized Growth of a Human B-Cell Tumor (Daudi) in SCID Mice," *Intl. J. Cancer*, 45:481.

Ghetie et al., (1997), "FcRn: The MHC Class I-Related Receptor that is More Than an IgG Transporter," *Immunology Today*, 18(12):592-598.

Goldwasser et al., (1971), "Purification of Erythropoietin," *Proc. Natl. Acad. Sci. USA*, 68:697-8.

Goldwasser et al., (1975), "Erythropoietin: Assay and Study of its Mode of Action," *Methods Enzymol.*, 37(Ptb):109-21.

Handgretinger et al., (2001), "Immunological Aspects of Haploidentical Stem Cell Transplantation in Children," *Ann. NY Acad. Sci.*, 938:340-57.

Hashimoto et al., (1999), "Differential Antitumor Effects of Administration of Recombinant IL-18 or Recombinant IL-12 are Mediated Primarily by Fas-Fas Ligand- and Perforin-Induced Tumor Apoptosis, Respectively," *J. Immunol.*, 163:583-9.

Hilgers et al., (1999), "Sulfolipo-Cyclodextrin in Squalane-In-Water as a Novel and Safe Vaccine Adjuvant," *Vaccine*, 17:219-28.

Hori et al., (1987), "Establishment of an Interleukin 2-Dependent Human T Cell Line from a Patient with T Cell Chronic Lymphocytic Leukemia Who is Not Infected with Human T Cell Leukemia/Lymphoma Virus," *Blood*, 70:1069-72.

Huston et al., (1988), "Protein Engineering of Antibody Binding Sites: Recovery of Specific Activity in an Anti-Digoxin Single-Chain Fv Analogue Produced In *Escherichia coli*," *Proc. Natl. Acad. Sci. USA*, 85:5879.

Isaacs et al., (1998), "Therapy with Monoclonal Antibodies. II. The Contribution of Fcγ Receptor Binding and the Influence of CH1 and CH3 Domains on In Vivo Effector Funcion," *J. Immunol.*, 161:3862-3869.

Jacobs et al., (1985), "Isolation and Characterization of Genomic And CDNA Clones of Human Erythropoietin," *Nature*, 313:806-10.

Karlin et al., (1990), "Methods for Assessing the Statistical Significance of Molecular Sequence Features by Using General Scoring Schemes," *Proc. Natl. Acad. Sci. USA*, 87:2264-8.

Kelner et al., (1994), "Lymphotactin: a Cytokine that Represents a New Class of Chemokine," *Science*, 266:1395-9.

Kirkman et al., (1989), "Prolongation of Cardiac Allograft Survival in Murine Recipients Treated with a Diphtheria Toxin-Related Interleukin-2 Fusion Protein," *Transplantation*, 47(2):327-330.

Klinman et al., (1997), "Contribution of CPG Motifs to the Immunogenicity of DNA Vaccines," *J. Immunol.*, 158:3635-9.

Kuntz et al., (1982), "A Geometric Approach to Macromolecule-Ligand Interactions," *J. Mol. Biol.*, 161:269-88.

Kurtz et al., (1982), "A New Candidate for the Regulation of Erythropoiesis. Insulin-Like Growth Factor 1," *FEBS Lett.*, 149(1):105-8.

Lai et al., (1986), "Structural Characterization of Human Erythropoietin," *J. Biol. Chem.*, 261:3116-21.

Lai et al., (1998), "DNA Vaccines," *Crit. Rev. Immunol.*, 18:449-84.

Lanza et al., (1993), "Active Immunity against the CD4 Receptor by Using an Antibody Antigenized with Residues 41-55 of the First Extracellular Domain," *Proc. Natl. Acad. Sci. USA*, 90:11683-7.

Lawn et al., (1981), "DNA Sequence of a Major Human Leukocyte Interferon Gene," *Proc. Natl. Acad. Sci. USA*, 78:5435-9.

Lin et al., (1985), "Cloning and Expression of the Human Erythropoietin Gene," *Proc. Natl. Acad. Sci. USA*, 82:7580-4.

Lin et al., (1986), "Monkey Erythropoietin Gene: Cloning, Expression and Comparison with the Human Erythropoietin Gene," *Gene*, 44:201-9.

Lode et al., (1998), "Gene Therapy with a Single Chain Interleukin 12 Fusion Protein Induces T Cell-Dependent Protective Immunity in a Syngeneic Model of Murine Neuroblastoma," *Proc. Natl. Acad. Sci. USA*, 95:2475-80.

Lorenz et al., (1999), "Induction of Anti-Tumor Immunity Elicited by Tumor Cells Expressing a Murine LFA-3 Analog Via a Recombinant Vaccinia Virus," *Hum. Gene Ther.*, 10:623-31.

Lotze et al., (1996), "Cytokine Gene Therapy of Cancer Using Interleukin-12: Murine and Clinical Trials," *Ann. NY Acad. Sci.*, 795:440-54.

Macdougall et al., (1999), "Pharmacokinetics of Novel Erythropoiesis Stimulating Protein Compared with Epoetin Alga in Dialysis Patients," *J. Am. Soc. Nephrol.*, 10:2392-5.

Maghazachi et al., (1997), "Interferon-Inducible Protein-10 and Lymphotactin Induce the Chemotaxis and Mobilization fo Intracellular Calcium in Natural Killer Cells through Pertussis Toxin-Sensitive and—Insensitive Heterotrimeric G-Proteins," *FASEB J.*, 11:765-74.

Maloy et al., "Regulatory T Cells in the Control of Immune Pathology," *Nature Immunol.*, 2:816-22.

Mariani et al., (1997), "Tumor Targeting Potential of the Monoclonal Antibody BC-1 against Oncofetal Fibronectin in Nude Mice Bearing Human Tumor Implants," *Cancer*, 80:2378-84.

Marshall et al., (1995), "Prediction of Peptide Affinity to HLA-DR Molecules," *Biomed. Pept. Proteins Nucleic Acids*, 1(3):157-62.

Marshall, K.W., (1994), "Role of the Polymorphic Residues in HLA-DR Molecules in Allele-Specific Binding of Peptide Ligands," *J. Immunol.*, 152:4946-57.

McDonald, (1986), "Cloning, Sequencing, and Evolutionary Analysis of the Mouse Erythropoietin Gene," *Mol. Cell. Biol.*, 6:842-8.

McGonigle et al., (1984), "Erythropoietin Deficiency and Inhibition of Erythropoiesis in Renal Insufficiency," *Kidney Int.*, 25(2):437-44.

McMahan et al., (1991), "A Novel IL-I Receptor, Cloned From B-Cells by Mammalian Expression is Expressed in Many Cell Types," *EMBO J.*, 10:2821-32.

McMahon et al., (1990), "Pharmacokinetics and Effects of Recombinant Human Erythropoietin after Intravenous and Subcutaneous Injections in Healthy Volunteers," *Blood*, 76:1718-22.

Mehrotra et al., (1993), "Effects of IL-12 on the Generation of Cytotoxic Activity in Human CD8+ T Lymphocytes," *J. Immunol.*, 151:2444-52.

Menard et al., (1983), "Generation of Monoclonal Antibodies Reacting with Normal and Cancer Cells of Human Breast," *Cancer Res.*, 43:1295-300.

Miyake et al., (1997), "Purification of Human Erythropoietin," *J. Biol. Chem.*, 252:5558-64.

Morrison et al., (1984), "Chimeric Human Antibody Molecules: Mouse Antigen-Binding Domains with Human Constant Region Domains," *Proc. Natl. Acad. Sci. USA*, 81:6851-5.

Nagao et al., (1992), "Nucleotide Sequence of Rat Erythropoietin," *Biochim. Biophys. Acta*, 1171(1):99-102.

Nastala et al., (1994), "Recombinant IL-12 Administration Induces Tumor Regression in Association with IFN-Gamma Production," *J. Immunol.*, 153:1697-706.

Naughton et al., (1983), "Evidence for an Erythropoietin-Stimulating Factor in Patients with Renal and Hepatic Disease," *Acta. Haematol.*, 69:171-9.

Noguchi et al., (1994), "A Mouse Mutant P53 Product Recognized by CD4+ and CD8+ T Cells," *Proc. Natl. Acad. Sci. USA*, 91:3171-5.

Orlandi et al., (1989), "Cloning Immunoglobulin Variable Domains for Expression by the Polymerase Chain Reaction," *Proc. Natl. Acad. Sci. USA*, 86:3833-7.

Palmer et al., (2001), "Phase I Study of the BLP 25 (MUCI Peptide) Liposomal Vaccine for Active Specific Immunotherapy in Stage IIIB/IV Non-Small-Cell Lung Cancer," *Clinical Lung Cancer*, 3(1):49-57.

Palucka et al., (1998), "Dendritic Cells as the Terminal Stage of Monocyte Differentiation," *J. Immunol.*, 160:4587-95.

Panina-Bordignon et al., (1989), "Universally Immunogenic T Cell Epitopes: Promiscuous Binding to Human MHC Class II and Promiscuous *Recognition* by T Cells," *Eur. J. Immunol.*, 19:2237-42.

Pavlovic-Kentera et al., (1980), "Effects of Prostaglandin Synthetase Inhibitors, Salt Overload and Renomedullary Dissection on the Hypoxia Stimulated Erythropoietin Production in Rats," *Expt. Hematol.*, 8(Supp. 8):283-92.

Pedley et al., (1999), "Enhancement of Antibody-Directed Enzyme Prodrug Therapy in Colorectal Xenografts by an Antivascular Agent," *Cancer Res.*, 59:3998-4003.

Perussia et al., (1992), "Natural Killer (NK) Cell Stimulatory Factor or IL-12 Has Differential Effects on the Proliferation of TCR-Alpha Beta+, TCR-Gamma Delta+ T Lymphocytes, and NK Cells," *J. Immunol.*, 149:3495-502.

Pluschke et al., (1996), "Molecular Cloning of a Human Melanoma-Associated Chondroitin Sulfate Proteoglycan," *Proc. Natl. Acad. Sci. USA*, 93:9710-5.

Queen et al., (1989), "A Humanized Antibody that Binds to the Interleukin 2 Receptor," *Proc. Natl. Acad. Sci. USA*, 86:10029-33.

Radhakrishnan et al., (1996), "Zinc Mediated Dimer of Human Interferon-Alpha 2b Revealed by X-Ray Crystallography," *Structure* 4:1453-63.

Ramachandran et al., (1968)"Confirmation of Polypeptides and Proteins," *Adv. Prot. Chem.*, 23:283-438 (At pp. 285-294).

Rarey et al., (1995), "Time-Efficient Docking of Flexible Ligands into Active Sites Of Proteins," *Proc. Int. Conf. Intell. Syst. Mol. Biol.* 3:300-8.

Resegotti et al., (1981), "Treatment of Aplastic Anaemia with Methenolone, Stanozolol and Nandrolone. A Report of 130 Cases," *Panminerva Med.*, 23:243-8.

Riechmann et al., (1988), "Reshaping Human Antibodies for Therapy," *Nature*, 332:323-7.

Robinson et al., (1998), "Optimizing the Stability of Single-Chain Proteins by Linker Length and Composition Mutagenesis," *Proc. Natl. Acad. Sci. USA*, 95:5929-34.

Rothmann et al., (1982), "Erythropoietin-Dependent Erythrocytosis associated with Hepatic Angiosarcoma," *J. Surg. Oncol.*, 20:105-8.

Sali et al., (1993), "Comparative Protein Modelling by Satisfaction of Spatial Restraints," *J. Mol. Biol.*, 234:779-815.

Schecter et al., (1997), "Tissue Factor is Induced by Monocyte Chemoattractant Protein-I in Human Aortic Smooth Muscle And THP-I Cells," *J. Biol. Chem.*, 272:28568-73.

Sharp et al., (1988), "Codon Usage Patterns in *Escherichia coli, Bacillus subtilis, Saccharomyces cerevisiae, Schizosaccharomyces pombe, Drosophila melanogaster* and *Homo sapiens*; a Review of the Consdierable Within-Species Diversity," *Nucleic Acids Res.*, 16(17):8207-8211.

Soligo et al., (1998), "Expansion of Dendritic Cells Derived from Human CD34+ Cells in Static And Continuous Perfusion Cultures," *Br. J. Haematol.*, 101:352-63.

Spivak et al., (1989), "The In Vivo Metabolism of Recombinant Human Erythropoietin in The Rat," *Blood*, 73:90-9.

Stumiolo et al., (1999), "Generation of Tissue-Specific and Promiscuous HLA Ligand Databases Using DNA Microarrays and Virtual HLA Class II Matrices," *Nat. Biotech.*, 17(6):555-61.

Suliman et al., (1996), "Cloning of a CDNA Encoding Bovine Erythropoietin and Analysis of Its Transcription in Selected Tissues," *Gene*, 171:275-80.

Takashi et al., (2000), "Immunologic Self-Tolerance Maintained by CD25+ CD4+ Regulatory T Cells Constitutively Expressing Cytotoxic T Lymphocyte-Associated Antigen 4," *J. Exp. Med.*, 192(2):303-309.

Takai, (2002), "Roles of Fc Receptors in Autoimmunity," *Nat. Rev. Immunol.*, 2(8):580-92.

Taniguchi et al., (1980), "Expression of the Human Fibroblast Interferon Gene in *Escherichia coli*," *Proc. Natl. Acad. Sci. USA*, 77:5230-5233.

Thurner, (1999), "Generation of Large Numbers of Fully Mature and Stable Dendritic Cells from Leukapheresis Products for Clinical Application," *J. Immunol. Methods*, 223:1-15.

Tiruppathi et al., (1996), "Isolation and Characterization of a Cell Surface Albumin-Binding Protein from Vascular Endothelial Cells," *Proc. Nat. Acad. Sci. USA*, 93:250-4.

Van Den Eynde et al., (1989), "Presence on a Human Melanoma of Multiple Antigens Recognized By Autologous CTL," *Int. J. Cancer*, 44:634-40.

Van Der Bruggen et al., (1991), "A Gene Encoding an Antigen Recognized by Cytolytic T Lymphocytes on a Human Melanoma," *Science*, 254:1643-7.

Van Heyningen et al., (1982), "Human MHC Class II Molecules as Differentiation Markers," *Immunogenetics*, 16:459-69.

Voest et al., (1995), "Inhibition of Angiogenesis in Vivo by Interleukin 12," *J. Natl. Canc. Inst.*, 87:581-6.

Weitkamp et al., (1973), "Additional Data on the Population Distribution of Human Serum Albumin Genes; Three New Variants," *Ann. Hum. Genet.*, 37:219-26.

Wetzel et al., (2001), "BAY50-4798, an Interleukin-2 (IL_2) Variant, demonstrates Selective Activation of Human and Chimpanzee T Cells Relative to NK Cells but Shows Less Selectivity for T Cells from Monkeys and Rodents," *ASCO Annual Meeting*, Abstract 1051.

Woof et al., (1986), "Localisation of the Monocyte-Binding Region on Human Immunoglobulin G," *Mol. Immunol.*, 23:319-30.

Wyatt et al., (1998), "The Antigenic Structure of the HIV Gp120 Envelope Glycoprotein," *Nature*, 393:705-11.

Wysocka et al., (1995), "Interleukin-12 is Required for Interferon-Gamma Production and Lethality in Lipopolysaccharide-Induced Shock in Mice," *Eur. J. Immunol.*, 25:672-6.

Yan et al., (1996), "Characterization fo an Ig VH Idiotope that Results in Specific Homophilic Binding and Increased Avidity for Antigen," *J. Immunol.*, 157:1582-8.

Yeh et al., (1992), "Design of Yeast-Secreted Albumin Derivatives for Human Therapy: Biological and Antiviral Properties of a Serum Albumin-CD4 Genetic Conjugate," *Proc. Natl. Acad. Sci. USA*, 89:1904-8.

Zhang et al., (1994), "Structure/Activity Analysis of Human Monocyte Chemoattractant Protein-1 (MCP-1) by Mutagenesis. Identification of a Mutated Protein that Inhibits MCP-1-Mediated Monocyte Chemotaxis," *J. Biol. Chem.*, 269:15918-24.

Zhu et al., (2001), "MHC Class I-Related Neonatal Fc Receptor for IgG is Functionally Expressed in Monocytes, Intestinal Macrophages and Dendritic Cells," *J. Immunol.*, 166:3266-3276.

\* cited by examiner

A.

C.

B.

D.

A.

C.

B.

A.

C.

B.

D.

E.

EXPRESSION TECHNOLOGY FOR PROTEINS CONTAINING A HYBRID ISOTYPE ANTIBODY MOIETY

RELATED APPLICATIONS

This application claims priority to, and the benefit of U.S. Ser. No. 60/274,096 filed Mar. 7, 2001, the disclosure of which is incorporated by reference herein in its entirety.

FIELD OF THE INVENTION

The present invention relates generally to methods and compositions for antibodies with moieties deriving from two or more isotypes, and fusion proteins derived therefrom, including proteins containing an antibody moiety with altered effector functions, increased protein expression and/or decreased oligomerization. The invention particularly relates to antibodies and fusion proteins in which a hinge region derives from one isotype and the CH2 domain derives from a different isotype.

BACKGROUND OF THE INVENTION

The efficiency of protein expression from genetically engineered cells is an important commercial concern. Some commercially important proteins are best made from eukaryotic cells, such as mammalian cells, plant cells, or yeast cells, in order to ensure correct folding and glycosylation. However, the cost of maintaining large cultures of eukaryotic cells means that proteins produced in this way are expensive to make. Therefore, there is a need in the art to maximize the expression levels of proteins from eukaryotic cells.

A related issue is that therapeutic proteins produced from eukaryotic cells must be expressed in the correct conformational state. Normally, mechanisms of transcription and translation ensure that a genetically engineered cell will produce a protein whose sequence is determined by the nucleic acid encoding the protein. However, after transcription and translation, the protein may fail to fold properly and may be degraded. Alternatively, a protein may be produced in an aggregated state, such that activity is reduced. Even if an aggregated protein is active, it may be pharmacologically unacceptable due to increased immunogenicity compared to a non-aggregated protein. Thus, a pharmacologically acceptable protein preparation should generally be substantially free of aggregated proteins.

The amount of a protein that is expressed from a genetically engineered eukaryotic cell is a function of the rate of transcription of the encoding gene, the efficiency of mRNA splicing and of export from the nucleus, and the efficiency of translation. The role that these events play in protein expression is sufficiently well understood that one skilled in the art of genetic engineering and protein expression can generally incorporate appropriate nucleic acid sequences into the design of an expression construct with efficient transcription, splicing, mRNA export, and translation.

However, the amount of a correctly folded, non-aggregated protein that is produced from a eukaryotic cell is also a function of the amino acid sequence of the protein, as well as the nucleic acid sequences that determine transcription, splicing, mRNA export, translation, and post-translational modification. For example, it is thought that a significant fraction of proteins synthesized in a cell is degraded. The features in a protein that determine whether or not it should be degraded are currently subject to intensive study, but presently it is not possible to predict the efficiency of protein folding, degradation, or aggregation by simply examining the sequence of a protein. Some naturally occurring proteins fold efficiently, are resistant to proteolysis, and do not aggregate. In contrast, other proteins fold inefficiently, are rapidly degraded, and aggregate.

Antibodies and artificial proteins containing a portion of an antibody, termed antibody fusion proteins or Ig fusion proteins herein, are useful for a variety of purposes relating to the targeting capability of antibody variable domains as well as the ability of the constant regions to bind to various other proteins. Antibody and antibody fusion protein preparations are particularly useful when they are correctly folded and non-aggregated. Therefore there is a need in the art for methods and compositions for the production of antibody and antibody fusion protein preparations with reduced aggregation.

Additionally, antibodies and antibody fusion proteins are useful since their ability to bind to various other proteins enables them, for example, to elicit specific effector functions. In some instances specific effector functions are desirable but often the loss of effector functions is preferable. The antibody component of a fusion protein may be altered to reduce or eliminate effector functions by utilizing a modified antibody. Antibody and antibody fusion protein preparations are also useful when they are modified to alter functionality. Therefore there is a need in the art for methods and compositions for the production of modified antibodies and antibody fusion proteins with altered effector functions.

Protein drugs can be degraded by proteases, such that their delivery and pharmacokinetic properties are suboptimal. There is a need in the art for improvement of protein drugs that have the useful properties of certain proteins, but that have greater protease resistance.

SUMMARY OF THE INVENTION

The present invention features methods and compositions useful for producing intact antibodies, immunocytokines, immunofusins, immunoligands, and other antibody and Fc fusion proteins that enhance the expression, proper oligomerization, purification, and protease resistance of a desired fusion protein optionally with modified, combined, or decreased Fc effector functions. Specifically, the invention provides antibody moieties with hybrid isotypes, optionally using mutant Ig components for use in intact antibodies and in fusion proteins containing an antibody moiety.

IgG/IgG Hybrid Isotypes

In one set of preferred embodiments, the invention provides fusion proteins with decreased effector functions and improved assembly. Such fusion proteins are particularly useful when the Ig moiety serves to enhance expression and improve serum half-life, but when the immunological functions of the Ig moiety are not needed.

In these embodiments, the fusion protein preferably comprises CH1, CH2, and/or CH3 domains of an IgG2 or IgG4, combined with a hinge region from IgG1 or a hinge region from IgG4, the latter hinge region preferentially comprising a mutation that enhances correct formation of disulfide bonds between heavy chain-derived moieties (Angal S, et al. Mol Immunol 1993 Jan.;30(1):105–8). Fusion proteins of this embodiment facilitate high-level expression and improve the correct assembly of intact antibodies and Ig fusion proteins containing Fc regions.

In a more preferred embodiment, the fusion proteins also contain one or more mutations in the Ig moiety. For example, the Ig moiety is mutated to further reduce any remaining effector function that is not desired. For example, the C1q binding site in the CH2 domain of IgG2 is mutant. For example, normal IgG4 does not bind complement because it contains a serine instead of a corresponding proline at position 331 in IgG1 (Eu nomenclature)(Tao, M A et al (1993) J. Exp. Med. 178:661–667; Brekke, O H et al (1994) Eur. J. Immunol. 24:2542–2547); a similar mutation in IgG2 reduces C1q binding. Other residues known to be involved in C1q binding could be modified such as residues at positions 318, 320, 322 and 297 (Duncan A R (1988) Nature: 332:738–740), resulting in a decrease in C1q binding.

In another set of preferred embodiments, a mutation in the hinge region is also present. For example, in cases where an antibody light chain is also present, a form of an IgG1 hinge region with the cysteine residues in the normal number at their normal positions is preferred. However, in cases where an antibody light chain is not present as a distinct polypeptide chain, an IgG1 hinge in which the first cysteine is mutated to another residue is preferred. For example, it is useful to employ such a mutated hinge region in Fc-X proteins, X-Fc proteins, and in single-chain antibodies in which the light chain variable region is attached to the heavy chain by means of a polypeptide linker. The first cysteine in the IgG1 hinge is preferably mutated to a serine in this context.

In a second class of embodiments involving a mutant hinge region, a mutant form of the IgG4 hinge that allows efficient disulfide bonding between the two heavy chains is used.

In a third class of embodiments involving a mutant hinge region, a mutant form of the IgG2 hinge, in which the first two cysteines are each mutated to another amino acid, is used in a hybrid isotype antibody or Ig fusion protein. It is also convenient to use such a mutant hinge in an antibody or Ig fusion protein that is entirely derived from IgG2. For example, a modified IgG2 hinge with the sequence ERKSS-VECPPCP (SEQ ID NO: 1) is used in the context of an antibody or Ig fusion protein. Another useful type of hinge is a hybrid between the IgG2 hinge and the IgG4 hinge, such as the sequence ESKYG-VECPPCP (SEQ ID NO: 2), in which the 5 amino acids before the dash are derived from IgG4 and the remaining amino acids are from IgG2. These embodiments are particularly useful in the context of antibodies and Ig fusion proteins expressed and secreted from eukaryotic cells, because these hinge embodiments promote correct assembly of the proteins. These embodiments may be used as an alternative to the IgG1 hinge. A key feature of these embodiments of an antibody hinge is that they only have two cysteine residues.

Yet another class of embodiments involve mutations in the Ig moiety of hybrid isotype Ig fusion proteins at the junction between the Ig and non-Ig moieties. In one embodiment, the alterations in the amino acid sequence of the fusion protein are preferentially at the junction of the Ig moiety and the non-Ig moiety and preferably lie within 10 amino acids of the junction point. More preferably, the amino acid changes involve changing the C-terminal lysine of the antibody moiety to a hydrophobic amino acid such as alanine or leucine.

An alternative embodiment is useful in circumstances where it is desirable to shorten the half-life of a fusion protein. IgG3 has a short half-life relative to other IgG isotypes due to a modification in the FcRn/FcRp binding site located in the CH3 domain (H435 to R)(see Ward, E S. and Gheti, V [1995] Therapeutic Immunology 2:77–94). A fusion protein with IgG3 CH2 and CH3 domains may be used when short term exposure is desirable. According to this embodiment, it is useful to use an IgG3 CH3 domain in combination with an IgG1 hinge; such an IgG1(hinge)-IgG3 (CH3) fusion protein has superior expression and assembly properties compared to an Ig fusion protein containing an IgG3 hinge and an IgG3 CH3 domain.

In a more preferred embodiment of an Ig fusion protein designed to have a short serum half-life, reduced effector functions, and efficient assembly, a hybrid Ig region is used in which the hinge region derives from IgG1, the CH2 domain derives from IgG2, and the CH3 domain derives from IgG3.

IgG/IgA Hybrid Isotypes

A distinct embodiment of the invention provides hybrid isotype Ig fusion proteins with enhanced protease resistance and enhanced serum half-life. This embodiment is particularly useful in situations in which an Ig fusion protein is exposed to an environment rich in proteases, such as the gut or another mucosal tissue, for example during oral delivery of a Ig fusion protein drug. According to this embodiment, an Ig fusion protein containing elements of the IgG and IgA constant regions is provided. In a preferred embodiment, the hinge of IgA1 and the CH2 and CH3 domains of an IgG are used. In a distinct preferred embodiment, the segments of amino acids encoding the O-linked glycosylation sites in the Fc region of IgA are grafted into the Fc region of an IgG.

IgG/IgM Hybrid Isotypes

Yet another embodiment of the invention provides hybrid isotype antibodies and Ig fusion proteins with oligomerization features of IgA or IgM but with effector functions characteristic of IgG. For example, a protein comprising the hinge region and CH2 domain of IgG1 or IgG3 fused to the CH3 and CH4 domain of IgM is provided. In a more preferred embodiment, an antibody comprising heavy and light chain variable regions and also comprising an IgG hinge and CH2 region fused to the CH3 and CH4 domain of IgM is provided. In an alternative more preferred embodiment, an Ig fusion protein of the form X-Fc is provided, in which X is preferably a ligand for a cell-surface receptor, and the Fc moiety comprises the CH3 and CH4 domain of IgM. Such a molecule combines the ADCC effector function of an IgG with the high valency of IgM.

In a preferred embodiment of a hybrid isotypes using the CH4 domain of IgM or IgA, the C-terminal cysteine in the CH4 domain is mutated to block disulfide bonding to the J chain. This reduces secretion of the Ig fusion protein into the gut.

Preferred Non-Ig Moieties

The preferred type of non-Ig moiety in the fusion proteins of the invention is a protein or moiety that is normally extracellular when not part of an Ig fusion protein. For example, a hormone, cytokine, chemokine, secreted enzyme, or extracellular portion of a trans-membrane receptor.

In a preferred embodiment, the non-immunoglobulin component is a protein such as an anti-obesity protein. For example, the non-immunoglobulin component is leptin, CNTF, CLC/CLF-1 or a portion of Acrp30.

In yet another preferred embodiment, the non-immunoglobulin component is a protein such as erythropoeitin or EPO.

In an alternative embodiment, the non-immunoglobulin component of the fusion protein is a hormone. For example, the non-immunoglobulin component may be insulin, growth hormone, or glucagon-like peptide 1(GLP-1).

In another embodiment, the non-immunoglobulin component of the fusion protein is a cytokine. The term "cytokine" is used herein to describe naturally occurring or recombinant proteins, analogs thereof, and fragments thereof that elicit a specific response in a cell which has a receptor for that cytokine. Preferably cytokines are proteins that may be produced and secreted by a cell. Preferably, cytokines include interleukins such as interleukin-2 (IL-2), IL-4, IL-5, IL-6, IL-7, IL-10, IL-12, IL-13, IL-14, IL-15, IL-16 and IL-18, hematopoietic factors such as granulocyte-macrophage colony stimulating factor (GM-CSF), G-CSF and erythropoietin, tumor necrosis factors (TNF) such as TNFα, lymphokines such as lymphotoxin, regulators of metabolic processes such as leptin, interferons such as interferon α, interferon β, and interferon γ, and chemokines. Preferably, the Ig-cytokine fusion protein of the present invention displays cytokine biological activity.

In an alternative preferred embodiment, the non-immunoglobulin component of the fusion protein is a ligand-binding protein with biological activity. Such ligand-binding proteins may, for example, (1) block receptor-ligand interactions at the cell surface; or (2) neutralize the biological activity of a molecule (e.g., a cytokine) in the fluid phase of the blood, thereby preventing it from reaching its cellular target. Preferred ligand-binding proteins include CD4, CTLA-4, TNF receptors, or interleukin receptors such as the IL-1 and IL-4 receptors. Preferably, the antibody-receptor fusion protein of the present invention displays the biological activity of the ligand-binding protein. One highly preferred embodiment comprises the extracellular TNF-receptor domain fragment used in the protein drug Enbrel, in the format TNFR-hinge-CH2-CH3 or hinge-CH2-CH3-TNFR, in which the CH2 and CH3 domains are derived from IgG2 or IgG4 and each of the two hinge regions in the dimeric Fc has three or fewer cysteines, and even more preferably, two or fewer cysteines.

Another type of preferred ligand-binding protein has the capacity to bind to small molecules rather than proteins. For example, it is convenient to fuse avidin to a hybrid isotype Ig moiety, such as an antibody. The hybrid isotype antibody-avidin fusion is then administered to a mammal such as a mouse or human and becomes concentrated in a target tissue of the body, as determined by the specificity of a V region of the antibody. After the antibody-avidin fusion protein has sufficiently cleared from the body, a conjugate of biotin and a therapeutic molecule is administered. The biotin conjugate becomes concentrated in the target tissue by virtue of binding to avidin, which results in a lessening of side effects that could arise from a concentration of the therapeutic molecule in non-target tissues. This strategy can be used with other ligand/ligand-binding protein pairs.

Another type of preferred non-immunoglobulin moiety is an enzyme. For example, an enzyme with a distinctive specificity may be fused to a hybrid isotype Ig moiety, such as an antibody. The hybrid isotype antibody-enzyme fusion is then administered to a mammal such as a mouse or human and becomes concentrated in a target tissue of the body, as determined by the specificity of a V region of the antibody. In one preferred treatment method of the invention, after the antibody-enzyme fusion protein has sufficiently cleared from the body, a prodrug that can be cleaved into an active form by the enzyme is administered. The activated drug becomes concentrated in the target tissue, which results in a lessening of side effects that could arise from a concentration of the activated drug molecule in non-target tissues. In a highly preferred form of this embodiment, the activated drug is an anticancer drug, such as a cytotoxic agent. In an alternative highly preferred embodiment, the enzyme itself has a therapeutic activity. For example, an RNAse such as Onconase is coupled to a hybrid isotype antibody fusion protein and targeted to a tumor via an antibody V region.

Nucleic Acids

This invention also provides novel nucleic acid sequences that facilitate the expression and secretion of Ig fusion proteins and intact antibodies with hybrid isotypes, as well as methods for the construction of such nucleic acids.

A particularly useful feature of genomic sequences encoding antibody proteins is that the variable region, CH1, hinge, CH2, CH3, and CH4 regions are encoded by separate exons. This feature facilitates the engineering of hybrid isotype Ig fusion proteins by 'exon shuffling' (Zuckier et al., Cancer Research [1998] 58:3905–8; Poon et al., J. Biol. Chem. [1995] 270:8571–7; Jefferis R, et al., Mol Immunol.[1990] 27:1237–40; Chappel M S, Proc Natl Acad Sci U S A. [1991] 88:9036–40; Senior B W, et al., Infect Immun. [2000] 68:463–9.).

For Fc fusion proteins, nucleic acid molecules can encode the protein in various configurations. In a preferred set of embodiments, a nucleic acid molecule encodes, serially in a 5' to 3' direction, (i) a signal sequence, an immunoglobulin Fc region and a target protein sequence or (ii) a signal sequence, a target protein, and an immunoglobulin Fc region, or (iii) a signal sequence, a first target protein, an immunoglobulin Fc region, and a second target protein. The resulting nucleic acid molecule thereby encodes an Fc-X, X-Fc, or X-Fc-Y structure where X and Y are a target protein or proteins. For example, X and Y may themselves be fusion proteins. Linkers are optionally encoded between these moieties.

Similarly, according to the invention, nucleic acids encoding whole antibody Ig fusion proteins are designed to encode a signal sequence at the N-terminus of each heavy chain moiety and each light chain moiety.

A nucleic acid of the invention can be incorporated in functional association into a replicable expression vector which can then be introduced into a eukaryotic host cell competent to produce a fusion protein. The resultant Ig fusion proteins are produced efficiently and secreted from the eukaryotic host cells. Secreted Ig fusion proteins may be collected from the culture media without lysing the eukaryotic host cell. The protein product can be assayed for activity and/or purified using common reagents as desired, and/or cleaved from the fusion partner, all using conventional techniques. Alternatively, a nucleic acid of the invention may be introduced into a bacterial cell, and the resulting Ig fusion protein purified according to standard techniques.

The invention also provides methods of enhancing the levels of antibodies and Ig fusion proteins produced in cells. The method is preferably applied to production in eukaryotic cells, preferably mammalian cells. For example, according to the method, the production of a starting antibody or Ig fusion protein is improved by exchanging nucleic acid sequences encoding domains of the Ig moiety with corresponding sequences encoding domains from other antibody isotypes, or with mutant sequences, comparing expression levels by assaying the production of the altered protein as described herein, and choosing particular expression constructs that give the highest levels. This process may be used iteratively. It is particularly useful to interchange hinge regions.

Treatment

The invention also provides methods of treatment using the modified antibodies and Ig fusion proteins. Accordingly, the invention provides processes that are both efficient and inexpensive as well as proteins that are less immunogenic.

The foregoing and other objects, features and advantages of the present invention will be made more apparent from the detailed description, drawings, and claims that follow.

BRIEF DESCRIPTION OF THE DRAWINGS

FIG. 1A shows an IgG1 isotype.

FIG. 1B shows an IgG2 isotype.

FIG. 1C shows an isotype hybrid with an IgG2 and an IgG1 hinge having a mutation of the first cysteine.

FIG. 1D shows an IgG hybrid γ1(CH1-H) γ2(CH2-CH3).

FIG. 2A shows an Ig fusion protein in the Fc-X configuration comprising a hinge from one antibody isotype and an Fc moiety consisting of a CH2 and CH3 domain from a second isotype; at the C-terminus of the Fc moiety is a protein moiety "X".

FIG. 2B shows an Ig fusion protein in the X-Fc configuration comprising a hinge from one antibody isotype and an Fc moiety consisting of a CH2 and CH3 domain from a second isotype; at the N-terminus of the Fc moiety is a protein moiety "X".

FIG. 2C shows an Ig fusion protein in the X-Fc-Y configuration comprising a hinge from one antibody isotype and an Fc moiety consisting of a CH2 and CH3 domain from a second isotype; at the N-terminus of the Fc moiety is "X", which can be any protein, and at the C-terminus of the Fc moiety is a protein moiety "Y".

FIG. 3A shows an Ig fusion protein comprising a hinge from one antibody isotype (black) and CH1, CH2, and CH3 regions from a different isotype; a non-Ig protein "X" is fused at the C-terminus of the heavy chain.

FIG. 3B shows an Ig fusion protein comprising a hinge from one antibody isotype (black) and CH1, CH2, and CH3 regions from a different isotype; a non-Ig protein "X" is fused at the C-terminus of the heavy chain; arrows indicate a subset of possible sites of mutation in the antibody moiety, as described herein.

FIG. 3C shows an Ig fusion protein comprising a hinge and a CH1 region from one antibody isotype (black) and CH2, and CH3 regions from a different isotype; a non-Ig protein "X" is fused at the C-terminus of the heavy chain; the branched structure emanating from the hinge represents a glycosylation moiety.

FIG. 3D shows an Ig fusion protein comprising a hinge from one antibody isotype (black) and CH1, CH2, and CH3 regions from a different isotype; a non-Ig protein "X" is fused at the C-terminus of the heavy chain; a second non-Ig protein "Y" is fused at the N-terminus of the light chain.

DEFINITIONS

Figure 1:
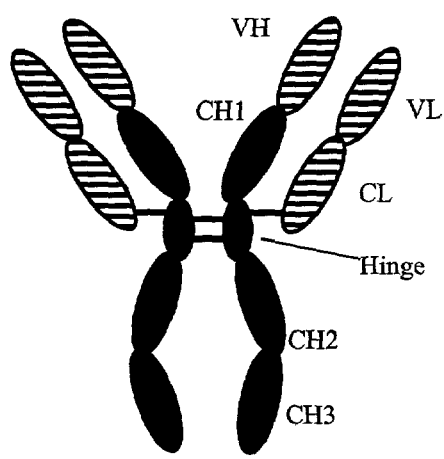
FIGS. 1A–D are schematic illustrations of IgG hybrid isotypes used to prepare fusion proteins in accordance with certain aspects of the invention; the thick lines represent disulfide bonds connecting cysteine residues; antibody domains are indicated in FIG. A; IgG1 domains are shown in black, IgG2 domains are shown in white, and variable and light chain domains are shown striped.
Figure 1:
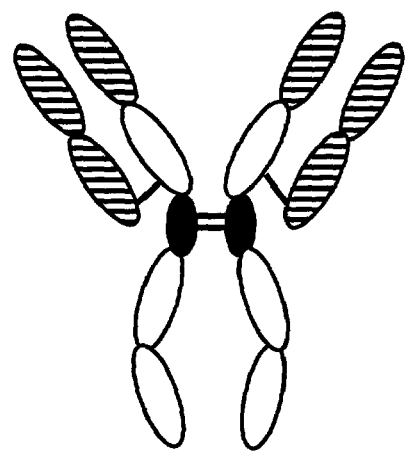
Figure 1:
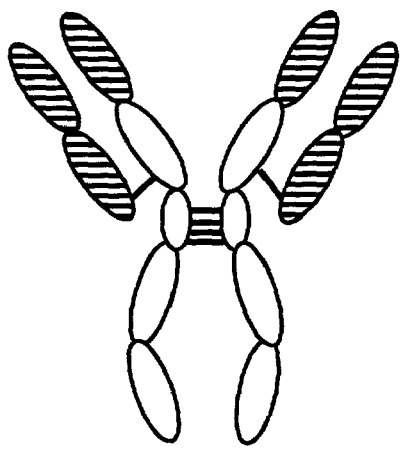
Figure 1:
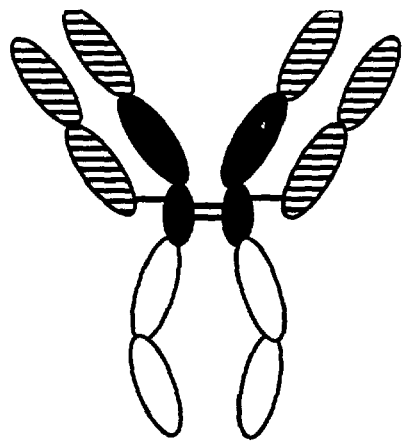
Figure 2:
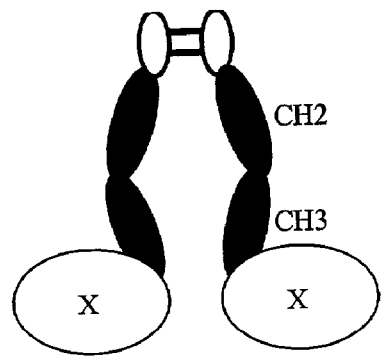
FIGS. 2A–C are schematic illustrations of Ig fusion proteins comprising Fc regions that contain hybrid isotypes; "X" and "Y" may be any non-Ig moiety.
Figure 2:
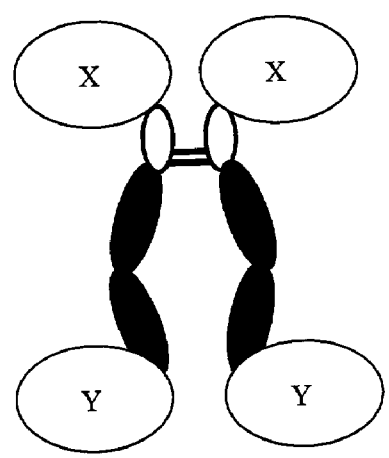
Figure 2:
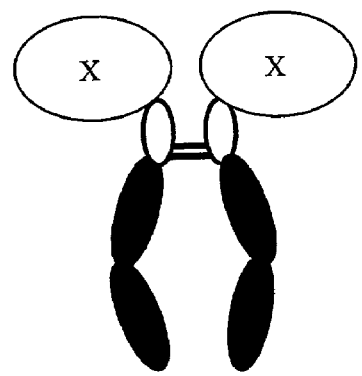
Figure 3:
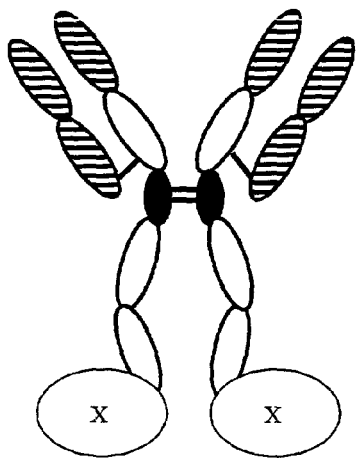
FIGS. 3A–D are schematic illustrations of Ig fusion proteins that comprise variable regions and that contain hybrid isotypes; "X" and "Y" may be any non-Ig moiety.
FIG. 3E shows an Ig fusion protein comprising a hinge from one antibody isotype (black) and CH1, CH2, and CH3 regions from a different isotype; a non-Ig protein "X" is fused at the C-terminus of the heavy chain; a second non-Ig protein "Y" is fused at the N-terminus of the heavy chain.
Figure 3:
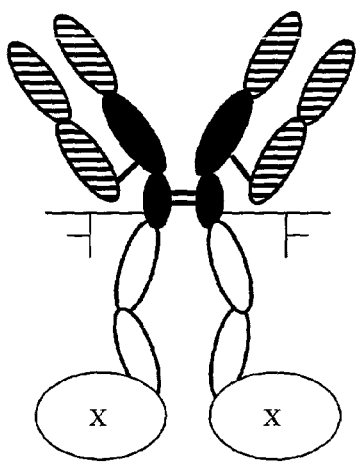
Figure 3:
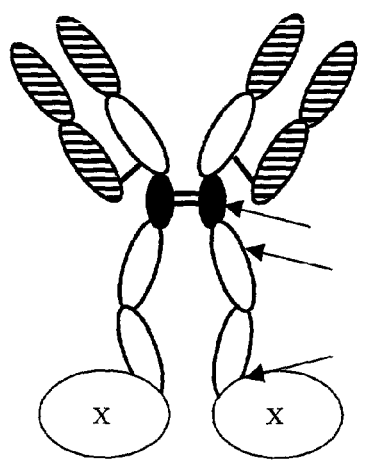
Figure 3:
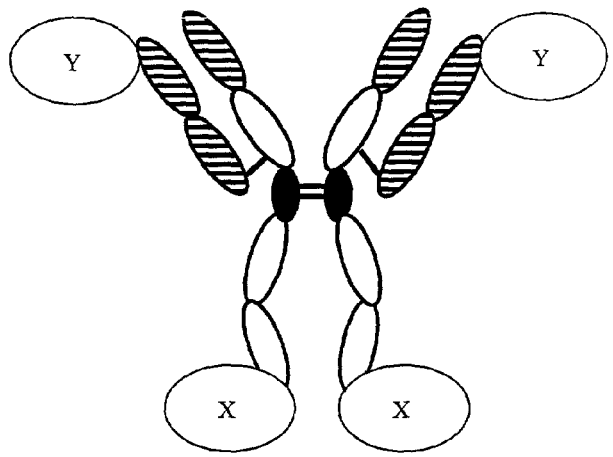
Figure 3:
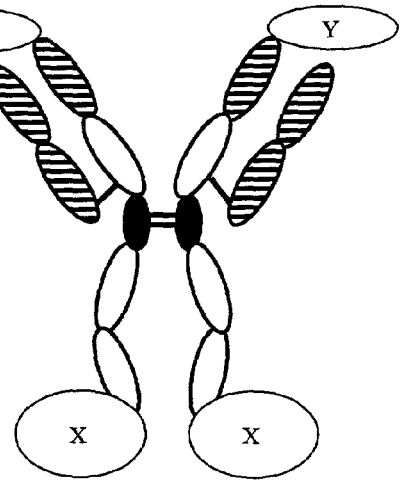

According to the invention, by isotype is meant the class of heavy chain constant (C) region of an immunoglobulin which determines the functional activity of an antibody. There are five major classes including IgA, IgG, IgM, IgD, and IgE.

By IgA is meant the class of immunoglobulin characterized by α heavy chains.

By IgD is meant the class of immunoglobulin characterized by δ heavy chains.

By IgE is meant the class of immunoglobulin characterized by ε heavy chains.

By IgM is meant the class of immunoglobulin characterized by μ heavy chains.

By IgG is meant the class of immunoglobulin characterized by γ heavy chains.

"Gamma1" or "γ1" refers to a heavy chain or portion thereof derived from an IgG1. Similarly, "gamma2" or "γ2" derives from IgG2, and so on.

According to the invention, by allotype is meant allelic polymorphisms of the same heavy chain C gene of an immunoglobulin. These determinants are found in some, but not all, members of a species.

According to the invention, by idiotype is meant antigenic determinants found on the variable (V) regions of antibodies and are due to particular rearranged $V_H$ and $V_L$ genes.

According to the invention, by FcRn, also know as FcRp, is meant the beta-2 microglobulin-containing neonatal intestinal transport receptor which regulates the clearance of IgG and is important for the in vivo circulating half-life of antibodies.

According to the invention, by FcγR is meant cell surface receptors, including FcγRI, RII, and RIII, that bind the Fc portion of IgG molecules and elicit effector cell functions. FcγR are expressed on phagocytes, B lymphocytes, NK cells and dendritic cells.

According to the invention, by "an IgG1," or "IgG2," or other Ig molecule is meant a whole antibody including a heavy and light chain, or a portion thereof.

According to the invention, by "a bivalent monomer" is meant an antibody, Fc fusion, or antibody fusion that is normally dimerized by the formation of disulfide bonds that form in a normal antibody. The formation of such disulfide bonds is generally inferred by the ability of an Fc-containing protein to migrate on a denaturing, non-reducing SDS gel as a single band with an apparent molecular weight about twice that of the apparent molecular weight seen with reducing conditions. The presence of a bivalent monomer is also inferred by the presence of a peak in a size exclusion chromatograph that corresponds to the correct molecular weight. Other protein sizing methods may also be used to identify the presence of bivalent monomers.

According to the invention, by "an Ig fusion protein" is meant a fusion protein that contains part or all of an antibody linked to a second moiety which is preferably part or all of a non-antibody or non-immunoglobulin (non-Ig) protein. Immunocytokines, Fc-X proteins, X-Fc proteins, and X-Fc-Y proteins are all examples of Ig fusion proteins. Similarly, fusion proteins in which a non-Ig moiety is placed between two Ig moieties or domains constitute a type of Ig fusion protein.

According to the invention, by "assembly" of a protein is meant the proper folding of a protein and oligomerization into a correct multimeric state. Assembly can be monitored in many ways that are established in the art. In practice, correct assembly of a protein, with respect to disulfide bonds, can be conveniently monitored by comparing migration on a non-reducing and reducing SDS gel: if a given protein species forms multiple bands on a non-reducing gel, but forms a single band on a reducing SDS gel, it can be inferred that at most only one of the bands on the non-reducing SDS gel is the correctly assembled species. Alternatively, size exclusion chromatography can be used to distinguish unit proteins from higher-order oligomers and aggregates that may form from incorrect disulfide bonding or non-covalent interactions.

According to the invention, by "domain" of an antibody moiety is meant a structural domain that corresponds to the amino acid segments encoded by individual exons in antibody genes in humans. For example, the constant domains of an IgG are the CH1, hinge, CH2, and CH3 domains. In some cases, the hinge and CH2 domains are encoded by the same exon. In such cases, a junction between the hinge and CH2 domain is defined by alignment with other hinge/CH2 junctions (see Paul, op cit., p. 46–49).

According to the invention, by domain, protein, region, or molecule is meant an entire domain, protein, region, or molecule, or a portion, mutant or engineered form thereof, or a form principally derived therefrom. The portion, mutant, or engineered form preferably has functional properties characteristic of the entire domain, protein, region, or molecule. According to the invention, by "principally deriving" is meant having at least 95% of its amino acids deriving from a particular sequence of a naturally occurring protein or domain. For example, a sequence that principally derives from the human IgG2 CH2 domain is at least 95% identical to human IgG2 CH2 domain in an amino acid alignment.

According to the invention, by "modified IgG1 hinge" is meant a hinge region from IgG1 in which a cysteine, preferably the first cysteine is mutated to another amino acid. This cysteine normally forms a disulfide bond to the antibody light chain. The modified IgG1 hinge is particularly useful in proteins that either lack the light chain or that have another cysteine that can bond to the light chain.

According to the invention, by "an erythropoietin molecule" is meant a molecule that has generally the same structure and similar amino acid sequence to a vertebrate erythropoietin, optionally including mutations. For example, Example 18 describes the use of human erythropoietin without mutations and of a version of human erythropoietin with four mutations.

DETAILED DESCRIPTION OF THE INVENTION

The present invention provides methods and compositions for improving the in vivo and in vitro production of immunoglobulin fusion proteins. In particular, the invention provides useful methods for improving the expression, aggregation, and/or folding properties of immunoglobulin fusion proteins. The invention is based in part on the surprising observation that an immunoglobulin fusion protein is expressed at a higher level, with fewer aggregation and/or folding problems, when a hybrid immunoglobulin is used as the fusion partner instead of a wild-type immunoglobulin. The improved fusion protein production properties associated with hybrid immunoglobulins are unexpected since wild-type immunoglobulins such as IgG1 and IgG2 are thought to be well folded proteins that are expressed efficiently both in vivo and in vitro.

Accordingly, one aspect of the invention includes methods and compositions useful for expressing immunoglobulin fusion proteins that include a hybrid immunoglobulin (or hybrid Ig) moiety. Preferred hybrid immunoglobulins include an IgG1 hinge and an IgG2 CH2 and CH3 domains. Other preferred hybrids include IgG1 and IgG4 domains.

Antibody Structure

Antibodies are Y shaped molecules and are composed of two heavy (H) and two light (L) chains. Each heavy chain is linked to a light chain by a disulfide bond and relies on covalent and noncovalent interactions to properly orient the two chains relative to each other. The variable domains at the amino termini of these two chains contain the antigen-binding site and, with the CH1 domains, define the Fab end of the molecule.

The four chains use hydrophobic bonding between the heavy chains and one or more interchain disulfide bonds to stabilize the complex. Thus the complete immunoglobulin is bivalent with two identical antigen-binding sites. Certain immunoglobulins normally undergo additional multimerization, such as IgM and IgA.

Each polypeptide chain has two to five domains; the light chains contain two domains while the heavy chains contain four or five. The single amino terminal domain of each chain is termed variable due to extensive sequence variation, while the several carboxy-terminal domains are referred to as the constant regions. Heavy chain regions are numbered CH1, hinge, CH2, CH3, CH4 and are responsible for many important antibody functions including Fc receptor (FcR) binding and complement fixation.

There are five major isotype classes of heavy chain C regions, classified as IgA, IgG, IgD, IgE, IgM, each with characteristic effector functions (IgG is separated into four γ isotype subclasses: γ1, γ2, γ3, γ4). The constant regions of the light chain possess only one C domain and can be one of the two classes, Ck and Cλ, which have no known distinct functional attributes (see, W. E. Paul, ed., 1993, Fundamental Immunology, Raven Press, New York, N.Y).

All immunoglobulins have a hinge region located C terminal to the CH1 domain of their heavy chains separating the Fab and Fc regions of the molecule. In most cases, the hinge regions permit a large degree of flexibility between the antigen binding (Fab end) and effector-interaction (Fc) components of the molecule, thereby linking the two key functional elements of the antibody. In the IgG isotypes, interchain disulfide bonds typically form within this hinge region, generating the final tetrameric molecule.

Except for IgM, the hinge region is dominated by prolines, serines and threonines, amino acids that tend to prevent formation of secondary structures and that are thought to give hinges flexibility. The IgG1 isotype, often used for fusion proteins, has two disulfide bonds in the hinge region that link the heavy chains to one another. In contrast, the IgG2 isotype has four disulfide bonds (FIG. 1). According to the invention, these disulfide bonds tend to promote incorrect assembly of antibodies and Ig fusion proteins, as shown in the unexpected findings in the Examples.

Useful Configurations of Ig Fusion Proteins

Immunocytokines are only one example of a tumor-targeted fusion protein therapy for which methods and compositions of the invention are useful. Other tumor-toxic molecules may also be targeted to tumors by fusion to tumor-specific antibodies according to the invention. In addition, other types of diseased cells, such as virus-infected cells, may be attacked by antibody fusion proteins according to the invention.

Methods and compositions of the invention are also useful in combination with the use of Fc-X and X-Fc technology. According to the invention, the use of hybrid antibody isotypes in a fusion protein further improves the production and collection of a target protein or polypeptide of interest that is linked to the Fc portion of an immunoglobulin. For Fc-X fusion proteins, a signal peptide, followed by the Fc fragment of an immunoglobulin gene is the N-terminal fusion partner to the target protein. The fusion protein is then expressed in a host cell, for example a mammalian cell such as a cell that naturally expresses the immunoglobulin. The signal peptide-Fc fragment in the a N-terminal fusion partner directs the target protein through the secretory pathway such that the fusion protein is readily secreted. Additionally, use of the Fc fragment, which is normally glycosylated and highly charged at neutral pH, facilitates solubilization of more hydrophobic proteins. The targeting of Fc-X fusion proteins through the secretory pathway also alleviates problems associated with protein toxicity inside the cell and facilitates the isolation of stable cell lines. The fusion protein product is easily assayed and purified as it is readily collected from the culture media in its native conformation with retention of both biological and enzymatic activities. The efficacy of this technology has been demonstrated with Fc-leptin and Fc-erythropoietin. Some of these advantages are also inherent in X-Fc proteins.

According to the invention, examples of useful fusions of antibody moieties include Fc-X, X-Fc, and X-Fc-Y proteins. Such proteins contain an Fc region with a non-antibody protein or protein fragment fused at the N-terminus, the C-terminus, or both the N-terminus and C-terminus. One advantageous effect of fusion to the Fc region is that the serum half-life of the fusion partner can be significantly extended. A second advantageous effect is that an 'X' can be effectively dimerized by attachment to the Fc. For example, Enbrel is a fusion protein consisting of a portion of a TNF receptor and a human IgG1 Fc region.

In some embodiments of the invention, it is specifically advantageous to engineer a fusion protein with hybrid isotypes in the X-Fc orientation. With these constructs the target protein is the N-terminal fusion protein and the Fc fragment follows. For some proteins this approach may be useful, for example with lymphocyte cell surface glycoprotein (LHR) (see U.S. Pat. No. 5,428,130).

According to the invention, the utility of recombinant antibody-based fusion proteins, albeit better than protein or cytokine treatments alone, may be limited by their rapid in vivo clearance from the circulation since antibody fusion proteins have a significantly lower in vivo circulating half-life than the free antibody. The decreased circulating half-life is likely a result of increased clearance via the Fc receptor (FcR). Switching of isotype has proven to be one mechanism by which features such as half-life can be altered. Improvements in the half-lives of two immunocytokines have been demonstrated (Cancer Research 59(9): 2159–66, 1999) by changing the isotype of the human heavy chain C region from IgGγ1 or IgG γ3 to IgG γ4, an isotype with reduced FcR binding. The IgG4-based immunocytokines and fusion proteins have 10-fold reduced FcR binding and reduced Fc receptor effector functions such as ADCC, but still show similar or better efficacy in mouse tumor models than that of the original IgGγ1 based fusion proteins. However, the invention provides fusion proteins based on hybrid antibodies that combine functional and structured properties of different antibody types in a single molecule.

Accordingly, for certain applications, the IgG2 isotype confers superior qualities to the antibody fusion protein since the IgG2 isotype has greatly reduced Fc receptor binding (Hulett et al. [1994] Adv. Immunol.57:1127). As with whole antibody fusion proteins, it is sometimes advantageous to use a γ2 isotype in fusion proteins containing only an Fc region. The rationale is the same as for whole antibodies: it is often desirable to avoid the binding to Fc receptors that is mediated by Fc regions derived from other isotypes.

However, the use of the IgG2 isotype in a fusion protein generally causes some level of inappropriate assembly, as described herein. Methods and compositions of the invention provide antibody fusion proteins that have the minimized effector functions of the IgG2 isotype, but which do not have the aggregation properties of this isotype.

According to the invention, novel hybrid isotype antibodies and fusion proteins show enhanced expression and improved assembly over that of IgG2-based fusion proteins. Additionally, hybrid isotype antibodies and fusion proteins may have increased efficacy in therapeutics where Fc receptor effector functions are not desired.

Types of Hinges

Hybrid isotype antibodies of the invention also include antibodies wherein the hinge region is a mutant hinge region, preferably a hinge region with a reduced number of cysteine residues, for example, a modified IgG1 hinge region in which the first cysteine is mutated to serine. The first cysteine of the IgG1 hinge region normally bonds to the light chain. In an Fc-X protein or an X-Fc protein or any other antibody fusion protein lacking a light chain, this cysteine does not serve its natural function and therefore can be mutated. However, according to the invention, a hybrid isotype antibody with an IgG1 hinge missing the first cysteine and an IgG2 CH1 domain can associate with a light chain, because the light chain normally forms a disulfide bond with a cysteine within the IgG2 CH1 domain. The four cysteines within the IgG2 hinge are thought to form disulfide bonds with each other.

According to the invention, the cysteines in a hinge region of an antibody or Ig fusion protein that are involved in heavy chain-heavy chain homodimerization can have significant effects on the expression and assembly of antibodies or Ig fusion proteins. In particular, a higher number of cysteines can lead to incorrect assembly of an antibody or Ig fusion protein, due to incorrect disulfide bond formation. Thus, the invention discloses that mutation of one or more cysteines involved in heavy chain homodimerization can cause an improvement in expression or assembly of an antibody or Ig fusion protein. In a preferred embodiment, a heavy chain-homodimerization cysteine can be mutated to, in order of general preference, serine, alanine, threonine, proline, glutamic acid, glutamine, lysine, histidine, arginine, asparagine, aspartic acid, glycine, methionine, valine, isoleucine, leucine, tyrosine, phenylalanine, tryptophan or selenocysteine.

It is particularly convenient to use an IgG1 hinge that is mutated in the first, most N-terminal cysteine. The advantage of this hinge region is that it only has two cysteines. The first cysteine in the IgG1 hinge normally forms a disulfide bond with the a cysteine in the light chain. However, in Ig fusion proteins lacking a light chain, such as Fc-X, X-Fc and X-Fc-Y proteins, the most N-terminal cysteine in the IgG1 hinge serves no such purpose and therefore can be mutated (Lo et al. Protein Engineering 11:405–500 [1998]). As described in the Examples, the two-cysteine IgG1 hinge can also be used in an intact antibody or intact antibody fusion protein in which the CH1 domain derives from IgG2, since the IgG2 CH1 domain has a cysteine that can form a disulfide with the light chain.

Fc Receptors

IgG molecules interact with multiple classes of cellular receptors including three classes of Fcγ receptors (FcγR) specific for the IgG class of antibody, namely FcγRI, FcγRII, and FcγRIII. These receptors are responsible for uptake of antigen-antibody complexes. The Fc receptor binding site on Fc is found on the CH2 domain near the hinge, and it is thought that binding of the V regions to an antigen helps displace the light chain constant region from sterically blocking the hinge. In this way, antibodies bound to antigen are preferentially bound by Fc receptors.

A fourth receptor, alternatively termed the 'protection receptor' (FcRp) or the 'neonatal receptor' (FcRn), is responsible for recycling antibodies from the endosome after the endocytosis of antibody-antigen complexes and their disaggregation in the endosome. The binding site for FcRp is found at the junction between the CH2 and CH3 domains in the three-dimensional antibody structure. The serum half-life of IgG antibodies depends on a productive interaction with functional FcRp. Other antibody types, such as IgM, IgD, IgE, and IgA do not bind to FcRp.

Another binding partner of certain antibodies is C1q, which mediates complement fixation.

Interaction with Fc receptors and FcRp also affects the biological activity and metabolism of fusion proteins containing an Fc moiety.

For example, fusion proteins with poor binding to FcR have longer serum half-lives than corresponding fusion proteins with good binding to FcR. Fusion proteins with poor binding to FcRp have shorter serum half-lives than corresponding fusion proteins with good binding to FcRp.

For example, Ig fusion proteins containing the CH2 and CH3 domains of IgG2 have a longer serum half-life than fusion proteins containing an IgG1. Similarly, fusion proteins containing an Fc region derived from IgG3 have a shorter serum half-life than corresponding fusion proteins containing IgG1 or IgG2. Fusion proteins containing CH2 and CH3 domains derived from IgM, IgD, IgE, and IgA have even shorter serum half-lives than corresponding IgG-derived fusion proteins.

To illustrate the uses of the invention, it is convenient to group antibodies and Ig fusion proteins into two general classes: proteins in which immunological effector functions are desired and proteins in which the Ig moiety serves as an immunologically inert carrier and lacks effector functions. In the former category of proteins it is convenient to construct proteins with hybrid isotypes in which a particular constellation of effector functions is created. In the latter category it is convenient to construct proteins with hybrid isotypes involving regions of certain isotypes with minimal effector functions and regions from other isotypes that enhance the assembly of the protein as described below.

Assembly of Antibodies and Ig Fusion Proteins

The invention discloses the discovery that the hinge of an antibody or an Ig fusion protein plays a key role in the proper assembly and lack of aggregation of a fusion protein, such as an Ig fusion protein secreted from a mammalian cell. For example, without wishing to be bound by theory, it is thought that antibody and Ig fusion protein assembly involves a step in which two heavy chains first non-covalently associate by a hydrophobic patch in the CH3 domain. After this association, the hinge regions are aligned and interchain disulfide bonds are formed. The hinge region is about 50 Angstroms from the hydrophobic patch in the CH3 domain.

In designing an antibody or Ig fusion protein construct, it is useful to vary the hinge region. For example, it is useful to replace the DNA encoding a hinge region in a given expression construct with DNA encoding a different hinge region, such as the hinge region from IgG1, IgG2, IgG3, IgG4, IgM, IgA, IgD, IgE, or IgY.

According to a theory of the invention, for example, antibodies and Ig fusion proteins containing hinge regions with a greater number of cysteines do not assemble as efficiently as corresponding proteins with fewer cysteines. Without wishing to be bound by theory, hinge regions with larger number of cysteines exhibit a greater chance for misalignment of the cysteines and incorrect disulfide bond formation. As a result, antibodies and Ig fusion proteins with hinge regions containing a larger number of cysteines are found to be more highly aggregated and exist in multiple electrophoretic species as compared to corresponding antibodies and Ig fusion proteins with hinge regions containing a smaller number of cysteines. Illustrations of this phenomenon are given in the Examples.

For example, antibodies and Ig fusion proteins containing a hinge region containing four cysteines are less efficiently assembled than antibodies and Ig fusion proteins containing three or two cysteines. For example, proteins containing an IgG2-derived hinge region are less efficiently assembled than corresponding proteins containing an IgG1-derived hinge region. In a distinct example, proteins containing an IgG3-derived hinge region are poorly assembled; the IgG3 hinge region contains 11 cysteines.

The utility of the invention is particularly illustrated in situations in which minimal binding to an Fc receptor I is desired. For example, in the context of fusion proteins, it is convenient to use the CH2 and CH3 regions from IgG2 because binding to FcR is profoundly reduced, so that ADCC is reduced and serum half-life is enhanced. However, use of the IgG2 hinge region causes the resultant antibody or Ig fusion to be poorly assembled. It is particularly convenient to use an IgG2 CH2 and CH3 region in combination with an IgG1 hinge, as illustrated in various Examples below.

A parallel finding, illustrated in several Examples, is that the choice of a particular hinge or other domain may affect the production levels of an antibody or Ig fusion. This finding is of great economic importance, since protein drugs such as intact antibodies often need to be dosed in large amounts, such as several hundred milligrams per patient per dose. It is generally found that the choice of a hinge with a minimal number of cysteines, such as three or two, improves the yield of an antibody or Ig fusion protein from a eukaryotic expression system. Lowering the number of cysteines may be accomplished by mutation or by substituting the hinge of one isotype for another, or both.

Enhancement of Protease Resistance

The hinge region is particularly sensitive to proteases. In classical experiments, antibodies were divided into Fab regions and Fc regions by protease cleavage in the hinge region.

It is convenient to construct antibodies and Ig fusion proteins with a hinge region from IgA and other components from other antibody isotypes. For example, if an antibody or Ig fusion protein is to be delivered orally or across another mucosal surface such as the nasal, lung, vaginal, or rectal mucosa, it is useful to have a particularly protease-resistant protein to protect the antibody or Ig fusion protein from proteases that are present. For example, it is useful to construct an antibody or Ig fusion protein that contains an IgA hinge and the CH2 and CH3 domains from an IgG, so that this hybrid isotype protein will have the features of protease resistance and an extended serum half-life once the protein enters the circulation. The hinge of IgA1 is a preferred hinge, because the glycosylation sites in the IgA1 hinge confer resistance to a broad spectrum of proteases. In contrast, the hinge of IgA2 is shorter and is resistant to bacterial proteases that specifically cleave the IgA1 hinge.

Other isotype heavy chains also contain glycosylation sites that contribute to protease resistance. For example, IgA, IgD, IgE, and IgM contain glycosylation sites in the constant domains that contribute to protease-resistance. For example, the IgE CH1 domain contains three N-linked glycosylation sites. It is useful to combine the IgE CH1 domain with, for example, a hinge region from IgA and with CH2 and CH3 domains from an IgG.

It is also useful to incorporate glycosylation sites from one isotype into the CH2 or CH3 region of another isotype. In such cases, it is generally not sufficient to construct antibodies or Ig fusion proteins in which entire domains, as defined by regions encoded by single exons, and so it is useful to construct hybrid domains. For example, it is useful to combine the features of FcRp binding characteristic of IgG isotypes and the protease-resistance features of other isotypes. To achieve such a combination of features, it is necessary to construct individual domains with amino acid sequences from two different isotypes. The resulting hybrid domains are then used to construct Ig fusions to non-Ig moieties.

For example, it is convenient to substitute a stretch of amino acids from the IgE CH2 domain that include the sequence VNLTW (SEQ ID NO: 3) for the corresponding amino acids in an IgG CH2 domain. For example, in IgG1 these amino acids are VKFNW (SEQ ID NO: 4) and in IgG3 these amino acids are VQFKW (SEQ ID NO: 5). According to the invention, the corresponding amino acids in other CH2 domains can be determined by computer-based or structural alignment of the CH2 domains of other isotypes, or from the published literature (Paul, W E *Fundamental Immunology* Fourth Edition, chapter 3, p. 46–47).

Similarly, it is also useful to incorporate other glycosylation sites into IgG. For example, sequence segments that include the NTSGF (SEQ ID NO: 6) or LNASR (SEQ ID NO: 7) sequences from IgD are used to replace the corresponding sequences of an IgG-derived Fc region in an antibody or Ig fusion protein. According to the invention, other useful glycosylation sites within antibody constant regions are disclosed in Paul (*Fundamental Immunology* Fourth Edition, chapter 3) and references therein.

In some embodiments of the invention, the incorporation of a non-IgG glycosylation site reduces the interaction with FcRp. In such cases, there is a tradeoff between the improvement in protease resistance and the decrease in serum half-life, and the usefulness of such a hybrid isotype protein must be evaluated in the context of a particular application.

According to the invention, the protease resistance of a particular hybrid isotype antibody or Ig fusion protein is assayed according to standard procedures. Proteases can be purchased from commercial suppliers and are incubated in the presence of a particular hybrid isotype antibody or Ig fusion protein in accordance with the manufacturer's specifications. Proteolysis is measured, for example, by SDS gel electrophoresis and quantitation of starting material and cleavage products.

According to the invention, the ability of a hybrid isotype antibody or Ig fusion protein to interact with FcRp is also measured according to standard procedures. For example, the pharmacokinetic properties of an antibody or Ig fusion protein are measured in a mammal such as a mouse, rat, rabbit, dog, non-human primate, or human. The pharmacokinetic properties of an antibody or Ig fusion protein are a practical indication of FcRp binding, and in general, the purpose of incorporating the feature of FcRp binding into an antibody or Ig fusion protein is to improve the pharmacokinetic properties of an antibody. It is also convenient to examine the three-dimensional structure of the FcRp-Fc complex to determine whether a particular hybrid isotype antibody or Ig fusion protein is likely to interact with FcRp (Martin, W. L., et al.: Crystal Structure at 2.8A of an FcRn/Heterodimeric Fc Complex: Mechanism of pH-Dependent Binding. *Mol. Cell* 7pp. 867 [2001].

According to this aspect of the invention, it is particularly useful to construct proteins of the form Fc-X, wherein the Fc region contains a hinge region from IgA1, a CH2 and CH3 region containing those elements of IgG2 that mediate binding to FcRp, and those elements of CH2 that have reduced effector functions compared to other IgGs.

Increasing the Valency of an Antibody or Ig Fusion Protein

According to the invention, it is sometimes useful to construct a hybrid isotype antibody or Ig fusion protein that has a high valency, but that also has effector functions or other features characteristic of lower-valency antibodies. IgA and IgM have a high valency due to oligomerization via interchain disulfide bonds in the CH3 region. IgA and IgM also have disulfide bonds from a cysteine near the C-terminus of CH4 to the J chain. IgA is dimeric and IgM is pentameric or hexameric, such that IgA has 4 antigen-binding sites and IgM has 10 or 12 antigen-binding sites.

However, IgM and IgA do not mediate ADCC. To construct a polyvalent antibody or Ig fusion that mediates ADCC, it is useful to construct a protein that has the CH2 domain of an IgG and the CH3 and CH4 domains of IgM or IgA. In general, it is preferable to use IgM CH3 and CH4 domains, since the resulting hybrid isotype protein has a higher valency than the corresponding IgA-containing hybrid isotype protein.

The following application illustrates the utility of hybrid isotype fusion proteins with increased valency. Many tumor cells overexpress the EGF-receptor on their cell surfaces. The EGF-receptor is also expressed on the surface of many normal cells, so the difference in EGF-receptor expression between normal and tumor cells is only quantitative. According to one embodiment of the invention, a useful IgG-IgM hybrid isotype protein comprises a V region that interacts weakly with the human EGF-receptor. The affinity of the V region is chosen so that the fusion protein does not efficiently interact with EGF-R on normal cells, but interacts with the overexpressed EGF-receptor on tumor cells as a result of an avidity effect. The use of a CH2 domain of an IgG, for example the CH2 domain of IgG1, mediates ADCC against the tumor cells.

To enhance the specific killing of tumor cells, it is also useful to fuse the anti-EGF-R IgG-IgM hybrid isotype protein to a protein with anti-tumor activity, such as a cytokine. For example, IL-2 may be used. Alternatively, it is useful to conjugate a radioactive atom to the hybrid isotype protein, such that concentration of the hybrid isotype protein in the region of the tumor causes preferential irradiation of the tumor. For example, Yttrium-90 may be conjugated to the IgG-IgM hybrid isotype protein. The combination of ADCC and IL-2 action or ADCC and irradiation is particularly useful in killing tumor cells.

In an IgG-IgM fusion protein, such as the anti-tumor protein described above, it is also generally useful to use a hinge region from IgG, preferably IgG1. The hinge region from IgG3 is, for many applications, the least preferred IgG hinge region, because this hinge region tends to cause variable assembly; moreover, the IgG3 hinge is easily proteolyzed (Baici A, et al., Scand J Immunol. [1980] 12:41–50).

The preceding example illustrates a general principle of this aspect of the invention: that an antigen that is more highly expressed on a target cell type than on normal cells may be more effectively targeted by an antibody or Ig fusion protein with a high valency but a relatively low monovalent affinity.

For example, in autoimmune diseases, certain immune cells such as T cells express a higher level of cell surface proteins such as cytokine receptors. It is useful to attack such immune cells with a high valency IgG1, IgG2, or IgG4-IgM antibody or Ig fusion protein directed against the up-regulated surface protein. In this way, targeting of cells in which the cell surface protein is present but not up-regulated is minimized. For example, during an attack of an autoimmune disease, it is useful to treat a patient with an IgG-IgM fusion protein in which the V regions are directed against, for example the IL-2 receptor, the IL-12 receptor, or any other up-regulated receptor. The hinge region and the CH2 domain are preferably derived from IgG1, IgG2, or IgG4, and the CH3 and CH4 regions are preferably derived from IgM. The V regions preferably bind weakly to the IL-2 or IL-12 receptor for the treatment of autoimmune disease. This treatment has the effect of killing a subset of T cells but not the entire T cell repertoire.

Construction of Expression Plasmids that Express Antibodies and Ig Fusion Proteins with Hybrid Isotypes.

The invention also provides nucleic acids that encode the antibodies and fusion proteins of the invention. The invention is best practiced when the encoding nucleic acids also encode a secretion cassette that, when transcribed and translated, gives rise to a signal peptide. The signal peptide is generally cleaved from the mature product. The secreted fusion protein can be collected from the culture media without the need for lysis of the host cell, and can be assayed for activity or purified using common reagents as desired. In some cases, the presence of certain fusion partners, such as the cytokine CNTF, allows for secretion of an Ig fusion protein without a secretion cassette.

One of ordinary skill in the art can perform such recombinant DNA constructions using DNA with introns, because the naturally occurring introns separate the DNA encoding the hinge from the DNA encoding the CH1 and CH2 domains. Restriction sites in the introns can be used. Alternatively, because the hinge regions are generally only about 15 to 70 amino acids long, it is possible to construct synthetic DNAs encoding an entire hinge region, for example with oligonucleotide synthesis, PCR, or a combination thereof. The synthetic hinge-encoding region can then be placed into an expression plasmid encoding an Ig fusion protein using standard recombinant DNA techniques.

The invention is illustrated further by the following non-limiting examples.

EXAMPLES

Example 1

Construction of a Plasmid Expressing an Fc-X Fusion Protein with a Hinge Region and CH2 Region from Different Antibody Isotypes The construction of a plasmid that expresses HuFcγ1-Leptin has been described in the PCT publication WO00/040615A2.

A plasmid that expresses a fusion of an IgG2-derived Fc and a C-terminal fusion partner was constructed as follows.

First, the genomic sequence of human γ2 Fc was obtained. The genomic DNA encoding human Fcγ2 was obtained by PCR on cellular DNA isolated from human PBMCs. The forward primer had the sequence 5' CC TTA AGC GAG CGC AAA TGT TGT GTC GAG (SEQ ID NO: 8), where an AflII restriction site C TTA AG was introduced just upstream of the γ2 hinge coding region GAG CGC AAA TGT TGT GTC GAG (SEQ ID NO:9). The reverse primer had the sequence 5' CCTCGAG TCA TTT ACC CGG GGA CAG GGA G (SEQ ID NO: 10), where an XhoI restriction site CTCGAG was introduced immediately after the translation stop codon (anticodon TCA). In addition, the reverse primer also introduced a SmaI CC CGGGby silent mutation (A to G substitution underlined). The 910 bp PCR fragment was cloned into the TOPO TA Cloning Vector (Invitrogen, Carlsbad, Calif.) for sequence verification.

Second, the human γ2 Fc was placed into an expression vector. The natural SmaI restriction site in the DNA sequence CTG CCC CCA TCC CGG GAG GAG ATG ACC AAG (SEQ ID NO: 11) encoding the upper CH3 region was deleted by a silent mutation introduced by an overlapping PCR technique (Daugherty, B. L. et al., Nucleic Acids Res. 19:2471–6, 1991). The forward primer had the sequence 5' CTG CCC CCA TCACGG GAG GAG ATG ACC AAG (SEQ ID NO: 12), where the C to A substitution is underlined; and the reverse primer had the sequence 5' GGT CAT CTC CTC CCG TGATGG GGG CAG GGT GTA C (SEQ ID NO: 13), where the G to T substitution is underlined. After sequence verification, the resultant AflII-XhoI restriction fragment encoding the Fc of γ2 contained a unique SmaI site upstream of the translation stop codon, and a XhoI site downstream of the stop codon. The AflII-SmaI fragment encoding Fcγ2 was then used to replace the corresponding restriction fragment encoding Fcγ1 in pdCs-huFcγ1-Leptin (PCT publication WO00/040615A2) to give pdCs-huFcγ2-Leptin.

Third, the DNA encoding the hinge of the Fc γ2 was replaced by the altered hinge from γ1. The γ2 hinge region contains four cysteine disulphide bonds. Shown below is the AflII-StuI fragment containing the γ2 hinge exon. The AflII site (C TTA AG) is preceded by DNA sequence encoding a signal peptide. Glutamic acid (E) is the first amino acid residue of the γ2 hinge. The letters in small case represent the intron sequence following the γ2 hinge exon. The StuI restriction site (aggcct) is C-methylated in most *E. coli* strains by the DCM methylase because of the C-methylation in the sequence ccagg and the reverse strand cctgg; when methylated, this site cannot be cut by StuI.

```
        E   R   K   C   C   V   E   C   P   P   C   P    (SEQ ID NO:14)
C  TTA AGC GAG CGC AAA TGT TGT GTC GAG TGC CCA CCG TGC CCA G (SEQ ID NO:15)

gtaagccagcccaggcct
```

The AflII-StuI fragment containing the γ2 hinge exon in pdCs-huFcγ2-Leptin was replaced by the corresponding AflII-StuI fragment containing the γ1 hinge exon from pdCs-huFc γ1-Leptin, which is shown below:

```
        E   P   K   S   S   D   K   T   H   T   C   P   P   C   P    (SEQ ID NO:16)
C  TTA AGC GAG CCC AAA TCT TCT GAG AAA ACT CAC ACA TGC CCA CCG TGC CCA G (SEQ ID NO:17)

Gtaagccagcccaggcct
```

The γ1 hinge sequence in pdCs-huFc γ1 contains a Cys to Ser mutation (underlined) which eliminates the Cys residue that forms a disulphide bond with the light chain in IgG1 (Lo et al., (1998) Protein Engineering 11:495–500). Since the StuI sites in both the γ1 and γ2 exons are C-methylated and the StuI restriction endonuclease is methylation sensitive, both plasmids were isolated from a DCM negative strain of bacteria before digestion with the StuI enzyme. The resultant pdCs-huFcγ2-Leptin with the hinge region from pdCs-huFc γ1 was designated pdCs-huFcγ2h-Leptin (γ2h: γ2 with altered hinge).

Example 2

Characterization of the Oligomerization State of huFc γ2-leptin and huFcγ2h-leptin Immunofusion Protein expression from NS/0 cells using expression vector pdCs-huFc-huLeptin with the γ1, γ2, and γ2h isotypes was evaluated. The physical state of different forms of huFc-huLeptin in which the huFc moiety derived from γ1, γ2, and γ2h isotypes were evaluated.

DNA constructs generated as described above and as in Lo et al. were transfected into NS/0 cells and stable expressing cell lines were generated according to standard procedures.

In this and the following Examples, stable transfectants were generated as follows. Plasmid DNAs were introduced into the mouse myeloma NS/0 cells by electroporation. NS/0 cells were grown in Dulbecco's modified Eagle's medium supplemented with 10% fetal bovine serum, 2 mM glutamine and penicillin/streptomycin. About 5×10$^6$ cells were washed once with PBS and resuspended in 0.5 ml PBS. Ten μg of linearized plasmid DNA were then incubated with the cells in a Gene Pulser Cuvette (0.4 cm electrode gap, BioRad) on ice for 10 min. Electroporation was performed using a Gene Pulser (BioRad, Hercules, Calif.) with settings at 0.25 V and 500 μF. Cells were allowed to recover for 10 min. on ice, after which they were resuspended in growth medium and then plated onto two 96 well plates. Stably transfected clones were selected by growth in the presence of 100 nM methotrexate (MTX), which was introduced two days post-transfection. The cells were fed every 3 days for two to three more times, and MTX-resistant clones appeared in 2 to 3 weeks. Supernatants from clones were assayed by anti-Fc ELISA to identify high producers. High producing clones were isolated and propagated in growth medium containing 100 nM MTX.

Concentration of HuFc-huLeptins in the supernatant was determined by an anti-huFc ELISA, using anti-huFc antibody (horseradish peroxidase-conjugated goat anti-huIgG, Fcγ1 or Fcγ2, from Jackson ImmunoResearch). Relatively low levels of expression were detected in the supernatants of the γ2 constructs whereas the γ1 and γ2h constructs gave high levels of expression in both transient and stable transfections. In transient transfections with equivalent expression vectors encoding huFcγ2-huLeptin and huFcγ2h-huLeptin, the huFcγ2h-huLeptin was produced at 8-fold higher levels.

For purification, the fusion proteins in tissue culture supernatants were bound to Protein A Sepharose followed by elution in a sodium phosphate buffer (100 mM NaH$_2$PO$_4$, pH 3, and 150 mM NaCl). The eluate was then neutralized with 0.1 volume of 2 M Tris-hydrochloride, pH 8 and evaluated by SDS-polyacrylamide gel electrophoresis (SDS-PAGE) and HPLC-size exclusion chromatography (SEC).

Fusion proteins were examined by SDS-PAGE under non-reducing conditions. The protein bands, visualized by Coomassie staining, showed HuFcγ1-huLeptin to have an apparent MW of 96 kD, indicating a bivalent monomer. Analysis by SDS-PAGE showed that much of the huFcγ2-huLeptin fusion protein was in a higher molecular weight form, migrating as a ladder of bands with apparent molecular weights much higher than Fc-Leptin. In contrast, huFcγ2h-huLeptin was primarily a single species, migrating at 96 kD.

Size exclusion chromatography (SEC) analysis of huFcγ2h construct correlated with SDS-PAGE results and showed both huFcγ2h-leptin and huFcγ1-leptin to be about 83% monomeric, while the comparable huFcγ2-huLeptin fusion protein was about 55% monomeric.

Studies with fixed J774 cells, which are rich in the FcγR class of receptors, showed that only the huFcγ1-huLeptin fusion protein exhibits Fc binding. In addition, BAF-3 cells transfected to express the leptin receptor so that their proliferation could be stimulated by leptin (Gainsford, T., et al. PNAS [1996] 93:14564–14568) were used. Studies with BAF3/leptin receptor cells showed that huFcγ1-huLeptin, huFcγ2-huLeptin and huFcγ2h-huLeptin were equivalent in leptin bioactivity.

Stable clones of mammalian cells expressing huFcγ2-huLeptin and huFcγ2h-huLeptin were also identified. Cell transfections were carried out under essentially identical conditions and an identical number of stably transfected cells were cloned and tested for production of huFcγ2-huLeptin and huFcγ2h-huLeptin. The best-expressing clone for huFcγ2h-huLeptin made about 5-fold more huFc-huLeptin than the best-expressing clone for huFcγ2-huLeptin.

Example 3

Construction of a Plasmid Expressing an X-Fc Fusion Protein with a Hinge Region and CH2 Region from Different Antibody Isotypes The synthetic DNA sequence (SEQ ID NO: 18) encoding glucagon-like peptide 1 (GLP-1) amino acid residues 7 to 37 (SEQ ID NO: 19) is disclosed below.

```
        H   A   E   G   T   F   T   S   D   V   S   S   Y   L   E   G
C TTA AGC CAT GCT GAA GGG ACC TTT ACT AGT GAT GTA AGT TCT TAT TTG GAA GGC

Q   A   A   K   E   F   I   A   W   L   V   K   G   R   G
  CAA GCT GCC AAG GAA TTC ATT GCT TGG CTG GTG AAA GGC CGA GGA GGA TCC TTA
```

The DNA encoding the GLP-1 peptide was preceded by C TTA AGC, where the AflII restriction site was used to join this DNA fragment to the DNA fragment encoding the signal sequence (Lo et al. Protein Engineering). At the 3' end, the DNA encoding GLP-1 was followed by a BamHI restriction site (GGA TCC, which encodes the amino acid residues G and S), and an AflII restriction site, which was used to ligate to the AflII-XhoI restriction fragment encoding Fc γ2 (or Fc γ2h) with a translation stop codon (see Example 1).

Example 4

Characterization of the Oligomerization State of GLP1-huFc γ2 and GLP1-huFc γ2h Immunofusions The resultant vectors from Example 3, pdCs GLP-1 huFcγ1, pdCs GLP-1 huFcγ2, and pdCs GLP-1 huFcγ2h, were used to transiently and stably transfect mammalian cells for the expression of GLP-1 (7-37) huFc γ1, GLP-1 (7-37) huFc γ2 and GLP-1 (7-37) huFc γ2h.

Assessment of aggregation state and total protein expression for each GLP-1 huFc fusion protein was performed by SDS-PAGE and HPLC-SEC after purification by Protein A Sepharose, using the general methods described in Example 2. The protein bands were visualized by Coomassie staining. GLP-1 huFcγ2 and GLP-1huFcγ2h had an apparent MW of approximately 60 kD by SDS-PAGE. Concentration of GLP-1 huFc variants in the supernatant was determined by anti-huFc ELISA. In transient transfections with equivalent expression vectors encoding GLP1-huFcγ2 and GLP1-huFcγ2h, the GLP1-huFcγ2h was produced at about 1.5-fold higher levels.

Analysis of total cell lysates by SDS-PAGE showed that about half of the GLP1-huFcγ2 fusion protein had incorrect disulfide bonds, as illustrated by the presence of several high molecular weight forms migrating with an apparent weight of 100 to 200 kD. In contrast, essentially all of the detectable GLP1-huFcγ2h fusion protein migrated with an apparent molecular weight of about 60 kD. When the samples were reduced before SDS-PAGE, the GLP1-huFcγ2 and GLP1-huFcγ2h proteins ran with an essentially identical apparent molecular weight of about 34 kD.

Comparative analysis by HPLC-SEC of the γ1, γ2 and γ2h fusion proteins demonstrated that the modified γ2h fusion protein was significantly more monomeric than the other fusion proteins. The modified GLP1-huFcγ2h fusion protein, as illustrated by a single peak, was 84% bivalent monomer, while both the GLP1-hufcγ1 and GLP1-huFcγ2 fusions proteins had multiple peaks corresponding to approximately 42 and 33% bivalent monomer, respectively.

Thus, the GLP-1-Fc fusion protein bearing the hinge of IgG1 and the CH2 and CH3 domains of IgG2 showed surprisingly better assembly properties than GLP-1-Fc fusion proteins in which the entire Fc region derived from either IgG1 or IgG2.

Example 5

Construction of an Intact Antibody Specific for Diseased Cells that Contains IgG2 CH1, CH2, and CH3 Domains and an IgG1 Hinge The genomic DNA encoding the immunoglobulin γ 2 constant regions (CH1, hinge, CH2 and CH3) was obtained by PCR using cellular DNA isolated from human PBMCs. The forward primer had the sequence 5' CA AGC-TTCTGGGGCGAGC (SEQ ID NO: 20), where a HindIII restriction site A AGCTT was introduced to the intron sequence about 220 bp upstream of the CH1 exon. The reverse primer has the sequence 5' CCTCGAG TCA TTT ACC CGG GGA CAG GGA G (SEQ ID NO: 21), where an XhoI restriction site CTCGAG was introduced immediately after the translation stop codon (anticodon TCA), and a SmaI CC CGGG was created by silent mutation, as already described in Example 1. The natural SmaI restriction site in the DNA sequence encoding the upper CH3 region was also deleted by a silent mutation introduced by overlapping PCR, as described in Example 1. One skilled in the art would also recognize that by taking advantage of restriction fragments encoding the Fcγ2 obtained in Example 1, a ~1810 base pair (bp) HindIII-XhoI restriction fragment encoding the CH1, hinge, CH2 and CH3 regions and containing a unique SmaI restriction site could be readily constructed. After sequence verification, the HindIII-XhoI fragment encoding γ2 constant regions was used to replace the HindIII-XhoI fragment encoding γ1 constant regions-IL2 in pdHL7-huKSγ1-IL2 to give pdHL7-huKSγ2 antibody.

The expression vector for huKSγ2h antibody was constructed as follows. The plasmid pdCs-huFcγ2h-Leptin was used as the PCR template for creating a ~130 bp PstI-PvuII restriction fragment encoding the cysteine-to-serine modified γ1 hinge region only. The forward primer had the sequence 5' CTGCAGAGCCCAAATCTTC (SEQ ID NO: 22), which restored the native PstI (CTGCAG) restriction site at the beginning of the γ1 hinge exon (with the C to S mutation described above). The reverse primer had the sequence 5' CAGCTGGGGCCTGTCCCTG (SEQ ID NO: 23), which corresponded to the PvuII site (CAGCTG) in the intron between the hinge and the CH2 exons. After sequence verification, this ~130 bp PstI-PvuII restriction fragment was used to replace the corresponding fragment in pdHL7-huKSγ2 antibody to give the pdHL7-huKSγ2h antibody.

Example 6

Characterization of the Non-reduced State of a γ2-antibody and a Corresponding γ2h Antibody Directed Against Diseased Cells For transient transfection, the vectors, pdHL7 of KS antibody with IgGγ1, γ2, and γ2h isotypes were introduced into mammalian cells by lipofection using Lipofectamine Plus (Life Technologies, Gaithersburg, Md.) according to supplier's protocol. Stable transfectants were generated as described in Example 2.

KS antibodies in the conditioned media (10% serum) were captured on Protein A Sepharose (Repligen, Cambridge, Mass.) and then eluted by boiling in the protein sample buffer with or without 2-mercaptoethanol prior to characterization by SDS-PAGE. Visualization by Coomassie staining showed non-reduced KS γ2 antibody to migrate as several species with molecular weights of approximately 150 kD. In contrast, the KSγ2h antibody migrated as a major band with an apparent molecular weight of 150 kD. When the KS γ2 antibody and KS γ2h antibody were reduced with mercaptoethanol before SDS-PAGE, an identical pattern of bands corresponding to the heavy and light chains was observed for both the KSγ2 antibody and KSγ2h antibody.

Without wishing to be bound by theory, these observations suggest that the distinctly migrating species seen with KSγ2 were due to variations in disulfide bonding patterns.

Stable clones of mammalian cells expressing KSγ2 antibody and KSγ2h antibody were also identified. Cell transfections were carried out under essentially identical conditions and similar numbers of stably transfected cells were cloned and tested for production of huFc KSγ2 antibody and KSγ2h antibody. The four best-expressing clones for KSγ2h antibody made about 114, 98, 85, and 49 micrograms of antibody per ml of tissue culture supernatant, while under the same conditions the four best-expressing clones for huFc KSγ2 antibody made about 36, 34, 15, and 13 micrograms of antibody per ml of tissue culture supernatant.

Example 7

Construction of a Fusion Protein Including a Complete Antibody that Contains IgG2 CH1, CH2, and CH3 Domains and an IgG1 Hinge In this Example, the usefulness of an antibody fusion protein in which the antibody moiety had a hybrid isotype was examined.

The expression vector for huKSγ2-IL2, pdHL7-huKSγ2-IL2, was constructed by replacing the SmaI-XhoI restriction fragment in pdHL7-huKSγ2 antibody, which contains the sequence GGGTAAATGA (SEQ ID NO: 24) followed by the XhoI sticky end, by the SmaI-XhoI restriction fragment isolated from pdHL7-huKS-IL2. This latter fragment contains the sequence GGGTAAA followed immediately by the DNA sequence encoding the mature IL2 including the translation stop codon. The resultant expression vector, pdHL7-huKSγ2-IL2, was used to transfect cells for protein expression.

Similarly, the expression vector for huKSγ2h-IL2, pdHL7-huKSγ2h-IL2, was constructed by replacing the SmaI-XhoI restriction fragment in pdHL7-huKSγ2h antibody, which contains the sequence GGGTAAATGA (SEQ ID NO: 24) followed by the XhoI sticky end, by the SmaI-XhoI restriction fragment isolated from pdHL7-huKS-IL2 as described in the preceding paragraph. The resultant expression vector, pdHL7-huKSγ2h-IL2, was used to transfect cells for protein expression.

Example 8

Characterization of the Non-reduced State of a γ2-antibody Fusion Protein and a Corresponding γ2h Antibody Fusion Protein For transient transfection, the plasmids encoding KS γ2-IL2 and KS γ2h-IL2 were introduced into mammalian cells by lipofection using Lipofectamine Plus (Life Technologies, Gaithersburg, Md.) according to supplier's protocol.

In order to obtain stably transfected clones, plasmid DNAs were introduced into mouse myeloma NS/0 cells by electroporation as described in Example 2.

KS-IL2 fusion proteins with the γ2 and γ2h isotypes were characterized by SDS-PAGE as described in Example 6. Antibody fusion proteins in the conditioned media (10% serum) were captured on Protein A Sepharose (Repligen, Cambridge, Mass.) and then eluted by boiling in the protein sample buffer with or without 2-mercaptoethanol prior to characterization by SDS-PAGE. Visualization by Coomassie staining showed non-reduced KSγ2-IL2 to migrate as several species with molecular weights of approximately 180 kD. In contrast, the KSγ2h-IL2 migrated as a major band with an apparent molecular weight of about 180 kD. When the KSγ2-IL2 and KSγ2h-IL2 were reduced with mercaptoethanol before SDS-PAGE, an identical pattern of bands corresponding to the heavy chain-IL2 and light chains was observed for both the KSγ2-IL2 and KSγ2h-IL2.

Without wishing to be bound by theory, these observations suggest that the distinctly migrating species seen with KSγ2-IL2 were due to variations in disulfide bonding patterns.

The modified γ2h immunocytokines are tested in animals and have extended half-lives with better efficacy in animal tumor models relative to original IgGγ1-based immunocytokines.

Stable clones of mammalian cells expressing KSγ2-IL2 and KSγ2h-IL2 were also identified. Cell transfections were carried out under essentially identical conditions and similar numbers of stably transfected cells were cloned and tested for production of KSγ2-IL2 and KSγ2h-IL2. The four best-expressing clones for KSγ2h-IL2 made about 52, 37, 31, and 30 micrograms of fusion protein per ml of tissue culture supernatant, while under the same conditions the four best-expressing clones for KSγ2-IL2 made about 31, 27, 27, and 17 micrograms of fusion protein per ml of tissue culture supernatant.

Example 9

Construction of Plasmids Expressing Antibody Fusion proteins with a Hybrid Isotype and a Secondary Mutation Affecting Fusion Protein Activity HuKSγ2-Ala-IL2 vs huKSγ2h-Ala-IL2

The expression vectors pdHL7-huKSγ2-Ala-IL2 and pdHL7-huKSγ2h-Ala-IL2 (described above) were constructed by replacing the SmaI-XhoI restriction fragment in pdHL7-huKSγ2 antibody and pdHL7-huKSγ2h antibody, respectively, which contains the sequence GGGTAAATGA (SEQ ID NO: 24) followed by the XhoI sticky end, by the corresponding SmaI-XhoI restriction fragment isolated from pdHL7-huKSγ1-Ala-IL2. This latter fragment contains the sequence GGGTGCA followed immediately by the DNA sequence encoding the mature IL2 including the translation stop codon. The GCA encodes the lysine to alanine substitution at the junction of the fusion protein. The resultant vectors were used to transfect cells for the production of huKSγ2-Ala-IL2 and huKSγ2h-Ala-IL2.

Example 10

Characterization of the Non-reduced State of a γ2-antibody Fusion Protein and a Corresponding γ2h Antibody Fusion Protein Carrying a Secondary Mutation Affecting Fusion Protein Function For transient transfection, the plasmids encoding KSγ2-Ala-IL2 and KSγ2h-Ala-IL2 were introduced into mammalian cells by lipofection using Lipofectamine Plus (Life Technologies, Gaithersburg, Md.) according to supplier's protocol.

Stable clones of mammalian cells expressing KSγ2-Ala-IL2 and KSγ2h-Ala-IL2 were also identified as in Example 2. Cell transfections were carried out under essentially identical conditions and similar numbers of stably transfected cells were cloned and tested for production of KSγ2-Ala-IL2 and KSγ2h-Ala-IL2. The three best-expressing clones for KSγ2h-Ala-IL2 made about 39, 38, and 29 micrograms of fusion protein per ml of tissue culture supernatant, while under the same conditions the three best-expressing clones for KSγ2-Ala-IL2 made about 22, 17, and 6 micrograms of fusion protein per ml of tissue culture supernatant. KS-Ala-IL2 fusion proteins with the γ2 and γ2h isotypes were characterized by SDS-PAGE as described in Example 6. KS-Ala-IL2 fusion proteins in the conditioned media (10% serum) were captured on Protein A Sepharose (Repligen, Cambridge, Mass.) and then eluted by boiling in the protein sample buffer with or without 2-mercaptoethanol prior to characterization by SDS-PAGE. Visualization by Coomassie staining showed non-reduced KSγ2-Ala-IL2 to migrate as several species. In contrast, the KSγ2h-Ala-IL2 migrated as one major species. When the KSγ2-Ala-IL2 and KSγ2h-Ala-IL2 are reduced with mercaptoethanol before SDS-PAGE, an identical pattern of bands corresponding to the heavy chain-IL2 and light chains was observed for both the KSγ2-Ala-IL2 and KSγ2h-Ala-IL2.

Without wishing to be bound by theory, these observations suggest that the distinctly migrating species seen with KSγ2-Ala-IL2 were due to variations in disulfide bonding patterns.

Example 11

Expression of an Antibody Fusion Protein with Constant Regions Derived from Different Isotypes In some cases, it is desirable to construct an Ig fusion protein in which different constant regions, in addition to the hinge region, are derived from different heavy chain isotypes. To examine the properties of this class of molecules, the following experiments were conducted.

The huKS(γ1:CH1-H)(γ2:CH2-CH3)-Ala-IL2 protein, which is an antibody-IL2 fusion protein with the IgG heavy chain comprising the KS VH, the CH1 and hinge regions from IgG1 and CH2-CH3 regions from IgG2 (with the lysine to alanine substitution at the fusion junction, as described above) followed by IL-2, was expressed as follows. The expression vector pdHL7-huKS(γ1:CH1-H)(γ2:CH2-CH3)-Ala-IL2 was constructed by replacing the HindIII-AflIII restriction fragment in pdHL7-KS γ2-Ala-IL2 with the corresponding HindIII-AflIII restriction fragment containing the CH1 and hinge regions from pdHL7-KS-IL2. This expression vector was transfected into cultured mammalian cells as described above to yield an antibody fusion protein with a hybrid isotype.

The HuKS(γ1:CH1-H)(γ2:CH2-CH3)(Ala)-IL2 hybrid and HuKSγ2(Ala)-IL2 antibody-cytokine fusion proteins were characterized by non-reducing SDS-PAGE as described in Example 6. The HuKS(γ1:CH1-H)(γ2:CH2-CH3)(Ala)-IL2 hybrid isotype fusion protein migrated as a major band with a molecular weight of about 180kD. In contrast, the HuKSγ2(Ala)-IL2 antibody-cytokine fusion protein migrated as multiple bands in the 180 kD size range.

When the HuKS(γ1:CH1-H)(γ2:CH2-CH3)(Ala)-IL2 hybrid and HuKS(γ2)(Ala)-IL2 antibody-cytokine fusion proteins were characterized by reducing SDS-PAGE, both proteins gave an identical pattern of bands, corresponding to the light chain and the heavy chain-IL2 fusion polypeptides.

Without wishing to be bound by theory, it appeared that the HuKS(γ2)(Ala)-IL2 antibody-cytokine fusion protein existed in at least two different isomeric configurations, in which the difference was due to a difference in disulfide bonding pattern.

Example 12

Expression of Hybrid Isotype Antibody Fusion Proteins with a Non-protein Antigen Specificity and a Multi-subunit Fusion Partner The 14.18 antibody binds to the glycolipid antigen GD2. Interleukin-12 is a heterodimeric cytokine that includes a p35 and p40 subunit, covalently attached by a disulfide bond.

As described above, use of a hybrid isotype, such as an IgG1/IgG2 hybrid, leads to enhanced assembly as compared to a natural isotype, such as IgG2. Enhanced assembly may be evidenced by increased expression levels.

In one case, 14.18(γ2)-Ala-IL12 and 14.18(γ2h)-Ala-IL12 expression plasmids were constructed and transiently transfected into cells in parallel under identical conditions as described above and in Gillies et al. (WO09929732). Human IL-12 was used. The level of protein in the tissue culture supernatant was about 40% higher from the cultures transfected with the 14.18(γ2h)-Ala-IL12 expression plasmid than from the cultures transfected with the 14.18(γ2)-Ala-IL12 expression plasmid.

The 14.18(γ2)-Ala-IL12 and 14.18(γ2h)-Ala-IL12 expression plasmids were also stably transfected into cells as described above, and the four highest-expressing clones from each transfection were studied further. For 14.18(γ2h)-Ala-IL12, the average of the four best-expressing clones was about 45% higher than for the four best-expressing clones derived from the 14.18(γ2)-Ala-IL12 expression plasmid.

In a second case, 14.18(γ2)-IL12 and 14.18(γ2h)-IL12 expression plasmids were constructed and transiently transfected into cells in parallel under identical conditions as described above. Mouse IL-12 was used. The level of protein in the tissue culture supernatant was about 40% higher from the cultures transfected with the 14.18(γ2h)-

IL12 expression plasmid than from the cultures transfected with the 14.18(γ2)-IL12 expression plasmid.

The 14.18(γ2)-IL12 and 14.18(γ2h)-IL12 expression plasmids using murine IL-12 were also stably transfected into cells as described above, and the four highest-expressing clones from each transfection were studied further. For 14.18(γ2h)-IL12, the average of the four best-expressing clones was about 35% higher than for the four best-expressing clones derived from the 14.18(γ2)-IL12 expression plasmid.

These results indicated that use of a hybrid isotype in a fusion protein led to enhanced expression, even when using a different antibody and different non-Ig moiety than in the previous examples. In this Example, the use of IL-12 as the non-Ig moiety is expected to significantly complicate the assembly of the Ig fusion protein, because IL-12 is a heterodimer. Nonetheless, the use of a hybrid isotype had a beneficial effect.

Example 13

Expression of Hybrid Isotype Antibody Fusion Proteins Using a Hinge Region from IgA To construct an Ig fusion protein with enhanced protease resistance, an IgA/IgG fusion protein is produced.

For example, an Fc-X fusion protein is constructed that contains the hinge region of human IgA1 and the CH2 and CH3 regions of IgG2.

An example of the construction of an expression vector to produces an Fc-X fusion protein comprising the hinge region from human IgA1 and the CH2 and CH3 regions of IgG2 is as follows. The plasmid pdCs-huFcγ2-Leptin from Example 1 is used as a vector.

The AflII-StuI fragment containing the γ2 hinge exon in pdCs-huFcγ2-Leptin is replaced by the corresponding AflII-StuI fragment (SEQ ID NO: 25) containing the IgA1 hinge exon, which is shown below:

```
(AflII)     P   S   T   P   P   T   P   S   P   S   T   P
CTTAAG  T  CCC TCA ACT CCA CCT ACC CCA TCT CCC TCA ACT CCA (SEQ ID NO:26)

P   T   P   S   P   S   C   C   H                 (StuI)
 CCT ACC CCA TCT CCC TCA TGC TGC CAC Ggtaagccagcccaggcct
```

Specifically, the following oligonucleotides are synthesized:

```
Top strand:
5'-
TTAAGTCCCTCAACTCCACCTACCCCATCTCCCTCAACTCCACCTACCCCATCTCCCTC     (SEQ ID NO:27)
ATGCTGCCACGGTAAGCCAGCCCAGG-3'

Bottom strand:
5'-
CCTGGGCTGGCTTACCGTGGCAGCATGAGGGAGATGGGGTAGGTGGAGTTGAGGGAGATGG    (SEQ ID NO:28)
GGTAGGTGGAGTTGAGGGAC-3'
```

These oligonucleotides are annealed, and used to replace the corresponding fragment in pdCs-huFcγ2-Leptin.

Since the StuI sites in the γ2 exon is C-methylated and the StuI restriction endonuclease is methylation sensitive, the plasmid is isolated from a DCM negative strain of bacteria before digestion with the StuI enzyme. The resultant pdCs-huFcγ2-Leptin with the hinge region from IgA1 is designated pdCs-huFcα1/γ2-Leptin.

The plasmid pdCs-huFcα1/γ2-Leptin is transfected into eukaryotic cells and an Fc-X protein of the form α1 (hinge)-γ2(CH2, CH3)-leptin is expressed as a secreted protein. For example, the cells and methods of Example 2 are used. The resulting α1-γ2-leptin protein is purified, characterized, and found to possess leptin activity and to be relatively insensitive to protease cleavage in the hinge region.

Example 14

Figure 4:
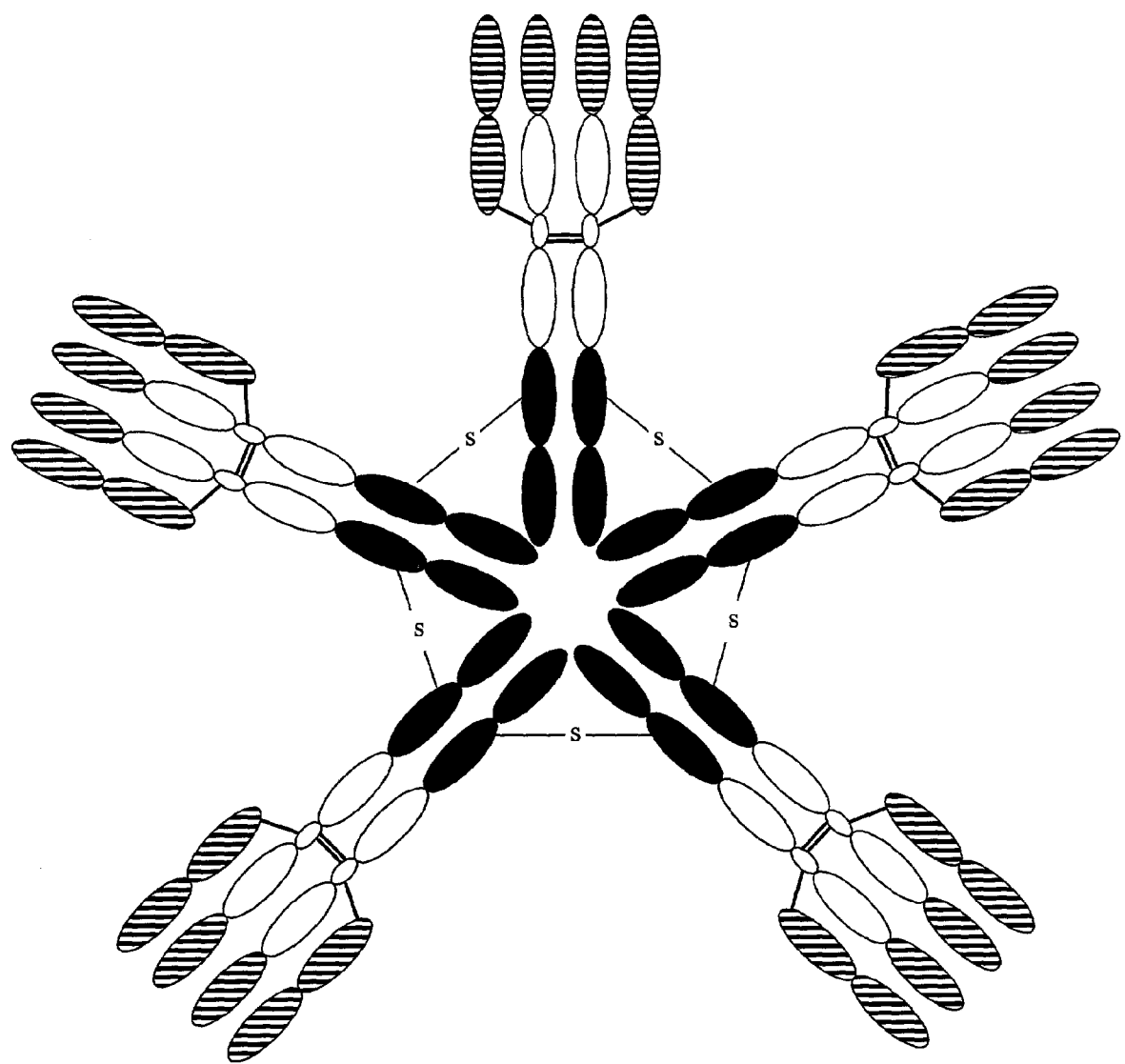
FIG. 4 is a schematic illustration of an Ig fusion protein that comprises variable regions, comprising multiple isotypes, and that have increased valency compared to IgG; black ovals represent the CH3 and CH4 domains from IgM; white ovals represent the CH1, hinge, and CH2 domains from an IgG; striped ovals represent variable domains and the light chain constant domain; thick lines represent disulfide bonds normally found in IgG1; thin lines labeled with an 's' represent disulfide bonds normally found in IgM.

Expression of Hybrid Isotype Antibody Fusion Proteins Using Components of IgG and a Polyvalent Immunoglobulin To construct antibody fusion proteins with the effector functions of an IgG, such as IgG1 or IgG3, and an increased valency, a hybrid isotype Ig fusion protein using the CH1, hinge, and CH2 regions of an IgG and the CH3 and CH4 regions of an IgA or IgM are constructed. FIG. 4 shows the structure of an IgG-IgM hybrid isotype fusion antibody. It is convenient to fuse a non-Ig moiety to the C-terminus of the IgA or IgM CH4 domain.

It is also convenient to truncate the IgA or IgM heavy chain before the most C-terminal cysteine, or to mutate this cysteine, especially when the IgG/IgA or IgG/IgM hybrid isotype fusion protein is expressed in the absence of a J chain. The normal function of this C-terminal cysteine is to form a disulfide bond with the J chain. It is often desirable to express an IgG/IgA or IgG/IgM hybrid isotype fusion protein in the absence of a co-expressed J chain, especially when fusing the non-Ig moiety to the C-terminus of the heavy chain.

For example, an IgG-IgM hybrid isotype fusion protein is constructed as follows. The plasmid pdHL7-huKSγ1-IL2 is capable of expressing an antibody with variable regions that bind to Epithelial Cell Adhesion Molecule and constant regions from human IgG1. This plasmid contains a unique Ngo M IV site in the intron between the IgG1 CH2 and CH3 coding sequences, and also contains a unique XmaI site at the junction between the coding sequences for the IgG1 CH3 and the IL-2 moieties. A DNA fragment encoding the human IgM CH3 and CH4 sequences is generated by PCR amplification from human genomic DNA using the following primers:

5'-GCA GCCGGC CCTGAGCCTTGGCTTCCCAGAG CG-3' (SEQ ID NO: 29); and

5'-GCT CCCGGG TCAGTAGCAGGTGCCAGCTGTG TCG-3' (SEQ ID NO: 30)

Alternatively, the following primers are used; these have the feature that the C-terminal-most cysteine in the IgM moiety is mutated to a serine.

5'-GCA GCCGGC CCTGAGCCTTGGCTTCCCAGAG CG-3'; (SEQ ID NO: 31) and

5'-GCT CCCGGG TCAGTAGCTGGTGCCAGCTGTG TCG-3'(SEQ ID NO: 32);

The resulting DNA fragment is cleaved with Ngo M IV and XmaI and is then directly or indirectly ligated to pdHL7-huKSγ1-IL2 that has been cut with Ngo M IV and XmaI. For example, the PCR fragment encoding the IgM CH3 and CH4 domains is first subcloned into a vector such as the TA cloning vector (Invitrogen, Carlsbad Calif.), the sequence of the insert is verified, and then the insert is removed using Ngo M IV and XmaI and ligated into pdHL7-huKSγ1-IL2. The amino acid sequence of a resulting hybrid isotype heavy chain, fused to human IL-2 is shown in SEQ ID 33. The IgM portion of the fusion protein is underlined. Because of naturally occuring polymorphisms in human IgM heavy chains, it is also possible to generate closely related sequences that are functionally similar.

ASTKGPSVFPLAPSSKSTSGGTAALGCLVKDYFPEP (SEQ ID NO:33)

VTVSWNSGALTSGVHTFPAVLQSSGLYSLSSVVTVP

SSSLGTQTYICNVNHKPSNTKVDKKVEPKSCDKTHT

CPPCPAPELLGGPSVFLFPPKPKDTLMISRTPEVTC

VVVDVSHEDPEVKFNWYVDGVEVHNAKTKPREEQYN

STYRVVSVLTVLHQDWLNGKEYKCKVSNKALPAPIE

KTISKAK<u>DQDTAIRVFAIPPSFASIFLTKSTKLTCL</u>

<u>VTDLTTYDSVTISWTRQNGEAVKTHTNISESHPNAT</u>

<u>FSAVGEASICEDDWNSGERFTCTVTHTDLPSPLKQT</u>

<u>ISRPKGVALHRPDVYLLPPAREQLNLRESATITCLV</u>

<u>TGFSPADVFVQWMQRGQPLSPEKYVTSAPMPEPQAP</u>

<u>GRYFAHSILTVSEEEWNTGETYTCVVAHEALPNRVT</u>

<u>ERTVDKSTGKPTLYNVSLVMSDTAGTCY</u>

Many alternative DNA construction strategies are possible. For example, a DNA sequence encoding the IgM CH3 and CH4 domains may be generated by RT-PCR from an IgM-expressing cell line or cell population. The 3' PCR primer may be identical to that shown above, but the 5' primer incorporates an artificial 5' splice site between the Ngo M IV site and the beginning of the IgM CH3 coding sequence.

Eukaryotic cells are then transformed with the resulting plasmid, pdHL7-huKSγ1/μ-IL2, and the resulting protein is expressed and secreted from the cells. For example, the cells and methods described in the previous Examples are used. The purified protein is tested, for example by electron microscopy or by size-exclusion chromatography, and found to have a multimeric structure. The purified protein is further studied, for example by peptide mapping, and it is found that the cysteine in the sequence . . . ASICEDD . . . (SEQ ID NO: 34) forms an interchain disulfide bond with other IgG/IgM hybrid isotype subunits. An example of such a linkage is illustrated in FIG. 4. In addition to the pentameric structure of FIG. 4, the final form of the IgG/IgM hybrid isotype protein may be hexameric or some other type of multimeric structure.

The resulting IgG/IgM hybrid isotype fusion protein is found to bind to Fcγ receptors. For example, the fusion protein binds to J774 cells in a manner that is competitive with human IgG.

Example 15

Expression of Hybrid Isotype Antibody Using Components of IgG1 and IgG4

The purpose of the experiments in Examples 15–17 was, in part, to demonstrate the utility of hybrid isotype antibodies in improving the assembly of molecules consisting primarily of IgG4. In general, a commonly preferred form of an IgG molecule is the $H_2L_2$ form, with two heavy chains and two light chains. However, a significant fraction of IgG4 antibodies are synthesized as HL "half molecules" with one heavy chain and one light chain. Angal et al. (1993; Molec. Immunol. 30:105) described a serine to proline substitution that decreased the amount of "half molecules" found in secreted human IgG4.

This example compares the assembly properties of three antibodies containing the same V regions: an IgG4 form, a form with a hinge from IgG1 and the CH1, CH2, and CH3 domains from IgG4, and an IgG4 form with a mutation in the hinge region (Angal et al., ibid.).

Using standard plasmid construction techniques, a plasmid termed pdHL7-KS-γ4 was constructed. This plasmid is identical to the plasmid pdHL7-huKSγ2 described in Example 5, except that it encodes an IgG4 heavy chain constant region instead of an IgG2 heavy chain constant region.

To construct pdHL7-KS-γ4h, the pdHL7-KS-γ2h plasmid was grown in a dcm(−) strain of E. coli, plasmid DNA isolated, and the 60 bp PstI-StuI fragment encoding the modified IgG1 hinge region was isolated and used to replace the corresponding fragment in pdHL7-KS-γ4.

For comparison, the IgG4 form with a mutation in the hinge region (Angal et al., ibid.) was constructed as follows. An oligonucleotide duplex encoding the γ4 hinge with the serine to proline substitution, and a 5' PstI sticky end and a 3' StuI blunt end, was designed as follows:

```
PstI     E   S   K   Y   G   P   P   C   P   P   C   P               (SEQ ID NO:35)
    GAG TCC AAA TAT GGT CCC CCA TGC CCA CCT TGC CCA GGTAAG            (complement of SEQ ID NO:36)
ACGT CTC AGG TTT ATA CCA GGGGGT ACG GGT GGA ACG GGT CCATTC            (SEQ ID. NO:36)

StuI
CCAACCCAGG
GGTTGGGTCC
```

This oligonucleotide duplex was used to replace the corresponding DNA fragment in pdHL7-KS-γ4 to give pdHL7-KS-γ4(S to P).

The pdHL7-KS-γ4, pdHL7-KS-γ4h, and pdHL7-KS-γ4(S to P) plasmids were transfected into mammalian cells according to standard procedures, for example, as described in Lo et al., (1998; Protein Engineering 11:495–500). From the supernatants of transfected cells, the antibody proteins encoded by pdHL7-KS-γ4, pdHL7-KS-γ4h, and pdHL7-KS-γ4(S to P) were purified and characterized by SDS gel electrophoresis in which reduced and non-reduced samples were compared.

By examining non-reduced molecules, it was found that the KS-γ4 antibody population existed as about 50% HL "half-molecules" and 50% $H_2L_2$ molecules. In contrast, the KS-γ4h antibody population and the KS-γ4 (S to P) antibody population existed almost entirely as $H_2L_2$ molecules. The proportion of HL half-molecules was about the same in the KS-γ4h antibody population and the KS-γ4 (S to P) antibody population. When reduced molecules were examined, the pattern of heavy and light chains seen with KS-γ4, KS-γ4h, and KS-γ4(S to P) were indistinguishable.

Example 16

Expression of Hybrid Isotype Antibody Fusion Proteins Using Components of IgG1 and IgG4.

The plasmid pdHL7-KS-γ4-IL2 was described in Gillies et al. (Cancer Research [1999] 59:2159). This plasmid encodes an antibody fusion protein with V regions that recognize the EpCAM antigen and contain the heavy chain of IgG4 with interleukin-2 fused at its C-terminus.

By recombinant DNA procedures analogous to those used in Example 15, the plasmids pdHL7-KS-γ4h-IL2 and pdHL7-KS-γ4 (S to P)-IL2 were constructed. The plasmids pdHL7-KS-γ4-IL2, pdHL7-KS-γ4h-IL2 and pdHL7-KS-γ4 (S to P)-IL2 transfected into mammalian cells, and the corresponding proteins were expressed and purified according to standard procedures, for example, as described in Lo et al. (ref). From the supernatants of transfected cells, the fusion proteins encoded by pdHL7-KS-γ4-IL2, pdHL7-KS-γ4h-IL-2, and pdHL7-KS-γ4(S to P)-IL-2 were purified and characterized by SDS gel electrophoresis in which reduced and non-reduced samples were compared.

By examining non-reduced molecules, it was found that the KS-γ4-IL-2 fusion protein population existed as about 50% HL "half-molecules" and 50% $H_2L_2$ molecules. In contrast, the KS-γ4h-IL-2 fusion protein population and the KS-γ4 (S to P)-IL-2 fusion protein population existed almost entirely as $H_2L_2$ molecules. The proportion of HL half-molecules was about the same in the KS-γ4h-IL-2 fusion protein population and the KS-γ4(S to P)-IL-2 fusion protein population. When reduced molecules were examined, the pattern of heavy and light chains seen with KS-γ4-IL-2, KS-γ4h-IL-2, and KS-γ4(S to P)-IL-2 were indistinguishable.

Example 17

Expression of Hybrid Isotype Fc Fusion Proteins Using Components of IgG1 and IgG4.

To create a set of plasmids for expression of fusion proteins containing a hinge region, a CH2 and CH3 domain, and a non-Ig moiety, in which the Ig moieties were derived from IgG4 and IgG1, the following steps were undertaken.

First, using procedures analogous to those described in Example 1, an expression vector encoding the Fc region from IgG4 was created by replacing the IgG1-derived DNA sequences of pdCs-huFcγ1 (Lo et al., [1998] Protein Engineering 11:495–500) with sequences encoding the corresponding part of IgG4. Specifically, the following oligonucleotide E S K Y G P P C P S C (SEQ ID NO: 37) C TTA AGC GAG TCC AAA TAT GGT CCC CCA TGC CCA TCA TGC (SEQ ID NO: 38)

which encodes an AflII site at its 5' end, was used as a 5' primer to amplify a DNA segment encoding the IgG4 hinge, CH2, and CH3 regions. The 3' primer contained a XhoI site at its 5' end, analogously to the primer used in Example 1 to amplify the IgG2 Fc region. The resulting AflII-XhoI fragment was inserted into XhoI+AflII-cut pdCs-huFcγ1 to create pdCs-huFcγ4.

To facilitate the insertion of nucleic acids encoding non-IgG moieties at the C-terminus of Fcγ4, a SmaI site was created by introducing the following Leu to Pro change near the C-terminus of the Fcγ4 coding region in pdCs-huFcγ4, as follows:

```
   S   L   G   K STOP   (SEQ ID NO:39)              S   P   G   K STOP   (SEQ ID NO:40)

TCT CTG GGT AAA TGA  (SEQ ID NO:41) was changed to TCC CCG GGT AAA TGA.  (SEQ ID NO:42)
```

Standard site-directed mutagenesis techniques were used to introduce the SmaI site into pdCs-huFcγ4.

To create a plasmid, termed pdCs-huFcγ4h, encoding the modified IgG1 hinge followed by the IgG4 CH2 and CH3 domains, the StuI-XhoI fragment of pdCs-huFcγ2h (Example 1), which encodes the IgG2 CH2 and CH3 domains, was replaced with the corresponding fragment from pdCs-huFcγ4. In this construction, each parental plasmid was derived from a dcm(−) strain of *E. coli*. The pdCs-huFcγ4 plasmid was completely digested with XhoI and partially digested with StuI, since there is an additional StuI site in the γ4-encoding DNA, to yield fragments of about 300, 500 and 800 base pairs. The approximately 800 base pair fragment was used to replace the corresponding fragment in pdCs-huFcγ2h.

An IFNβ cDNA was cloned by PCR using sense primer CCCGGGT ATG AGC TAC AAC TTG CTT GGA TTC (SEQ ID NO: 43), where ATG is the N-terminal residue of the mature protein and CCCGGG is an introduced SmaI restriction site, and reverse primer CTCGAG TCA GTT TCG GAG GTA ACC TGT AAG (SEQ ID NO: 44), where TCA is the anticodon of the translation stop codon and CTCGAG is an introduced XhoI restriction site. The template DNA was pLG117R (Taniguchi et al., [1980] Proc. Nat. Acad. Sci. USA 77:5230–5233) and was purchased from the American Type Culture Collection (ATCC number 31903). After sequence verification, the cloned SmaI-XhoI fragment was ligated to the SmaI and XhoI sites of the pdCs-huFcγ4 expression vector to give pdCs-huFcγ4-IFNβ. An analogous pdCs-huFcγ4h-IFNβ expression plasmid was also constructed by similar methods.

To construct the pdCs-huFcγ4(S to P)-IFNβ expression plasmid, an oligonucleotide duplex encoding the γ4 hinge with the serine to proline substitution, and a 5' AflII sticky end and a 3' StuI blunt end was synthesized as follows:

```
AflII    E   S   K   Y   G   P   P   C   P                              (SEQ ID NO:45)
P    C   P                       StuI
TTA AGC GAG TCC AAA TAT GGT CCC CCA TGC CCA CCT TGC CCA GGT AAGCCAACCCAGG (SEQ ID NO:46)
    G CTC AGG TTT ATA CCA GGG GGT ACG GGT GGA ACG GGT CCA TTC GGTTGGGTCC (complement of SEQ ID NO:46)
```

This DNA was used to replace the corresponding DNA fragment in pdCs-Fc-g4-IFNβ to give pdCs-huFcγ4(S to P)-IFNβ.

The plasmids pdCs-huFcγ4-IFNβ, pdCs-huFcγ4h-IFNβ, and pdCs-huFcγ4(S to P)-IFNβ were each transfected into mammalian cells. The expressed Fc-containing proteins were purified and examined by reducing and non-reducing SDS gel electrophoresis. It was found that a significant proportion of the huFcγ4-IFNβ protein expressed from mammalian cells was monomeric half-molecules rather than dimeric, normal antibodies. However, the expressed huFcγ4h-IFNβ, and huFcγ4(S to P)-IFNβ fusion proteins were almost entirely correctly assembled dimers. For both the huFcγ4h-IFNβ, and huFcγ4(S to P)-IFNβ fusion proteins, the proportion of monomer was about the same.

Taken together, the results of Examples 15, 16, and 17 indicate that hybrid isotype antibodies and Ig fusion proteins consisting primarily of IgG4 but having the modified IgG1 hinge have superior assembly properties as compared to corresponding proteins derived entirely from IgG4. In addition, the results of Examples 15–17, in combination with other Examples, illustrate that the improved assembly of hybrid isotype proteins can be manifested in several different ways. For example, in some cases a hybrid isotype antibody or fusion protein shows reduced aggregation, as compared to a corresponding single-isotype antibody or Ig fusion protein; and in other cases the hybrid isotype antibody or fusion protein shows enhanced correct oligomerization, as compared to a corresponding single-isotomer antibody or Ig fusion protein.

Example 18

Expression of Hybrid Isotype Fc Fusion Proteins Using Components of IgG1 and IgG4.

To generate an Fc-erythropoietin fusion protein that is minimally aggregated when expressed from mammalian cells, the following expression plasmid was constructed using standard molecular biology techniques. An XmaI-XhoI DNA fragment containing a form of the human erythropoietin coding sequence with mutations resulting in the amino acid substitutions His32Gly, Cys33Pro, Trp88Cys, and Pro90Ala, as disclosed in WO01/36489, was used. The corresponding protein sequence is shown in SEQ ID NO: 47:

APPRLICDSRVLERYLLEAKEAENITTGCAEGPSLNE
NITVPDTKVNFYAWKRMEVGQQAVEVWQGLALL
SEAVLRGQALLVNSSQPCEGLQLHVDKAVSGLRSL
TTLLRALGAQKEAISPPDAASAAPLRTITADTFRKL
F RVYSNFLRGKLKLYTGEACRTGDR

This XmaI-XhoI DNA fragment was inserted into a plasmid vector that encodes a hinge region from IgG1 and a CH2 and CH3 region from IgG2 that was essentially identical to the vector constructed in Example 1, except that there were two sets of mutations that resulted in amino acid substitutions in the region of the CH3 C-terminus, such that the sequence at the junction of the CH3 C-terminus and the Epo N-terminus is as follows:

TQKSATATPGA-APPRLI (SEQ ID NO: 48)

The first set of mutations, which change the sequence KSLSLSPG (SEQ ID NO: 49) of the IgG2 CH3 region to KSATATPG (SEQ ID NO: 45), is disclosed in U.S. patent application Ser. No. 60/280,625. The effect of the substitution of Leu-Ser-Leu-Ser (position 3 to position 6 of SEQ ID NO: 49) with Ala-Thr-Ala-Thr (position 3 to position 6 of SEQ ID NO: 50) is to remove potential human non-self T-cell epitopes that may arise because the junction between human Fc and human erythropoietin contains non-self peptide sequences. The second set consisting of the single amino acid substitution K to A at the C-terminal amino acid of the CH3 region, is disclosed in U.S. patent application Ser. No. 09/780,668.

The resulting plasmid was transfected into NS/0 cells and the Fc-Epo fusion protein was expressed and purified according to the procedures of Examples 1 and 2. After purification based on binding to protein A, the huFcγ2h-huEpo protein containing the IgG2 CH3 and erythropoietin substitutions described above was characterized by size exclusion chromatography and found to consist of 97% monomer and 90% monomer in two independent preparations. The huFcγ2h-huEpo protein containing the IgG2 CH3 and erythropoietin substitutions described above was found to be about as active, on a molar basis, as human erythropoietin in a cell-based assay-that measured the ability of an erythropoietin protein to stimulate TF-1 cell division. The assay was performed as described in WO01/36489.

In addition, fusions of non-mutant human erythropoietin to the C-terminus of an Fc region consisting of either IgG1(hinge-CH2-CH3), IgG2(hinge-CH2-CH3), or IgG1(hinge)-IgG2(CH2-CH3) were characterized. Expression plasmids comprising non-mutant human Fc sequences and non-mutant erythropoietin sequences were constructed analogously to the plasmid described above and in Example 1. NS/0 cells were transfected with the Fcγ1-Epo, Fcγ2-Epo, and Fcγ2h-Epo expression plasmids, and stable clones were isolated after screening an approximately equal number of clones for each plasmid. The best-producing clones yielded 50 μg/ml for Fcγ1-Epo, 20 μg/ml for Fcγ2-Epo, and 120 μg/ml for Fcγ2h-Epo.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

Incorporation by Reference

All patents, patent applications, and scientific publications mentioned herein above are incorporated by reference into this application in their entirety.

What is claimed is:

1. A fusion protein comprising an immunoglobulin moiety fused to a non-immunoglobulin moiety, wherein the immunoglobulin moiety comprises:
   an IgG1 hinge positioned at the N-terminus of the immunoglobulin moiety; and
   a CH2 domain of a second antibody isotype adjacent to the IgG1 hinge.

2. The fusion protein of claim 1 wherein the CH2 domain is an IgG2 CH2 domain.

3. The fusion protein of claim 1 wherein the non-immunoglobulin moiety is a cytokine.

4. The fusion protein of claim 1 wherein the non-immunoglobulin moiety is an erythropoietin molecule.

5. The fusion protein of claim 1 wherein the most N-terminal cysteine of the IgG1 hinge is mutated.

6. The fusion protein of claim 2 wherein the non-immunoglobulin moiety is a cytokine.

7. The fusion protein of claim 2 wherein the non-immunoglobulin moiety is an erythropoietin molecule.

8. The fusion protein of claim 2 wherein the most N-terminal cysteine of the IgG1 hinge is mutated.

9. The fusion protein of claim 1 wherein the non-immunoglobulin moiety is fused to the N-terminus of the imunoglobulin moiety.

10. The fusion protein of claim 1 wherein the non-immunoglobulin moiety is fused to the C-terminus of the immunoglobulin moiety.

* * * * *

```
                              SEQUENCE LISTING

<160> NUMBER OF SEQ ID NOS: 50

<210> SEQ ID NO 1
<211> LENGTH: 12
<212> TYPE: PRT
<213> ORGANISM: artificial sequence
<220> FEATURE:
<223> OTHER INFORMATION: IgG2 hinge sequence

<400> SEQUENCE: 1

Glu Arg Lys Ser Ser Val Glu Cys Pro Pro Cys Pro
1               5                   10

<210> SEQ ID NO 2
<211> LENGTH: 12
<212> TYPE: PRT
<213> ORGANISM: artificial sequence
<220> FEATURE:
<223> OTHER INFORMATION: IgG2-IgG4 hybrid hinge sequence

<400> SEQUENCE: 2

Glu Ser Lys Tyr Gly Val Glu Cys Pro Pro Cys Pro
1               5                   10

<210> SEQ ID NO 3
<211> LENGTH: 5
<212> TYPE: PRT
<213> ORGANISM: artificial sequence
<220> FEATURE:
<223> OTHER INFORMATION: IgE-CH2 domain sequence

<400> SEQUENCE: 3

Val Asn Leu Thr Trp
1               5

<210> SEQ ID NO 4
<211> LENGTH: 5
<212> TYPE: PRT
<213> ORGANISM: artificial sequence
<220> FEATURE:
<223> OTHER INFORMATION: IgG1 CH2 domain sequence

<400> SEQUENCE: 4

Val Lys Phe Asn Trp
1               5

<210> SEQ ID NO 5
<211> LENGTH: 5
<212> TYPE: PRT
<213> ORGANISM: artificial sequence
<220> FEATURE:
<223> OTHER INFORMATION: IgG3 CH2 domain sequence

<400> SEQUENCE: 5

Val Gln Phe Lys Trp
1               5

<210> SEQ ID NO 6
<211> LENGTH: 5
```

```
<212> TYPE: PRT
<213> ORGANISM: artificial sequence
<220> FEATURE:
<223> OTHER INFORMATION: glycosylation site from IgD

<400> SEQUENCE: 6

Asn Thr Ser Gly Phe
1               5

<210> SEQ ID NO 7
<211> LENGTH: 5
<212> TYPE: PRT
<213> ORGANISM: artificial sequence
<220> FEATURE:
<223> OTHER INFORMATION: glycosylation site from IgD

<400> SEQUENCE: 7

Leu Asn Ala Ser Arg
1               5

<210> SEQ ID NO 8
<211> LENGTH: 29
<212> TYPE: DNA
<213> ORGANISM: artificial sequence
<220> FEATURE:
<223> OTHER INFORMATION: forward primer for human Fc gamma 2

<400> SEQUENCE: 8
ccttaagcga gcgcaaatgt tgtgtcgag                                    29

<210> SEQ ID NO 9
<211> LENGTH: 21
<212> TYPE: DNA
<213> ORGANISM: artificial sequence
<220> FEATURE:
<223> OTHER INFORMATION: human Fc gamma 2 hinge coding region

<400> SEQUENCE: 9
gagcgcaaat gttgtgtcga g                                            21

<210> SEQ ID NO 10
<211> LENGTH: 29
<212> TYPE: DNA
<213> ORGANISM: artificial sequence
<220> FEATURE:
<223> OTHER INFORMATION: reverse primer for human Fc gamma 2

<400> SEQUENCE: 10
cctcgagtca tttacccggg gacagggag                                    29

<210> SEQ ID NO 11
<211> LENGTH: 30
<212> TYPE: DNA
<213> ORGANISM: artificial sequence
<220> FEATURE:
<223> OTHER INFORMATION: DNA sequence for upper CH3 region

<400> SEQUENCE: 11
ctgcccccat cccgggagga gatgaccaag                                   30

<210> SEQ ID NO 12
<211> LENGTH: 30
<212> TYPE: DNA
<213> ORGANISM: artificial sequence
<220> FEATURE:
<223> OTHER INFORMATION: forward primer for introducing a C to A
      substitution in the upper CH3 region
```

```
<400> SEQUENCE: 12
ctgcccccat cacgggagga gatgaccaag                                            30

<210> SEQ ID NO 13
<211> LENGTH: 34
<212> TYPE: DNA
<213> ORGANISM: artificial sequence
<220> FEATURE:
<223> OTHER INFORMATION: reverse primer for introducing a C to A
      substitution in the CH3 region

<400> SEQUENCE: 13
ggtcatctcc tcccgtgatg ggggcagggt gtac                                       34

<210> SEQ ID NO 14
<211> LENGTH: 12
<212> TYPE: PRT
<213> ORGANISM: artificial sequence
<220> FEATURE:
<223> OTHER INFORMATION: gamma 2 hinge

<400> SEQUENCE: 14

Glu Arg Lys Cys Cys Val Glu Cys Pro Pro Cys Pro
1               5                   10

<210> SEQ ID NO 15
<211> LENGTH: 62
<212> TYPE: DNA
<213> ORGANISM: artificial sequence
<220> FEATURE:
<223> OTHER INFORMATION: gamma 2 hinge exon

<400> SEQUENCE: 15
cttaagcgag cgcaaatgtt gtgtcgagtg cccaccgtgc ccaggtaagc cagcccaggc           60
ct                                                                         62

<210> SEQ ID NO 16
<211> LENGTH: 15
<212> TYPE: PRT
<213> ORGANISM: artificial sequence
<220> FEATURE:
<223> OTHER INFORMATION: gamma 1 hinge sequence with a Cys to Ser
      mutation

<400> SEQUENCE: 16

Glu Pro Lys Ser Ser Asp Lys Thr His Thr Cys Pro Pro Cys Pro
1               5                   10                  15

<210> SEQ ID NO 17
<211> LENGTH: 71
<212> TYPE: DNA
<213> ORGANISM: artificial sequence
<220> FEATURE:
<223> OTHER INFORMATION: DNA fragment containing gamma 1 hinge exon

<400> SEQUENCE: 17
cttaagcgag cccaaatctt ctgacaaaac tcacacatgc ccaccgtgcc caggtaagcc           60
agcccaggcc t                                                               71

<210> SEQ ID NO 18
<211> LENGTH: 112
<212> TYPE: DNA
<213> ORGANISM: artificial sequence
<220> FEATURE:
```

<223> OTHER INFORMATION: sequence encoding glucagon-like peptide 1

<400> SEQUENCE: 18
cttaagccat gctgaaggga cctttactag tgatgtaagt tcttatttgg aaggccaagc    60
tgccaaggaa ttcattgctt ggctggtgaa aggccgagga ggatccttaa gc           112

<210> SEQ ID NO 19
<211> LENGTH: 31
<212> TYPE: PRT
<213> ORGANISM: artificial sequence
<220> FEATURE:
<223> OTHER INFORMATION: glucagon-like peptide 1

<400> SEQUENCE: 19

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 20
<211> LENGTH: 19
<212> TYPE: DNA
<213> ORGANISM: artificial sequence
<220> FEATURE:
<223> OTHER INFORMATION: forward primer for immunoglobulin gamma 2
      constant region

<400> SEQUENCE: 20
caagctttct ggggcgagc                                                 19

<210> SEQ ID NO 21
<211> LENGTH: 29
<212> TYPE: DNA
<213> ORGANISM: artificial sequence
<220> FEATURE:
<223> OTHER INFORMATION: reverse primer for immunoglobulin gamma 2
      constant region

<400> SEQUENCE: 21
cctcgagtca tttacccggg gacagggag                                      29

<210> SEQ ID NO 22
<211> LENGTH: 19
<212> TYPE: DNA
<213> ORGANISM: artificial sequence
<220> FEATURE:
<223> OTHER INFORMATION: forward primer for gamma 1 hinge region

<400> SEQUENCE: 22
ctgcagagcc caaatcttc                                                 19

<210> SEQ ID NO 23
<211> LENGTH: 19
<212> TYPE: DNA
<213> ORGANISM: artificial sequence
<220> FEATURE:
<223> OTHER INFORMATION: reverse primer for gamma 1 hinge region

<400> SEQUENCE: 23
cagctggggc ctgtccctg                                                 19

<210> SEQ ID NO 24
<211> LENGTH: 10
<212> TYPE: DNA
<213> ORGANISM: artificial sequence

```
<220> FEATURE:
<223> OTHER INFORMATION: sequence in pDHL2-huKS antibody

<400> SEQUENCE: 24
gggtaaatga                                                          10

<210> SEQ ID NO 25
<211> LENGTH: 89
<212> TYPE: DNA
<213> ORGANISM: artificial sequence
<220> FEATURE:
<223> OTHER INFORMATION: IgA1 hinge exon

<400> SEQUENCE: 25
cttaagtccc tcaactccac ctaccccatc tccctcaact ccacctaccc catctccctc   60
atgctgccac ggtaagccag cccaggcct                                     89

<210> SEQ ID NO 26
<211> LENGTH: 21
<212> TYPE: PRT
<213> ORGANISM: artificial sequence
<220> FEATURE:
<223> OTHER INFORMATION: IgA1 hinge region

<400> SEQUENCE: 26

Pro Ser Thr Pro Pro Thr Pro Ser Pro Ser Thr Pro Pro Thr Pro Ser
 1               5                  10                  15

Pro Ser Cys Cys His
            20

<210> SEQ ID NO 27
<211> LENGTH: 85
<212> TYPE: DNA
<213> ORGANISM: artificial sequence
<220> FEATURE:
<223> OTHER INFORMATION: top replacement strand

<400> SEQUENCE: 27
ttaagtccct caactccacc taccccatct ccctcaactc cacctacccc atctccctca   60
tgctgccacg gtaagccagc ccagg                                         85

<210> SEQ ID NO 28
<211> LENGTH: 81
<212> TYPE: DNA
<213> ORGANISM: artificial sequence
<220> FEATURE:
<223> OTHER INFORMATION: bottom replacement strand

<400> SEQUENCE: 28
cctgggctgg cttaccgtgg cagcatgagg gagatggggt aggtggagtt gagggagatg   60
gggtaggtgg agttgaggga c                                             81

<210> SEQ ID NO 29
<211> LENGTH: 33
<212> TYPE: DNA
<213> ORGANISM: artificial sequence
<220> FEATURE:
<223> OTHER INFORMATION: primer for IgM CH3 and CH4

<400> SEQUENCE: 29
gcagccggcc ctgagccttg gcttcccaga gcg                                33

<210> SEQ ID NO 30
```

```
<211> LENGTH: 34
<212> TYPE: DNA
<213> ORGANISM: artificial sequence
<220> FEATURE:
<223> OTHER INFORMATION: primer for IgM CH3 and CH4

<400> SEQUENCE: 30
gctcccgggt cagtagcagg tgccagctgt gtcg                              34

<210> SEQ ID NO 31
<211> LENGTH: 33
<212> TYPE: DNA
<213> ORGANISM: artificial sequence
<220> FEATURE:
<223> OTHER INFORMATION: primer for IgM for mutating the C-terminal most
      Cys to Ser

<400> SEQUENCE: 31
gcagccggcc ctgagccttg gcttcccaga gcg                               33

<210> SEQ ID NO 32
<211> LENGTH: 34
<212> TYPE: DNA
<213> ORGANISM: artificial sequence
<220> FEATURE:
<223> OTHER INFORMATION: primer for IgM for mutating the C-terminus Cys
      to a Ser

<400> SEQUENCE: 32
gctcccgggt cagtagctgg tgccagctgt gtcg                              34

<210> SEQ ID NO 33
<211> LENGTH: 460
<212> TYPE: PRT
<213> ORGANISM: artificial sequence
<220> FEATURE:
<223> OTHER INFORMATION: constant region for IgG1-IgM hybrid

<400> SEQUENCE: 33
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

-continued

```
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Asp
    210                 215                 220
Gln Asp Thr Ala Ile Arg Val Phe Ala Ile Pro Pro Ser Phe Ala Ser
225                 230                 235                 240
Ile Phe Leu Thr Lys Ser Thr Lys Leu Thr Cys Leu Val Thr Asp Leu
                245                 250                 255
Thr Thr Tyr Asp Ser Val Thr Ile Ser Trp Thr Arg Gln Asn Gly Glu
            260                 265                 270
Ala Val Lys Thr His Thr Asn Ile Ser Glu Ser His Pro Asn Ala Thr
        275                 280                 285
Phe Ser Ala Val Gly Glu Ala Ser Ile Cys Glu Asp Asp Trp Asn Ser
    290                 295                 300
Gly Glu Arg Phe Thr Cys Thr Val Thr His Thr Asp Leu Pro Ser Pro
305                 310                 315                 320
Leu Lys Gln Thr Ile Ser Arg Pro Lys Gly Val Ala Leu His Arg Pro
                325                 330                 335
Asp Val Tyr Leu Leu Pro Pro Ala Arg Glu Gln Leu Asn Leu Arg Glu
            340                 345                 350
Ser Ala Thr Ile Thr Cys Leu Val Thr Gly Phe Ser Pro Ala Asp Val
        355                 360                 365
Phe Val Gln Trp Met Gln Arg Gly Gln Pro Leu Ser Pro Glu Lys Tyr
    370                 375                 380
Val Thr Ser Ala Pro Met Pro Glu Pro Gln Ala Pro Gly Arg Tyr Phe
385                 390                 395                 400
Ala His Ser Ile Leu Thr Val Ser Glu Glu Trp Asn Thr Gly Glu
                405                 410                 415
Thr Tyr Thr Cys Val Val Ala His Glu Ala Leu Pro Asn Arg Val Thr
            420                 425                 430
Glu Arg Thr Val Asp Lys Ser Thr Gly Lys Pro Thr Leu Tyr Asn Val
        435                 440                 445
Ser Leu Val Met Ser Asp Thr Ala Gly Thr Cys Tyr
    450                 455                 460

<210> SEQ ID NO 34
<211> LENGTH: 7
<212> TYPE: PRT
<213> ORGANISM: artificial sequence
<220> FEATURE:
<223> OTHER INFORMATION: peptide sequence in the IgG1-IgM hybrid

<400> SEQUENCE: 34

Ala Ser Ile Cys Glu Asp Asp
1               5

<210> SEQ ID NO 35
<211> LENGTH: 12
<212> TYPE: PRT
<213> ORGANISM: artificial sequence
<220> FEATURE:
<223> OTHER INFORMATION: IgG4 hinge region with a Ser to Pro mutation

<400> SEQUENCE: 35

Glu Ser Lys Tyr Gly Pro Pro Cys Pro Pro Cys Pro
1               5                   10
```

```
<210> SEQ ID NO 36
<211> LENGTH: 56
<212> TYPE: DNA
<213> ORGANISM: artificial sequence
<220> FEATURE:
<223> OTHER INFORMATION: oligonucleotide duplex

<400> SEQUENCE: 36
acgtctcagg tttataccag ggggtacggg tggaacgggt ccattcggtt gggtcc        56

<210> SEQ ID NO 37
<211> LENGTH: 11
<212> TYPE: PRT
<213> ORGANISM: artificial sequence
<220> FEATURE:
<223> OTHER INFORMATION: IgG4 hinge

<400> SEQUENCE: 37

Glu Ser Lys Tyr Gly Pro Pro Cys Pro Ser Cys
1               5                  10

<210> SEQ ID NO 38
<211> LENGTH: 40
<212> TYPE: DNA
<213> ORGANISM: artificial sequence
<220> FEATURE:
<223> OTHER INFORMATION: primer for IgG4 hinge, CH2 and CH3 regions

<400> SEQUENCE: 38
cttaagcgag tccaaatatg gtcccccatg cccatcatgc                          40

<210> SEQ ID NO 39
<211> LENGTH: 4
<212> TYPE: PRT
<213> ORGANISM: artificial sequence
<220> FEATURE:
<223> OTHER INFORMATION: peptide sequence near the C-terminus of the Fc
      gamma 4 coding region

<400> SEQUENCE: 39

Ser Leu Gly Lys
1

<210> SEQ ID NO 40
<211> LENGTH: 4
<212> TYPE: PRT
<213> ORGANISM: artificial sequence
<220> FEATURE:
<223> OTHER INFORMATION: peptide sequence near the C-terminus of the Fc
      gamma 4 coding region with a Leu to Pro mutation

<400> SEQUENCE: 40

Ser Pro Gly Lys
1

<210> SEQ ID NO 41
<211> LENGTH: 15
<212> TYPE: DNA
<213> ORGANISM: artificial sequence
<220> FEATURE:
<223> OTHER INFORMATION: sequence near the C-terminus of the Fc gamma 4
      coding region

<400> SEQUENCE: 41
tctctgggta aatga                                                    15
```

<210> SEQ ID NO 42
<211> LENGTH: 15
<212> TYPE: DNA
<213> ORGANISM: artificial sequence
<220> FEATURE:
<223> OTHER INFORMATION: sequence near the C-terminus of the Fc gamma 4
      coding region with a Leu to Pro mutation

<400> SEQUENCE: 42
tccccgggta aatga                                                    15

<210> SEQ ID NO 43
<211> LENGTH: 31
<212> TYPE: DNA
<213> ORGANISM: artificial sequence
<220> FEATURE:
<223> OTHER INFORMATION: IFN beta sense primer

<400> SEQUENCE: 43
cccgggtatg agctacaaact tgcttggatt c                                 31

<210> SEQ ID NO 44
<211> LENGTH: 30
<212> TYPE: DNA
<213> ORGANISM: artificial sequence
<220> FEATURE:
<223> OTHER INFORMATION: IFN beta reverse primer

<400> SEQUENCE: 44
ctcgagtcag tttcggaggt aacctgtaag                                    30

<210> SEQ ID NO 45
<211> LENGTH: 12
<212> TYPE: PRT
<213> ORGANISM: artificial sequence
<220> FEATURE:
<223> OTHER INFORMATION: Fc gamma 4 hinge region with a Ser to Pro
      mutation

<400> SEQUENCE: 45

Glu Ser Lys Tyr Gly Pro Pro Cys Pro Pro Cys Pro
1               5                   10

<210> SEQ ID NO 46
<211> LENGTH: 58
<212> TYPE: DNA
<213> ORGANISM: artificial sequence
<220> FEATURE:
<223> OTHER INFORMATION: oligonucleotide duplex encoding the Fc gamma 4
      containing the Ser to Pro mutation

<400> SEQUENCE: 46
ttaagcgagt ccaaatatgg tcccccatgc ccaccttgcc caggtaagcc aacccagg    58

<210> SEQ ID NO 47
<211> LENGTH: 166
<212> TYPE: PRT
<213> ORGANISM: artificial sequence
<220> FEATURE:
<223> OTHER INFORMATION: protein sequence for a mutated form of
      erythropoietin protein

<400> SEQUENCE: 47

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu Gly

```
                20                  25                  30
Pro Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Cys Glu Gly Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 48
<211> LENGTH: 17
<212> TYPE: PRT
<213> ORGANISM: artificial sequence
<220> FEATURE:
<223> OTHER INFORMATION: sequence at the junction of CH3-Epo

<400> SEQUENCE: 48

Thr Gln Lys Ser Ala Thr Ala Thr Pro Gly Ala Ala Pro Pro Arg Leu
1               5                   10                  15

Ile

<210> SEQ ID NO 49
<211> LENGTH: 8
<212> TYPE: PRT
<213> ORGANISM: artificial sequence
<220> FEATURE:
<223> OTHER INFORMATION: IgG2 CH3 sequence

<400> SEQUENCE: 49

Lys Ser Leu Ser Leu Ser Pro Gly
1               5

<210> SEQ ID NO 50
<211> LENGTH: 8
<212> TYPE: PRT
<213> ORGANISM: artificial sequence
<220> FEATURE:
<223> OTHER INFORMATION: IgG2 CH3 region

<400> SEQUENCE: 50

Lys Ser Ala Thr Ala Thr Pro Gly
1               5
```